(12) United States Patent
Blick et al.

(10) Patent No.: US 7,408,147 B2
(45) Date of Patent: Aug. 5, 2008

(54) NANOELECTROMECHANICAL AND MICROELECTROMECHANICAL SENSORS AND ANALYZERS

(75) Inventors: Robert Heinrich Blick, Madison, WI (US); Michael Scott Westphall, Fitchburg, WI (US); Lloyd Michael Smith, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 188 days.

(21) Appl. No.: 11/460,063

(22) Filed: Jul. 26, 2006

(65) Prior Publication Data

US 2007/0023621 A1    Feb. 1, 2007

Related U.S. Application Data

(60) Provisional application No. 60/702,938, filed on Jul. 27, 2005.

(51) Int. Cl.
*H05H 3/02* (2006.01)
*G01N 11/00* (2006.01)

(52) U.S. Cl. .................. 250/251; 250/281; 250/282; 250/288; 250/397

(58) Field of Classification Search .................. 250/251, 250/281, 282, 288, 397
See application file for complete search history.

(56) References Cited

U.S. PATENT DOCUMENTS 6,722,200 B2 *  4/2004  Roukes et al. .................. 73/580
2002/0166962 A1  11/2002  Roukes et al.

FOREIGN PATENT DOCUMENTS

| DE | 199 61 811 | 7/2001 |
|---|---|---|
| WO | WO 02/12443 | 2/2002 |
| WO | WO 03/095616 | 11/2003 |
| WO | WO 03/095617 | 11/2003 |

(Continued)

OTHER PUBLICATIONS

Pescini, L. (May 8, 2003) "Electrochemical Coupling sn Dissipation Mechanisms in Nanoscale Systems," Diploma Thesis, Ludwig-Maximilians-Universitat Munchen and Universita degli Studi di Firenze.

(Continued)

*Primary Examiner*—Nikita Wells
(74) *Attorney, Agent, or Firm*—Greenlee, Winner and Sullivan, P.C.

(57) ABSTRACT

The present invention provides methods, devices and device components for detecting, sensing and analyzing molecules. Detectors of the present invention provide good detection sensitivity over a wide range of molecular masses ranging from a few Daltons up to 10s of megadaltons, which does not decrease as function of molecular mass. Sensors and analyzers of the present invention detect emission from an array of resonators to determine the molecular masses and/or electric charges of molecules which impact or contact an external surface of a membrane that is used to mount and excite the resonators in the array. Resonators in the array are excited via piezoelectric and/or magnetic excitation of the mounting membrane and, optionally, grid electrodes are used in certain configurations for electrically biasing for the resonator array, and for amplification or suppression of emission from the resonators so as to provide detection and mass/electric charge analysis with good sensitivity and resolution.

59 Claims, 30 Drawing Sheets

FOREIGN PATENT DOCUMENTS

WO    WO 2004/041998      5/2004

OTHER PUBLICATIONS

Roukes (2000) "Nanoelectromechanical Systems," *Technical Digest of the 2000 Solid-State Sensor and Actuator Workshop* Transducers Research Foundation, Cleveland, OH.

Aebersold et al. (Mar. 13, 2003) "Mass Spectrometry-Based Proteomics," *Nature* 422:198-207.

Armour et al. (2002)"Transport Via a Quantum Shuttle," *Phys. Rev. B* 66:035333.

Beil et al. (2003) "Comparing Schemes of Displacement Detection and Subharmonic Generation in Nanomachined Mechanical Resonators," *Nanotechnology*. 14:799.

Beil et al. (2002) "p2-21: Broadband Acoustical Tuning of Nano-Electrochemical Sensors," *Proc. IEEE Sensor* 1:1285-1289.

Blick et al. (2004) "Nano-Electromechanical Transistor Operated as a Bi-Polar Current Switch," *Proceedings of the 4h IEEE Conference on Nanotechnology*, 258-259.

Blick et al. (2003) "A Quantum Electromechanical Device: The Electromechanical Single-Electron Pillar," *Superlatices and Microstructures* 33(5-6):397-403.

Blick et al. (1995) "Photon Assisted Tunneling Through a Quantum Dot at High Microwave Frequencies," *Appl. Phys. Lett.* 67:3924.

Blick et al. (2002) "Nanostructures Silicon for Studying Fundamental Aspects of Nanomechanics," *J. Phys: Condens. Matter* 14:R905-R945.

Brattain et al. (1953) "Surface Properties of Germainium," *Bell Syst. Tech. J.* 32:1.

Buldum et al. (Dec. 1, 2003) "Electron Field Emission Properties of Closed Carbon Nanotubes," *Phys. Rev. Lett.* 91:236801.

Cruz et al. (2005) "Field Emission Characteristics of a Tungsten Microelectromechanical System Device," *Appl. Phys. Lett.* 86(153502):1-3.

Driskill-Smith et al. (1997) "Nanoscale Field Emission Structures for Ultra-Low Voltage Operation at Atmospheric Pressure," *Appl. Phys. Lett.* 71(21):3159-3161.

Driskill-Smith (1997) "Fabrication and Behavior of Nanoscale Field Emission Structures," *J. Vac. Sci. Technol. B* 15(6):2773-2776.

Driskill-Smith et al. (1999) "The 'Nanotriode': A Nanoscale Field-Emission Tube," *Appl. Phys. Lett.* 75(18):2845-2847.

Ekinci et al. (May 31, 2004) Ultrasensitive Nanoelectromechanical Mass Detection *Appl. Phys. Lett.* 84:4469-4471.

Erbe et al. (Nov. 6, 2000) "Mechanical Mixing in Nonlinear Nanomechanical Resonators," *Appl. Phys. Lett.* 77(19):3102-3104.

Forbes et al. (Mar./Apr. 1999) "Field-Emission: New Theory for the Derivation of Emission Area from a Fowler—Nordheim Plot," *J. Vac. Sci Technol. B* 17(2):526-533.

Huang et al. (2003) "Nanoelectromechanical Systems: Nanodevice Motion at Microwave Frequencies," *Nature* 421:496.

Ilic et al. (2005) "Enumeration of DNA Molecules Bound to a Nanomechanical Oscillator," *Nano Lett.* 5(5):925-929.

Jensen et al. (Jul./Aug. 1998) "Advanced Emitters for Next Generation rf Amplifiers," *J. Vac. Sci. Technol. B* 16(4):2038-2048.

Jensen et al (Jul. 15, 1997) "Space Charge Effects on the Current-Voltage Characteristics of Gated Field Emitter Arrays," *J. Appl. Phys.* 82(2):845-854.

Kim et al. (Sep. 20, 2004) "Bonding Silicon-on-Insulator to Glass Wafers for Integrated Bio-electronic Circuits," *Appl. Phys. Lett.* 85:2370-2372.

Kirschbaum et al. (Jul. 8, 2002) "Integrating Suspended Quantum Dot Circuits for Applications in Nanomechanics," *Appl. Phys. Lett.* 81:280-282.

Konig et al. (2004) "Drastic Yield Enhancement in Nano-Mechanical Device Production by Electron Beam Deposition," *Appl. Phys. Lett.* 85:157.

Koops et al. (1996) "Conductive Dots, Wires, and Supertips for Field Electron Emitters Produced by Electron-Beam Induced Deposition on Samples Having Increased Temperature," *J. Vac. Sci. Technol. B* 14(6):4105-4109.

Kraus et al. (2000) "Nanomechanical Vibrating Wire Resonator for Phonon Spectroscopy in Liquid Helium," *Nanotechnol.* 11(3):165-168.

Molares et al. (Mar. 31, 2003) "Electrical Characterization of Electrochemically Grown Single Copper Nanowires," *Appl. Phys. Lett.* 82:2139-2141.

Nguyen, C.T.-C. (Aug. 1999) "Frequency-Selective MEMS for Miniaturized Low-Power Communication Devices," *IEEE Trans. Microwave Theory Tech.* 47(8):1486-1503.

Pescini et al. (2001) "Nanoscale Lateral Field-Emission Triode Operating at Atmospheric Pressure," *Adv. Mater.* 13(23):1780-1783.

Pescini et al. (2003) "Mechanical Gating of Coupled Nanoelectromechanical Resonators Operating at Radio Frequency," *Appl. Phys. Lett.* 82(3):352-3354.

Pescini et al. (1999) "Suspending Highly Doped Silicon-on-Insulator Wires for Applications in Nanomechanics," *Nanotechnol.* 10:418-420.

Roukes, M.L. (2001) "Nanoelectromechanical Systems Face the Future," *Phys. World* 14:25-31.

Roukes et al. (2000) "Nanoelectromechanical Systems," *Technical Digest of the 2000 Solid-State Sensor and Actuator Workshop* Hilton Head Island, SC, Jun. 4-Jun. 8, 2000, pp. 1-10.

Scheible et al. (Jun. 7, 2004) "Silicon Nanopillars for Mechanical Single-Electron Transport," *Appl. Phys. Lett.* 84:4632-4634.

Scheible et al. (2002) "Evidence of a Nanomechanical Resonator Being Driven into Chaotic Response Via the Ruelle—Takens Route," *Appl. Phys. Lett.* 81:1884.

Scheible et al. (2004) "Effects of Low Attenuation in a Nanomechanical Electron Shuttle," *J. Appl. Phys.* 96:1757.

Scheible et al. (Oct. 25, 2004) "Periodic Field Emission from an Isolated Nanoscale Electron Island," *Phys. Rev. Lett.* 93(18):186801.

Scheible et al. (2003) "Dynamic Control of Coupled Nano-Mechanical Resonators," *Appl. Phys. Lett.* 82(19):3333-3335.

Scheible et al. (2002) "Tunable Coupled Nanomechanical Resonators for Single-Electron Transport," *New J. Phys.* 4:86.1-86.7.

Schossler et al. (1997) "Nanostructured Integrated Electron Source," *J. Vac. Sci Technol. B* 16(2):862-865.

Schossler et al. (1997) "Conductive Supertips for Scanning Probe Applications," *J. Vac. Sci. Technol. B* 15(4): 1535-1538.

Smirnov et al. (2003) "Nonequilibrium Fluctuations and Decoherence in Nanomechanical Devices Coupled to the Tunnel Junction," *Phys. Rev. B* 67:115312.

Temple et al. (1998) "Silicon Field Emitter Cathodes: Fabrication, Performance, and Applications," *J. Vac. Sci. Technol. A* 16(3):1980-1990.

Tilke et al. (2003) "Fabrication and Characterization of a Suspended Silicon Nanowire for Bolometry," *App;. Phys. Lett.* 82:3773-.

Weber et al. (1995) "Electron-Beam Induced Deposition for Fabrication of Vacuum Field Emitter Devices," *J. Vac. Sci. Technol. B* 13(2):461-464.

Wong et al. (1993) "Observational of Fowler-Nordheim Tunneling at Atmospheric Pressure Using Au/Ti Lateral Tunnel Diodes," *J. Phys. D* 26:979-985.

Xu et al. (1998) "Enhancing Electron Emission from Silicon Tip Arrays by Using Thin Amorphous Diamond Coating," *Appl. Phys. Lett.* 73(25):3668-3670.

Zheng et al. (Mar. 12, 2004) "Quantum-Mechanical Investigation of Field-Emission Mechanism of a Micrometer-Long Single-Walled Carbon Nanotube," *Phys. Rev. Lett.* 92:106803.

\* cited by examiner 130
170
110

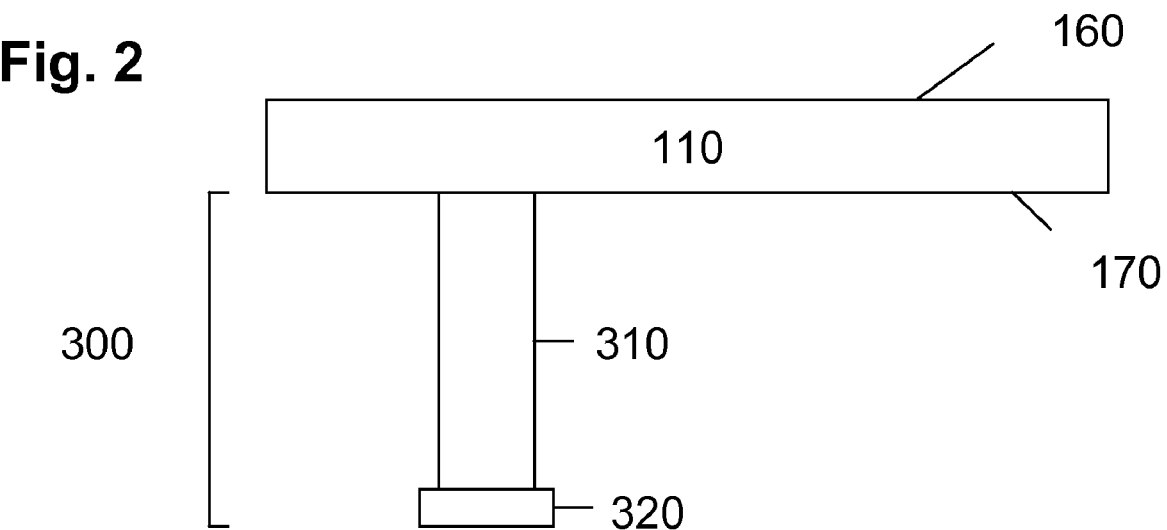

Fig. 3A    Fig. 3B    Fig. 3C
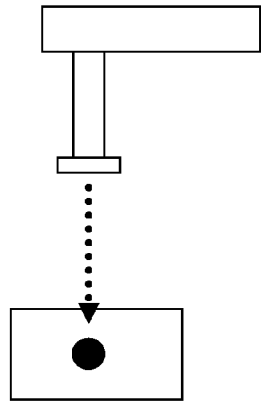 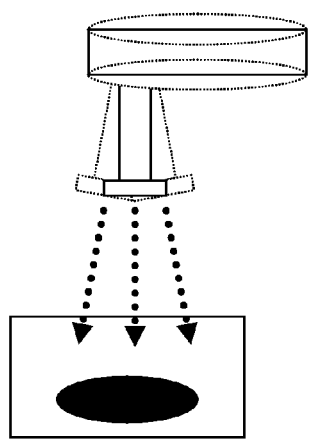 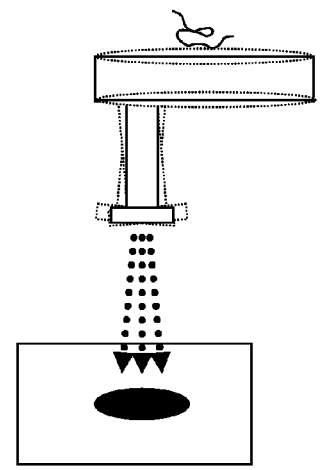
Fig. 3D    Fig. 3E
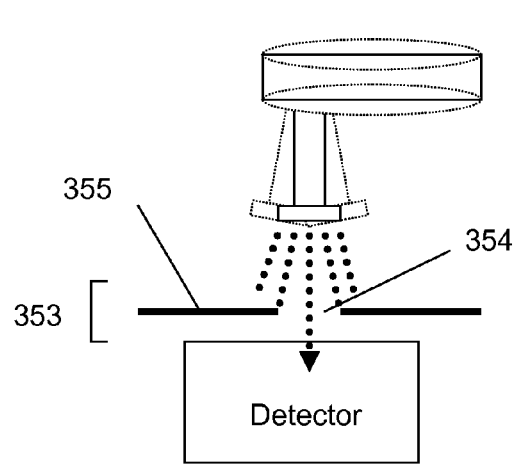 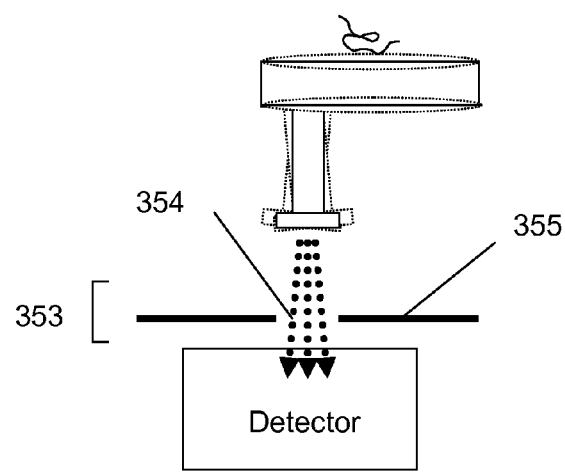
Signal = $I_{unperturbed}$    Signal = $I_{perturbed} > I_{unperturbed}$

Fig. 9
|  | 1st mode | 2nd mode | 3rd mode | 4th mode | 5th mode |
|---|---|---|---|---|---|
| Front view | 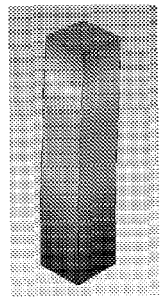 | 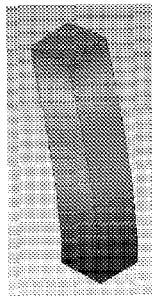 | 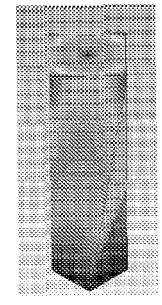 | 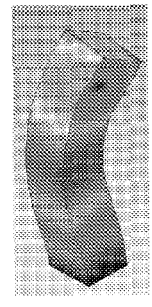 | 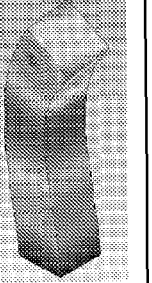 |
| Top view | 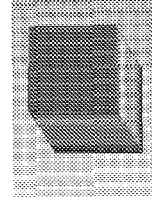 | 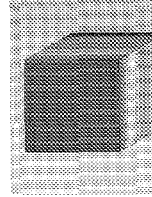 | 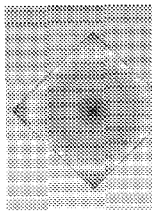 | 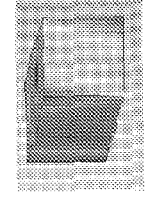 | 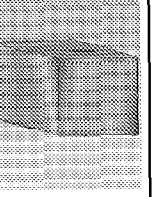 |

10a
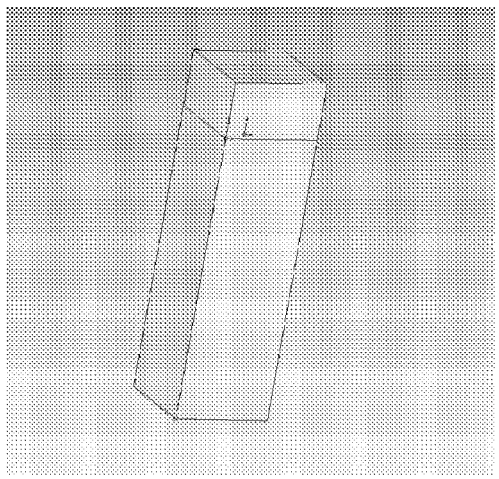
10b
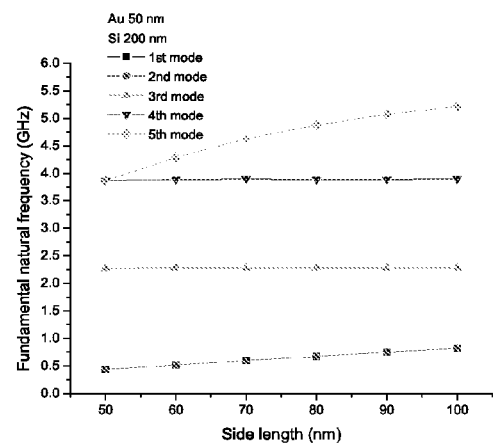
10c
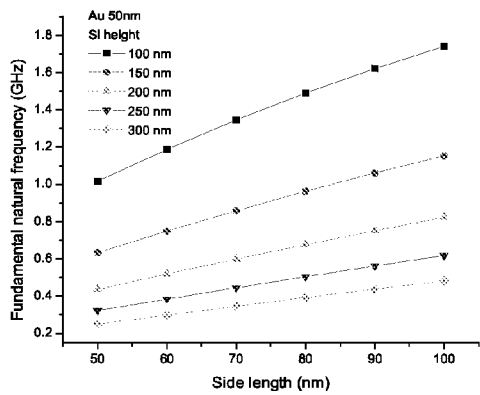
10d
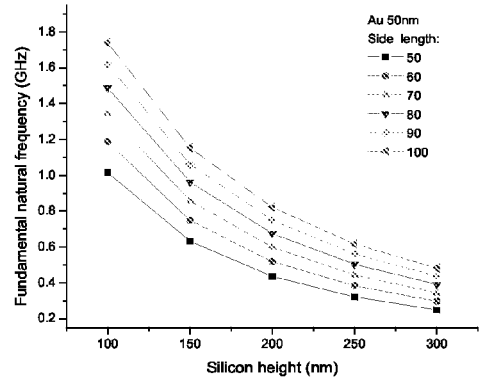
10e
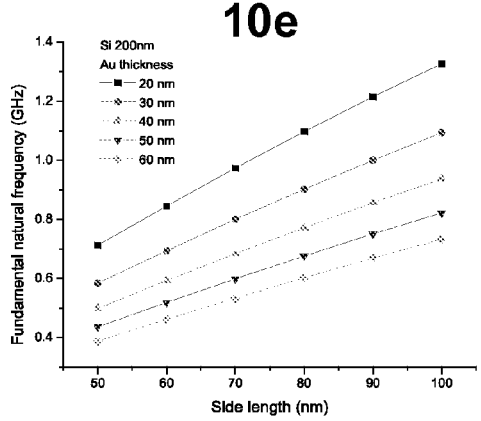
10f
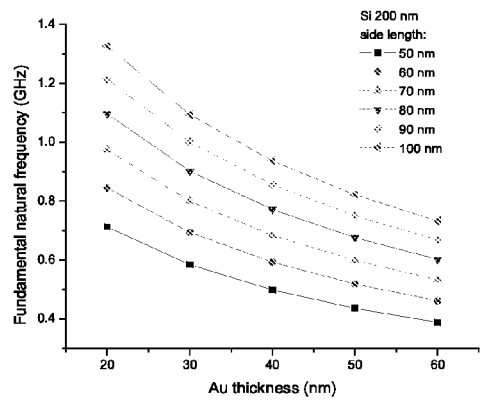
Fig. 10

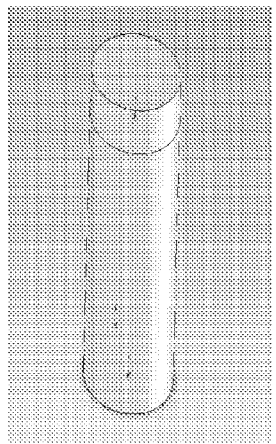
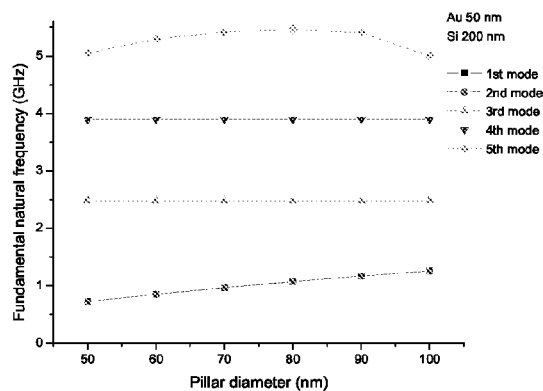
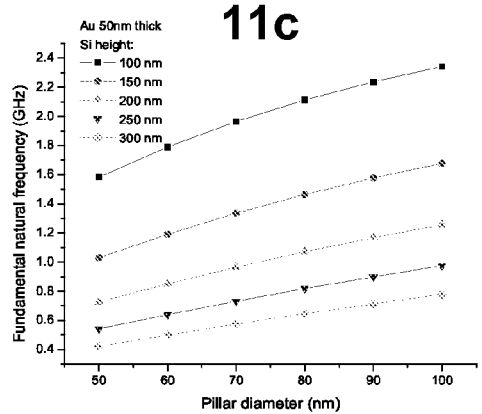
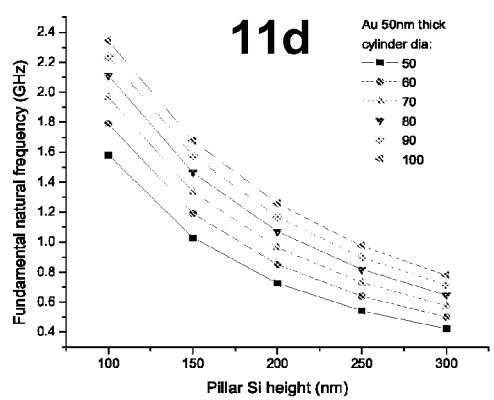
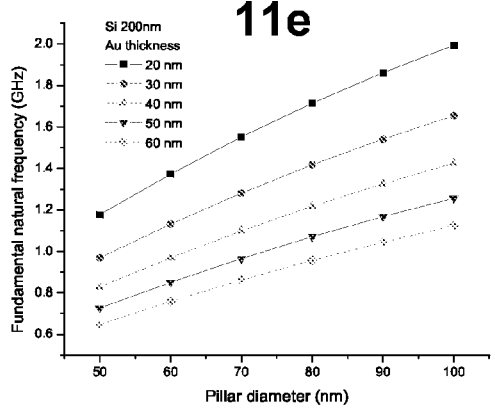
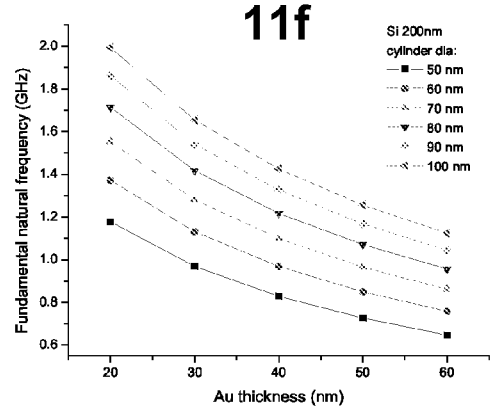
Fig. 11

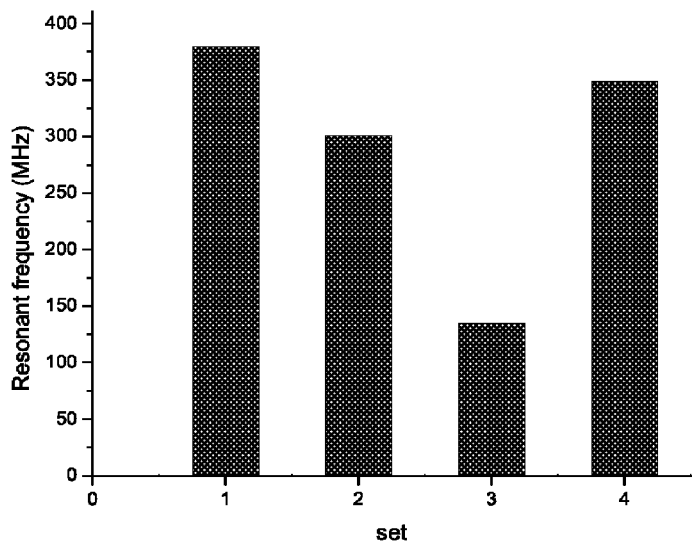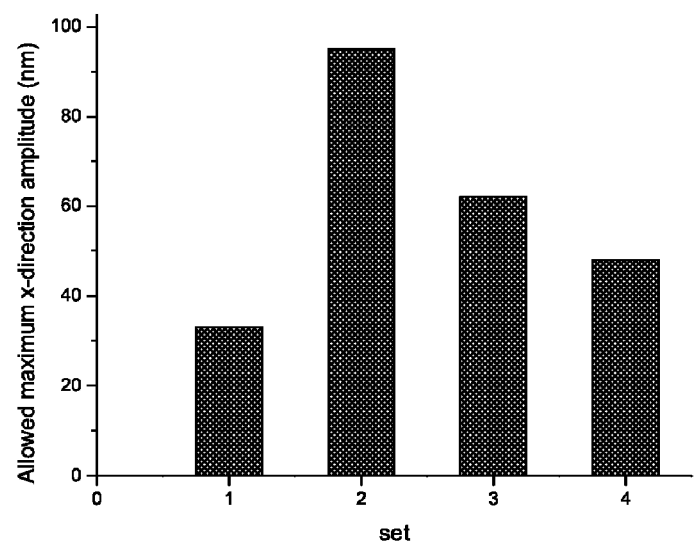
Fig. 12

Fig. 18B

| Set | 3 | 4 |
|---|---|---|
| X-direction amplitude change | | |
| X-direction phase change | | |
| Deduced Quality factor | 203 | 95 |

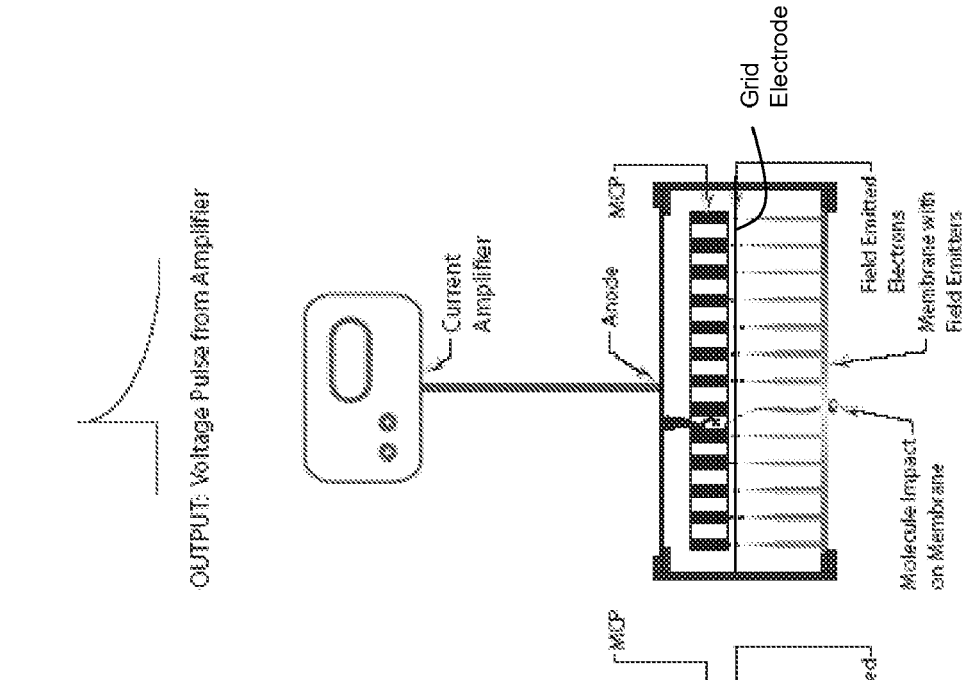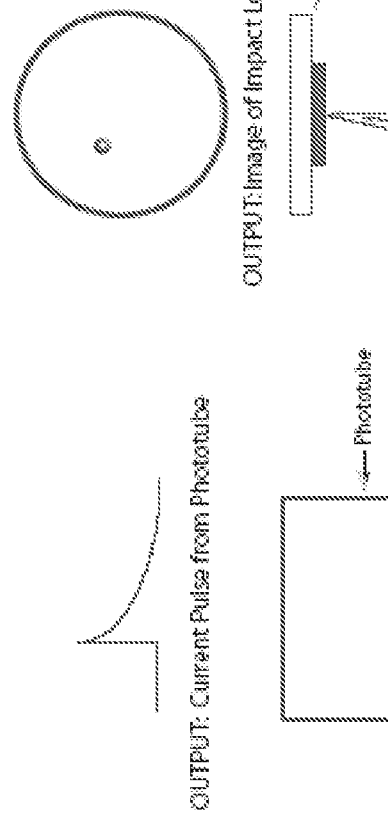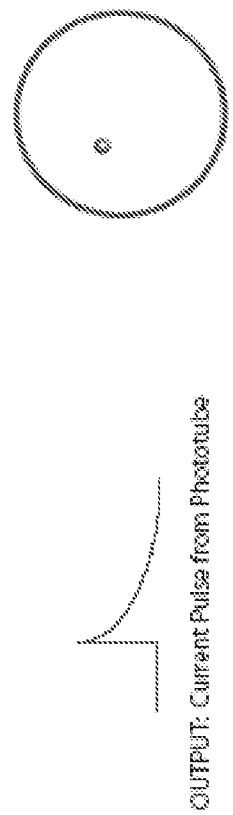

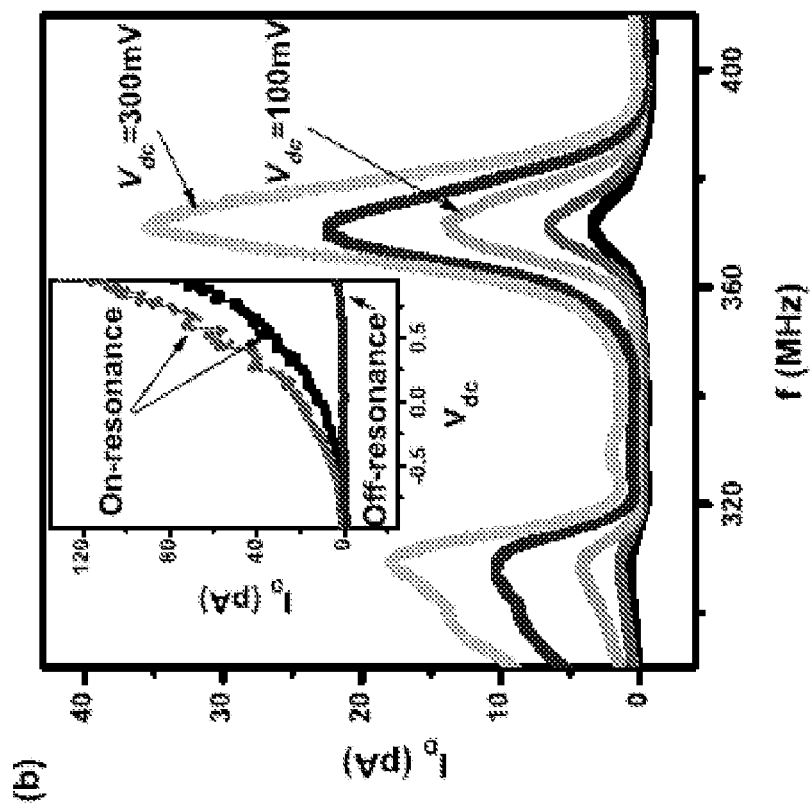
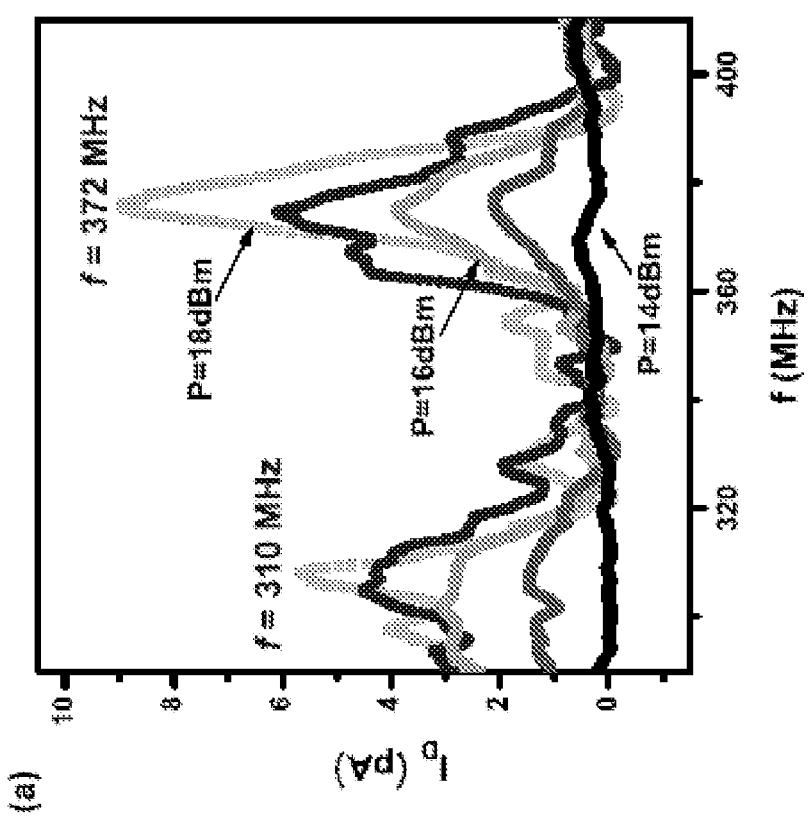
Figure 25

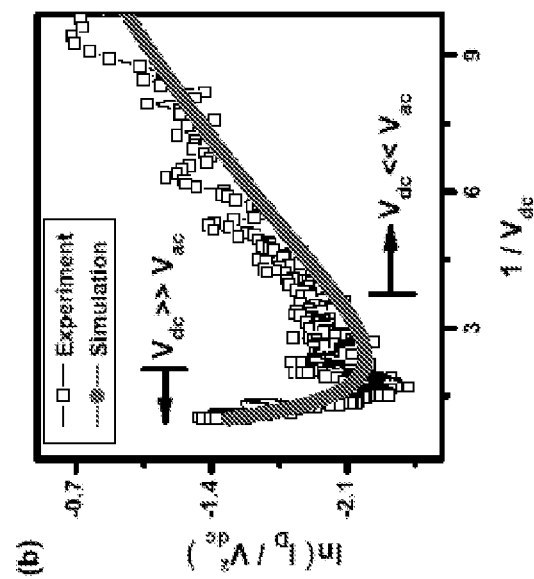
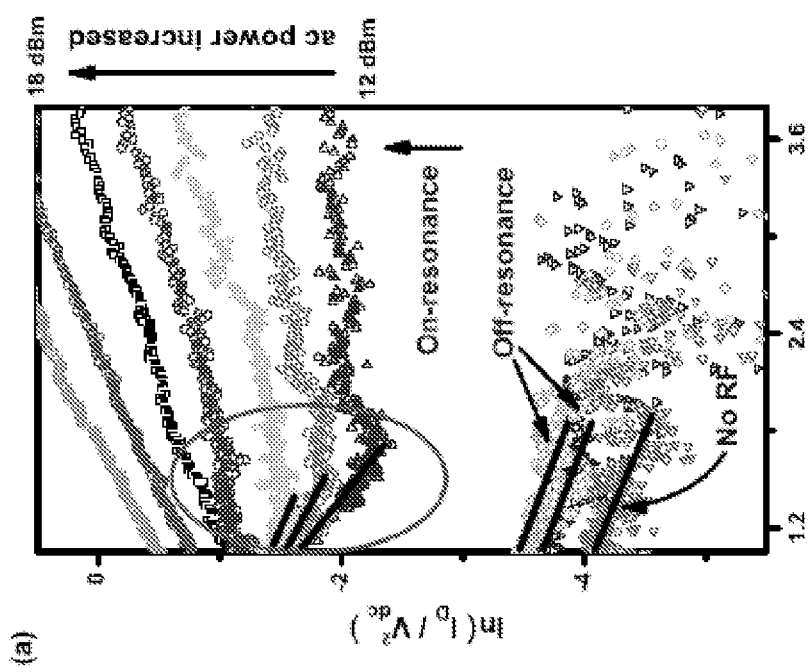
Figure 26

NANOELECTROMECHANICAL AND MICROELECTROMECHANICAL SENSORS AND ANALYZERS

CROSS REFERENCE TO RELATED APPLICATIONS

This application claims priority under 35 U.S.C. 119(e) to U.S. provisional Patent Application 60/702,938 filed Jul. 27, 2005, which is hereby incorporated by reference in its entirety.

STATEMENT REGARDING FEDERALLY SPONSORED RESEARCH OR DEVELOPMENT

This invention was made with United States governmental support awarded by the following agencies: NIH 28182. The United States has certain rights in this invention.

BACKGROUND OF INVENTION

Over the last several decades, mass spectrometry has emerged as one of the most broadly applicable analytical tools for detection and characterization of a wide class of molecules. Mass spectrometric analysis is applicable to almost any chemical species capable of forming an ion in the gas phase, and, therefore, provides perhaps the most universally applicable method of quantitative analysis. In addition, mass spectrometry is a highly selective technique especially well suited for the analysis of complex mixtures comprising a large number of different compounds in widely varying concentrations. Further, mass spectrometric analysis methods provide high detection sensitivities, approaching tenths of parts per trillion for some species. As a result of these beneficial attributes, a great deal of attention has been directed over the last several decades at developing mass spectrometric methods for analyzing complex mixtures of biomolecules, such as peptides, proteins and oligonuceotides and complexes thereof.

Mass spectrometric analysis involves three fundamental processes: (1) gas phase ion formation, (2) mass analysis whereby ions are separated on the basis of mass-to-charge ratio (m/z), and (3) detection of ions subsequent to separation. The overall efficiency of a mass spectrometer (overall efficiency=(analyte ions detected)/(analyte molecules consumed)) may be defined in terms of the efficiencies of each of these fundamental processes by the equation:

$$E_{MS}=E_F \times E_{MA} \times E_D, \quad (I)$$

where $E_{MS}$ is the overall efficiency, $E_F$ is the ion formation efficiency (ion formation efficiency=(analyte ions formed)/(analyte molecules consumed during ion formation)), $E_{MA}$ is the mass analysis efficiency (mass analysis efficiency=(analyte ions mass analyzed)/(analyte ions consumed during analysis)) and $E_D$ is the detection efficiency (detection efficiency=(analyte ions detected)/(analyte ions consumed during detection)).

Despite the fact that mass spectrometry is currently one of the most widely used techniques for identifying and characterizing biomolecules, conventional state of the art mass spectrometers have surprisingly low overall efficiencies for these compounds. For example, a quantitative evaluation of the efficiency of a conventional orthogonal injection time-of-flight mass spectrometer (Perseptive Biosystems Mariner) for the analysis of a sample containing a 10 kDa protein yields the following efficiencies, $E_S=1\times10^{-4}$, $E_{MA}=8\times10^{-7}$, and $E_D=9\times10^{-3}$, providing an overall efficiency of the mass spectrometer of 1 part in $10^{12}$. As a result of low overall efficiency, conventional mass spectrometric analysis of biomolecules typically requires large samples and is unable to achieve the ultra low sensitivity needed for many important biological applications, such as single cell analysis of protein expression and post-translational modification. Therefore, there is a significant need in the art for more efficient ion preparation, analysis and detection techniques to capture the full benefit of mass spectrometric analysis for important biological applications.

Over the last decade, new ion preparation methods have revolutionized mass spectrometric analysis of biological molecules. These new ionization methods, which include matrix assisted laser desorption and ionization (MALDI) and electrospray ionization (ESI), provide greatly improved ionization efficiency for a wide range of compounds having molecular weights up to several hundred kiloDaltons. Moreover, MALDI and ESI ionization sources have been successfully integrated with a wide range of mass analyzers, including quadrupole mass analyzers, time-of-flight instrumentation, magnetic sector analyzers, Fourier transform—ion cyclotron resonance instruments and ion traps, to provide selective identification of polypeptides and oligonucleotides in complex mixtures. Mass determination by time-of-flight (TOF) analysis has proven especially well suited for the high molecular weight biomolecules ionized by ESI and MALDI techniques because TOF has no intrinsic limit to the mass range accessible, provides high spectral resolution and has fast temporal response times. Use of time-of-flight mass analysis with ESI and MALDI ion sources for proteomic analysis is described in detail by Yates in Mass Spectrometry and the Age of the Proteome, Journal of Mass Spectrometry, Vol. 33, 1-19 (1998). As a result of these advances, MALDI-TOF and ESI-TOF have emerged as the two most commonly used ionization techniques for analyzing complex mixtures of biomolecules having high molecular weights.

Although integration of modern ionization techniques and time-of-flight analysis methods has greatly expanded the mass range accessible by mass spectrometric methods, complementary ion detection methods suitable for time of flight analysis of high molecular weight compounds, including many biological molecules, remain considerably less well developed. Indeed, the effective upper limit of mass ranges currently accessible by MALDI-TOF and ESI-TOF analysis techniques are limited by the sensitivity of conventional ion detectors for high molecular weight ions. For example, conventional multichannel plate (MCP) detectors exhibit detection sensitivities that decrease significantly with ion velocity, which corresponds to a decrease in sensitivity with increasing molecular weight when these detectors are used for TOF mass analysis.

MCP detectors are perhaps the most pervasive ion detector used in ESI-TOF and MALDI-TOF mass spectrometry. These detectors operate by secondary electron emission and typically comprise a parallel array of miniature channel electron multipliers. Typically the channel diameters are in the range of 10 to 100 microns with the lengths of the channels in the neighborhood of 1 mm. Each channel operates as a continuous dynode structure, meaning that it acts as its own dynode resistor chain. A potential of about 1 to 2 kV is placed across each channel. When an energetic molecule enters the low potential end of the channel and strikes the wall of the channel it produces secondary electrons which are in turn accelerated along the tube by the electric field. These electrons then strike the wall generating more electrons. The process repeats many times until the secondary electrons emerge from the high potential end of the channel. Generally speaking for each molecule which initiates a cascade, $10^4$ electrons emerge from the channel providing significant gain. The electron cascade formed is collected at an anode and generates an output signal. MCP detectors can be made in large area format which is useful for analysis of packets of ions in TOF systems.

A number of substantial limitations of this detection technique arise out of the impact-induced mechanism of MCP detectors governing secondary electron generation. First, the yield of secondary electrons in a MCP detector decreases significantly as the velocities of ions colliding with the surface decreases. As time-of-flight detectors accelerate all ions to a fixed kinetic energy, high molecular weight ions have lower velocities and, hence, lower probabilities of being detected by MCP detectors. Second, the secondary electron yield of MCP detectors also depends on the composition and structure of colliding gas phase ions. Third, it is also well established that once a cascade has been initiated within a channel, it is depleted of electrons. Due to the high resistivity of the channel, the time required to replace these electrons is several orders of magnitude larger (milliseconds) than the duration of the TOF measurement (microseconds). Thus, for a single TOF event a channel is rendered inactive after a single cascading event, thus each successive packet of ions impinging on the detector has fewer and fewer active channels available to it.

As is apparent to those skilled in the art of mass spectrometry, the limitations associated with MCP detectors restrict the mass range currently accessible by MALDI-TOF and ESI TOF techniques, and hinder the quantitative analysis of samples comprising complex mixtures of high molecular weight biopolymers. Accordingly, there currently exists a need for ion detectors that do not exhibit decreasing sensitivities with increasing molecular weight and that do not have sensitivities dependent on the composition and structure of gas phase ions analyzed.

Over the last decade, considerable research has been directed at developing new sensors based on nanoelectromechanical resonators that are suitable for detecting and analyzing high molecular weight compounds. U.S. Pat. No. 6,722,200, for example, describes mass analyzers for use in mass spectrometry analysis comprising an array of nanoelectromechanical beam resonators. In these systems, the fundamental mode resonance frequencies of a plurality of double-clamped nanoelectromechanical beam resonators are monitored in time using a phase-locked loop circuit. The surfaces of the beam resonators are positioned to intersect the path of a stream of gas phase molecules to be detected. Collisions between the molecules and the surface of a beam resonator results in accommodation which in turn provides a measurable change of the resonance frequency of the resonator. The measured change in resonance frequency is reported to be related to the mass of the molecule(s) received by the resonator and, hence continuously monitoring the resonance frequencies of resonators in the array provides a means of detecting and analyzing molecules.

Although the sensor designs disclosed in U.S. Pat. No. 6,722,200 are reported to provide a sensitive means of detecting and analyzing molecules, particularly high molecular weight molecules, this technique is susceptible to a number of drawbacks that make its integration with conventional mass spectrometry systems impractical. First, 10s of thousands of resonators are needed to provide a detector with a large enough active area for use in a conventional TOF mass spectrometer. Individually reading out each resonator in such a large array is expected to take a very long time and thus, these sensors are not likely to provide a temporal response time useful for most mass spectrometry systems, such as TOF analyzers. Further, such a readout system is expected to be cumbersome (difficult to house in a compact fashion) and cost prohibitive for commercial development. Second, the measured change in resonance frequency is expected to depend significantly on the exact location on the resonator where contact is established with the molecule(s) undergoing detection/analysis. This dependency is likely to result in significant variations in detection sensitivity and mass resolution as a function of where the molecule contacts the resonator. Finally, removal of the molecule after detection to ready the device for another detection event requires post detection processing, such as elevating the temperature, providing electromagnetic radiation and/or treatment by other thermal means. These processes are expected to materially change the physical dimensions and composition of resonators in the array, particularly given their incredible small physical dimensions. Therefore, these post detection processes are likely to undermine the performance reliability of these devices with respect to sensitivity and resolution.

It will be appreciated from the foregoing that there is currently a need in the art for methods, systems and devices for detecting and analyzing molecules having large molecular masses. Specifically, detection methods and systems providing sensitive detection of large molecular mass molecules are needed that are capable of effective integration with conventional mass spectrometry systems, such as TOF analysis systems. Sensors and analyzers are needed for mass spectrometry applications that do not exhibit deceases in sensitivity as a function of molecular mass, and that are capable of fast readout and good temporal resolution.

SUMMARY OF THE INVENTION

The present invention provides methods, devices and device components for detecting, sensing and analyzing molecules. Detectors of the present invention provide good detection sensitivity over a wide range of molecular masses ranging from a few Daltons up to 10s of megadaltons, which does not decrease as function of molecular mass. Sensors and analyzers of the present invention detect emission from an array of resonators to determine the molecular masses and/or electric charges of molecules which impact or contact an external surface of a membrane that is used to mount and excite the resonators in the array. Resonators in the array are excited via piezoelectric and/or magnetic excitation of the mounting membrane and, optionally, grid electrodes are used in certain configurations for electrically biasing for the resonator array, and for amplification or suppression of emission from the resonators so as to provide detection and mass/electric charge analysis with good sensitivity and resolution.

Methods, devices and device components of the present invention provide a means for detecting single molecules or packets of molecules with good temporal resolution, and therefore, are particularly well suited for use in mass spectrometry analysis methods including time-of-flight mass spectrometry, environmental sensing and liquid phase assay applications, including flow-through liquid phase probe systems for identifying and characterizing interactions of biological molecules. Detectors, sensors and analyzers of the present invention are capable of detecting molecules in a range of chemical and physical environments, including low and high pressure environments, and including gas, liquid and solution phases.

In one aspect, the present invention provides a sensor for detecting one or more molecules, determining the molecular masses of one or more molecules and/or determining the electric charge of one or more molecules. In one embodiment, a sensor of the present invention comprises a membrane, a means for vibrating the membrane, a plurality of electromechanical resonators (such as an array of electromechanical resonators) and a detector. The membrane is provided with a receiving surface for receiving the molecule(s) undergoing detection and/or analysis and an inner surface positioned opposite to the receiving surface. The means for vibrating the membrane is mechanically, acoustically and/or electrically coupled to the membrane such that it is capable of setting and maintaining the membrane in motion, such as periodic vibrational motion. In one embodiment, for example, the membrane and means for vibrating the membrane are coupled in a manner capable of establishing and maintaining a surface acoustic wave on the inner surface, receiving surface or both of the membrane.

Electromechanical resonators are positioned to extend vertically from the inner surface of the membrane along a plurality of axes that intersect the inner surface. Resonators and the membrane are mechanically coupled such that vibration of the membrane causes the resonators to resonate at selected resonance frequencies. Mechanical coupling of the membrane and the resonators may be provided by direct physical contact or via a connecting device component, layer or material. In one embodiment, for example, vibration of the membrane causes the resonators to oscillate via selected vibrational mechanical modes, rotational mechanical modes, counter-rotational mechanical modes, flexural modes or any combination of these motions. Resonators useful in this aspect of the present invention include nanoelectromechanical resonators, microelectromechanical resonators or a combination of both nanoelectromechanical resonators and microelectromechnical resonators. Optionally, resonators and the membrane are electrically coupled such that an electric potential applied to the membrane may be used to electrically bias or gate the resonators mechanically coupled to its inner surface. The resonators may be D.C. biased in this fashion or may be operated in AC mode.

Electromechanical resonators of this embodiment of the present invention comprise emissive elements that are capable of generating emission, such as generating free electrons and/or electromagnetic radiation. Field emission may be initiated by electrically and/or mechanically biasing the resonators, for example by biasing through the membrane, or by electrically biasing provided by a grid electrode positioned between the inner surface of the membrane and the detector. In one embodiment useful for providing a sensor for determining molecular masses, for example, electromechanical resonators comprise emissive elements that continuously generate emission characterized by a spatial distribution. In the context of this description, the spatial distribution of emission from resonators refers to the angular distribution of propagation or transmission axes of emission originating from one or more resonators. In the present invention spatial distribution of emission can be monitored and/or measured by any means known in the art. In one embodiment, for example, the spatial distribution of emission from one or more resonators is monitored and/or measured by measuring the area of a hypothetical plane positioned a selected distance from the inner surface of the membrane that interacts with emission during a selected time interval (commonly referred to as the spot size), for example a time interval corresponding to one or more complete oscillation cycles of one or more resonators.

In another aspect, sensors of the present invention are capable of monitoring changes in the spatial distribution of emission from at least a portion of the resonators mechanically coupled to the membrane inner surface. Sensors of this aspect of the invention are particularly useful as detectors for time-of-flight mass analyzers because they are capable of providing sensitive detection with very good temporal resolution. In one embodiment of this aspect of the present invention, a plurality of resonators mechanically coupled to the membrane are electrically biased and/or mechanically biased such that they only generate emission upon undergoing a change in resonance frequency caused by interaction of a molecule and the receiving surface. In this embodiment, detection of changes in emission intensity and/or energy provides a means of sensing changes in the spatial distribution of emission from the resonators caused by interaction of a molecule with the receiving surface. In another embodiment of this aspect of the present invention, a partially transmissive grid electrode is provided between the inner surface of the membrane and the sensing surface of a detector. In this embodiment changes in the resonance frequencies of resonators results in a change in the intensity and/or power of emission that is transmitted by the grid electrode. Detection of changes in emission intensity and/or power in this embodiment, therefore, provides a means of detecting changes in the spatial distribution of emission from at least a portion of the resonators caused by interaction of a molecule with the receiving surface. In another embodiment of this aspect of the present invention, resonators are electrically and/or mechanically biased such that they continuously generate emission which is detected by a multichannel plate (MCP) detector. The open areas and closed areas of the MCP detector are aligned with respect to the position of resonators on the membrane inner surface such that changes in the resonance frequencies of resonators results in a measurable change in current generated by the MCP detector.

In the present invention, the spatial distribution of emission generated by the resonators depends strongly on the vibrational or rotational state of each resonator mechanically coupled to the inner surface of the membrane (i.e. depends on both on the mechanical modes and the resonance frequencies of the resonators). Resonators exhibiting a spectrally pure frequency response curve provide sensors having a good detection sensitivity and mass resolution because changes in the spatial distribution of emission from the resonators having a spectrally pure frequency response curve are more easily identified and quantitative characterized.

The detector is positioned such that it receives and detects emission from the resonator. In one useful embodiment, for example, the detector is capable of detecting and/or characterizing changes in the spatial distribution of the emission from the resonators. In one embodiment, for example, the detector comprises a sensing surface positioned a selected distance from the inner surface of the membrane that is capable of measuring the area of the sensing surface that interacts with emission from the resonators. Preferably for some applications, the detector is capable of detecting and/or quantitatively characterizing changes in the spatial distribution of emission occurring on very fast time scales, such as changes occurring on time scales less than or equal to about 1 to about 10 nanoseconds. Optionally, the sensor further comprises a grid electrode held at a selected electric potential positioned between the inner surface of the membrane and the detector that is capable of electrically biasing resonators mechanically coupled to the inner surface of the membrane. Grid electrodes useful in some, but not all, embodiments of the present invention preferably do not significantly change the spatial distribution or intensity of emission from the resonators mechanically coupled to the inner surface of the membrane.

Optionally, the sensor may further comprise a means of releasing the molecule(s) from the receiving surface of the membrane after detection and/or analysis. For example, the present invention includes means of generating a pulse of thermal energy, pulse of electromagnetic radiation, and/or pulse of electric current on the receiving surface of the membrane that is capable of releasing the molecule from the receiving surface.

In one embodiment, sensors of this aspect of the invention are capable of detecting molecules, including the detection of single molecules and packets of molecules. In this aspect of the present invention, contact between the receiving surface of the membrane and one or more molecules undergoing analysis changes the resonance frequency of at least one resonator mechanically coupled to the inner surface of the membrane, and preferably for some applications changes the resonance frequencies of a plurality of resonators. In some useful embodiments, the resonance frequencies of resonators positioned opposite to the point(s) of contact between the molecule(s) and the receiving surface are altered, thus, generating a measurable change in the spatial distribution of emission. It is important to note that in this embodiment of the present invention resonators are mechanically coupled to the inner surface of the membrane (as opposed to the receiving surface) such that they are entirely shielded from making direct physical contact with the molecules undergoing analysis. In one embodiment, the resonance frequency of at least one resonator decreases upon contact of the molecule and the receiving surface, for example decreasing by a factor of about 1% to about 10%. The change in the resonance frequency of a resonator changes the range of positions sampled by the resonator during subsequent oscillation cycles, thereby resulting in a detectable change the spatial distribution of the emission of the resonators and/or resonator array. Detection of this change in spatial distribution provides a sensitive means of detecting the molecule(s) interacting with the receiving surface.

In another embodiment, sensors of this aspect of the invention are capable of determining the molecular masses of molecules, including determining the molecular masses of single molecules and packets of molecules. In this embodiment, a detector is provided that is capable of measuring the extent of changes in spatial distribution of emission (e.g. the percentage decrease or increase in the spatial distribution) as a function of time. Useful detectors for this application of the present invention include detectors having a detection surface capable of measuring the area of the detection surface that interacts with emission from the resonators. Under some experimental conditions, for example, the observed decrease in the spatial distribution of emission caused by interaction of a molecule and the receiving surface is directly proportional to the molecular mass of the molecules or packet of molecules contacting the detection surface. Therefore, mass analysis may be provided in this embodiment by calibrating the observed degree of attenuation of the spatial distribution of emission as a function of the mass of molecules contacted with the receiving surface.

In one aspect of the present invention, interaction of molecules with the receiving surface results in a time dependent perturbation of the resonance frequency of one or more resonators mechanically coupled to the inner surface of the membrane. The time dependence of the perturbation is typically characterized by a rapid change in resonance frequency followed by relaxation back to the unperturbed state occurring on a slower timescale. In some embodiments, the return to the unperturbed state is characterized by a relaxation time scale on the order of microseconds and may be characterized by a substantially exponential decay. The time dependence of the perturbation in the resonance frequency results in a change in the spatial distribution of emission having a similar time dependence, which in some embodiments is monitored directly to provide detection, mass analysis and/or charge analysis.

In another embodiment, sensors of this aspect of the invention are capable of determining the electric charge of molecules, including measuring the electric charge of single molecules and packets of molecules. In this embodiment, resonators are provided which generate emission characterized by an intensity and/or emissive flux (i.e. the number of photons or electrons emitted per square centimeter per unit time) that depends on the electric charge of molecules interacting with the receiving surface, for example resonators comprising integrated single electron tunneling transistors or high electron mobility transistors. In this aspect of the present invention, a detector is provided that is capable of quantifying the intensity or emissive flux of emission from the resonators and/or resonator array, as a function of time, and measured changes in the intensity of emission are used to determine the electric charge of molecules in contact with the receiving surface.

Use of an inverted membrane—resonator geometry comprising plurality of resonators mechanically, acoustically and/or electrically coupled to the inner surface of a membrane provides several important functional benefits in the devices and methods of the present invention. First, this geometry enables sensitive detectors having large active areas (e.g. up to about 30 $cm^2$). In the context of this discussion, the "active area" refers to the area of a receiving surface of a detector that is capable of detecting and/or sensing molecules. Detectors having large active areas are useful for detecting and analyzing analyte molecules provided in positions that vary significantly, for example for detection of gas phase analytes in mass spectrometry or detection of liquid phase analytes in a flow-through liquid phase probe system. Second, the inverted membrane—resonator geometry provides a mechanically straightforward, fast and low cost means of reading out changes in the resonance frequencies of a very large number of nanoelectromechanical or microelectromechanical resonators (e.g. more than 1000). This feature of the present invention provides a significant improvement over conventional nanoelectromechanical detector array geometries wherein a large number of individual resonator elements are read out individually. For example, the present detector geometry allows changes in the resonance frequencies of an array comprising of $10^4$ to $10^5$ individual resonators to be evaluated on a time scale equal to or less than about 1-10 nanoseconds. This feature of the present invention is particularly useful for measurements requiring good temporal resolution, for example in detectors for time-of-flight analysis where the resolution attained is directly related to the temporal resolution provided by the detector. Third, physical separation of the receiving surface and the resonators allows the receiving surface to be effectively functionalized or derivatized to provide enhanced and/or selective adsorption and desorption of selected analytes without significantly affecting the fundamental resonance frequencies and mechanical mode structure of the resonators. Further, this membrane geometry isolates the resonators from the analytes themselves and the carrier medium in which analytes are provided, while at the same time allowing for selective electrical biasing of the resonators via application of an electric potential to the membrane. Therefore, resonators of the present invention may be maintained at relatively low pressures (e.g. <about 10 Torr) useful for achieving and maintaining reproducible mechanical mode structure, while the receiving surface is provided in contact with analytes present at higher pressures, or provided in contact with liquid or solution phases. This attribute provides highly versatile detectors and analyzers for sensing applications in a wide variety of physical and chemical settings. Furthermore, the inverted membrane—resonator geometry isolates the resonators from the analyte molecules themselves avoids problems in conventional nanoelectromechanical mass sensors arising from significant variation of overall detection sensitivity and resolution with the orientation and/or position of the analyte interacting directly with the resonator.

In one embodiment of this aspect of the present invention, resonators mechanically coupled to the inner surface of the membrane comprise an array of pillar resonators, such as nanopillar and/or micropillar resonators, having vertical lengths extending from said inner surface of the membrane along axes that intersect the inner surface. Vibration of the membrane causes the pillar resonators to vibrate laterally with respect to their vertical lengths such that the ends of the pillar resonators positioned distal to the inner surface of the membrane move along substantially accurate, circular, or ellipsoidal trajectories. Detectors and sensors of the present invention having resonators comprising arrays of nanopillar and/or micropillar resonators are beneficial for some applications because they are capable of undergoing substantially periodic oscillations characterized by well defined and reproducible mechanical mode structure upon vibration of the membrane. In one embodiment, for example, vibration of the membrane causes the pillar resonators to vibrate with reproducible fundamental lateral vibrational modes having resonant frequencies accurately selected over the range of about 1 MHz to about 10 GHz. Maintaining the resonators at a constant pressure, and preferably for some sensing applications at relative low pressures (e.g. less than about 10-100 Torr), is beneficial for providing a reproducible mechanical mode structure and resonance frequencies useful for sensitive and high resolution detection and sensing applications.

In the present invention, selection of the physical dimensions, composition and physical properties of pillar resonators at least in part establishes their mechanical mode structure and resonance frequencies, which in turn affects the overall sensitivity and resolution of detectors and sensors of the present invention. Use of pillars having vertical lengths selected over the range of about 100 nanometers to about 3 microns and average cross sectional dimensions (e.g., diameter, radius, width, thickness, etc.) selected over the range of about 10 nanometers to about 500 nanometers are preferred for applications requiring high sensitivity and mass resolution. In some embodiments, the mass resolution of a sensor of the present invention is increased by use of pillar resonators having large aspect ratios (i.e. decreased the cross sectional dimensions and increased vertical lengths), for example an aspect ratio equal to or greater than about 5:1. In one embodiment providing high mass resolution, the pillar resonators comprise metal nanotubes or semiconductor nanotubes, such as carbon nanotubes, having diameters selected over the range of about 1 nanometer to about 10 nanometers. Pillar resonators may further comprise resonant tunneling diodes (RTD) having good IV-characteristics and are easily integrated in many pillar configurations. Use of RTD diode integrated resonators is particularly useful for charge sensing applications and controlling the electron flux of resonators.

Pillar resonators useable in this aspect of the present invention may have any cross sectional shape providing reproducible vibrational, rotational and/or counter rotation mechanical oscillations having selected resonance frequencies. Exemplary cross sectional pillar shapes including circular, square, rectangular, triangular, polygonal, and ellipsoidal or any portion or combination of these cross sectional shapes. Cross sectional dimensions and shapes of nanopillars and micropillars may be substantially constant (within 10%) as a function of their vertical lengths or may vary systematically as a function of their vertical lengths. In one embodiment providing good detection sensitivity, for example, the cross sectional dimensions vary systematically with vertical length so as to form a waist in the pillar resonator having reduced cross sectional dimensions. Pillar resonators of this embodiment have a greater distribution of mass on the top of the pillar (end distal to the inner surface of the membrane) which gives rise to larger physical displacement when excited by vibration of the membrane.

Pillar resonators of this aspect of the present invention may have any composition providing well defined and reproducible mechanical mode structure and resonance frequencies selected with high accuracy. For example, pillars comprising a material, such as a semiconductor, polymer, metal or ceramic material, having a Young's modulus selected from the range of about 500 MPa to about 500 GPa are beneficial for some applications of the present invention. The composition of pillar resonators in the present invention is also selected so as to provide stable emission characteristics and emission intensities for accurate detection and characterization of the spatial distribution of emission from resonators. Exemplary pillar resonators comprise semiconductor containing heterogeneous structures, including a plurality of semiconductor, dielectric and/or metal layers in electrical and/or physical contact with each other.

The present invention includes sensor configurations having a plurality of field emitting pillar resonators, such as field emitting pillar resonators comprising one or more semiconductor layers, such as a semiconductor base, in electrical contact with the inner surface of the membrane. The present invention also includes membranes, nanoelectromechanical resonators, and microelectromechanical resonators comprising extremely piezoelectric materials such as SrTiO. Semiconductor layers may be provided with one or more dopants having selected dopant levels and/or dopant spatial distributions. Doping the semiconductor base of a resonator is also useful for tuning the intensity of emitted electrons, for example to provide intensities large enough to generate measurable changes in the spatial distribution of emission upon interaction of a molecule(s) with the receiving surface. The present invention also includes field emitting heterostructure pillar resonators comprising a plurality of layers of different composition, such as a plurality of semiconductor layers, conducting layers and/or dielectric layers. In one embodiment, for example, field emitting pillars are provided that comprise a semiconductor base having a first end mechanically and/or electrically coupled to the inner surface of the membrane and a second end distal to the inner surface of the membrane that is in electrical contact with a metal layer field emitting tip. In this embodiment, integration of the metal layer field emitting tip is useful for lowering the work function for field emission. In another embodiment, field emitting pillar resonators of the present invention comprise a multilayer structure that integrates one or more single electron device, such as a single electron tunneling transistor. Pillars of this embodiment, for example, may comprise a multilayer structure having a Coulomb Island bounded by tunneling barriers, such as thin dielectric layers or conductance constriction nanowire segments. The integrated single electron tunneling transistor functions as a valve for migration of electrons to the tips of the pillar where emission occurs. The rate of migration of electrons through the single electron tunneling transistor (i.e. the electrical conductivity or resistance of the transistor) and, hence, intensity of field emission observed, is dependent on the electrical charge variation of its environment. By measuring the modulation of the field emission intensity caused by the electric charge of molecules interacting with the receiving surface of the membrane (e.g., accommodation of the molecule(s) by the receiving surface), sensors of this embodiment provide a means of measuring electric charge, optionally in addition to molecular mass.

The present invention includes sensor configurations having a plurality of photoemissive pillar resonators. In one embodiment, each pillar comprises an optically active semiconductor heterostructure, such as a surface emitting light emitting diode, P-N junction or vertical cavity surface emitting laser (VCSEL) including quantum dot lasers. Exemplary materials for optically active semiconductor heterostructures useful in the present methods and devices include Ga, As, Al and polymer materials. Use of pillar resonators comprising laser structures, such as VCSEL, is beneficial because their well defined frequency spectrum can be exploited for enhancing information density, thereby providing more accurate mass sensing. In one embodiment, for example, the frequency of electromagnetic radiation generated by the VCSEL resonators varies systematically with the momentum transfer of the molecule interacting with the receiving surface of the membrane. This configuration provides a quantum limited mass detector of the molecule(s) interacting with the receiving surface.

Pillar resonator arrays useful in the present methods include pillar resonator arrays comprising a plurality of pillar resonators having substantially the same physical dimensions and resonance frequencies, and also include pillar resonator arrays comprising plurality of pillar resonators, at least a portion of which having different physical dimensions and resonance frequencies. Use of pillar resonator arrays comprising pillars with different physical dimensions and resonance frequencies is beneficial for providing versatile detectors capable of detecting and/or determining the molecular masses of molecules having a wide range of molecular masses. Exemplary pillar resonator arrays useful in the present methods and devices comprise about $10^4$ to about $10^5$ individual pillar resonators wherein individual pillars are separated from each other by distances selected over the range of about 100 nanometers to about 10 microns. Pillar resonator densities selected over the range of about $10^4$ pillars $cm^{-2}$ to about $10^8$ pillars $cm^{-2}$ are preferred for some applications. Preferably for some applications of the present invention, pillar resonators are separate from each by a distance large enough that the motions of pillar resonators do not significantly impact the mechanical mode structure and resonance frequencies of adjacent pillar resonators comprising the array.

The spatial distribution of resonators in resonator arrays of the present invention is selected to provide useful functional attributes of the sensors and analyzers of the present invention. Pillar resonators in resonator arrays of the present invention may be symmetrically or asymmetrically distributed on the inner surface of the membrane. In one embodiment, pillar resonators in a symmetrical resonator array are provided in positions equally spaced from adjacent resonators so as to provide a detection sensitivity and mass resolution that does not vary significantly with the point of the receiving surface wherein a molecule under analysis/detection interacts. In another embodiment, the membrane is divided into grids comprising between $10^3$ to $10^4$ grid elements, and at least one pillar resonator is addressed to the region of the inner surface corresponding to each grid element. In one embodiment, for example, a series of pillar resonators each having different physical dimensions (i.e. vertical lengths and cross sectional dimensions) and/or compositions are provided on the inner surface opposite to each grid element of the membrane. This embodiment of the present invention is useful for providing detectors, sensors and analyzers responsive to molecules having a substantial range of molecular masses because resonators having different dimensions and/or compositions change resonance frequencies upon interaction of molecules having different molecular masses with the membrane. In one embodiment, the membrane has an active area in the range of about 25 $mm^2$ to 15 $cm^2$ and is divided into a plurality of grid elements each having an area of about 10-100 $micron^2$. In this embodiment, at least four pillar resonators having different vertical lengths are addressed to each grid element. The vertical lengths of the pillar resonators provided in this embodiment are selected to make each pillar resonator responsive to a range of molecules having different molecular masses. In one embodiment, the sensor has an inner surface having a pattern comprising a plurality of grid elements, wherein the number of grid elements is selected from the range of about 2 grid elements to about 1000 grid elements. In one embodiment, each grid element has an area selected over the range of about 500 $nanometers^2$ to about 500 $microns^2$. In one embodiment, about 1 to about $1 \times 10^3$ resonators are addressed to the inner surface of the membrane corresponding to each grid element.

In the present invention, the physical dimensions, composition and physical properties of the membrane are selected so that it can be vibrated in a manner that drives selected mechanical oscillations of resonators coupled to its inner surface. For example, membranes of the present invention may have compositions and physical properties capable of generating useful resonator mechanical mode structure and resonance frequencies. Vibration of exemplary membranes generates substantially periodic motion of resonators mechanically coupled to their inner surfaces. Useful membranes include thin membranes having a thickness selected from the range of 100 nanometers to 1000 nanometers. Membranes may comprise a wide range of materials including, but not limited to, polymer materials, dielectrics, semiconductors, metals, ceramics and composite materials of these. Membranes useful for some applications are not permeable with respect to gases and/or liquids and therefore, are capable of maintaining their inner surface at a relative low pressure (e.g. less than 10-100 Torr) while their receiving surface is in contact with a high pressure region, liquid phase or solution phase.

In one embodiment, the membrane comprises a piezoelectric material, including doped piezoelectric materials, and the means for vibrating the membrane is a driving circuit capable of making the piezoelectric material vibrate at selected frequencies. The driving circuit may be configured to provide an oscillating electric potential to the membrane so as to generate a surface acoustic wave on the inner surface of the membrane. Alternatively, the means for vibrating the membrane may comprise a mechanical actuator, such as a surface acoustic wave generator comprising transducers positioned on the perimeter of the pillar resonator array or an actuator capable of vibrating a mechanical frame supporting the membrane.

In one embodiment, the receiving surface of the membrane is functionalized or derivatized to provide high surface accommodation of molecules subject to detection and/or analysis. For example, the receiving surface may be coated with a thin layer of a material, such as gold, that increases the accommodation coefficient of the receiving surface with respect to a broad class of molecules. Alternatively, the receiving surface may be functionalized in a manner providing selective accommodation characteristics, such as providing a large accommodation for specific molecules and a low accommodation coefficient for other species. For example, biological molecules, such as proteins and/or oligonucleotides, may be bound to the receiving surface in a manner retaining their biological activities so as to provide a probe for identifying molecules that selectively interact with the surface bound biological molecules. In some applications of the present invention, functionalization or derivization of the membrane surface does not significantly disrupt or affect the mode structure and resonance frequencies of the resonators mechanically coupled to the inner surface of the membrane. Increasing accommodation of the receiving surface may also be accomplished in the present invention by holding the receiving surface at low temperatures.

Any detector capable of detecting changes in or measuring the spatial distribution of emission from the resonators is useable in present methods. Useful detectors include, but are not limited to, detectors having a detection surface positioned a selected distance from the inner surface of the membrane that are capable of determining the area of the detection surface that interacts with emission over a selected time interval, such as a time interval corresponding to one or more oscillation cycles of resonators in the system. Useful detectors for sensors of the present invention capable of measuring electric charge, include detectors capable of measuring the net intensity of emission from resonators in the system. Exemplary detectors for detecting emission from field emitting resonators include MCP analyzers, thin film displays and phosphorescent screens. Exemplary detectors for detecting emission from photoemissive resonators include, charge coupled devices, photodiode arrays, and photomultiplier tubes and arrays thereof.

In another aspect, a sensor of the present invention comprises an array of resonators that are mechanically and/or electrically biased such that they only generate emission upon the interaction of the molecule and the receiving surface of the detector. This configuration of the present invention is capable of operation in Off-On detection mode providing very good sensor—sensor response times. In one embodiment, the membrane is vibrated, thereby setting the resonators into substantially periodic motion characterized by selected mechanical modes and resonance frequencies. However, the electrical and/or mechanical biasing of individual resonators is such that they do not undergo emission in this unperturbed state. Furthermore, the biasing provided results in emission from at least one resonator in the array upon perturbation of the sensor system by interaction of a molecule or group of molecules and the receiving surface of the sensor. In one embodiment, resonators proximate to the region of the inner surface opposite contact points between the receiving surface and the molecule undergo emission upon contact between the receiving surface and the molecule. This biasing scheme provides an effective means of reading out a large number of resonators on a very short time scale. This aspect of the present invention provides detectors and sensors exhibiting good time resolution and very low noise levels which are ideally suited for using in a time-of-flight mass analyzer. It is important to note that in the ON/OFF detection mode, a molecule interacting with the receiving surface cause electrically and/or mechanically resonators near the impact site to emit electrons and/or electromagnetic radiation. Electrical bias values for the resonators are of the order of 100 mV to about 5 V, and for some applications of the order of 100 mV to about 500 V, depending on material and geometry used. Truly applied bias in some embodiments of this and other aspects of the present invention, however, is much larger so as to initiate emission.

In one embodiment, the resonators are electrically biased by application of a voltage to the membrane and/or providing a grid electrode held at a selected electric potential between the inner surface of the membrane and the detector. In addition, resonators of this aspect of the invention may be mechanically biased by proper selection of the physical dimensions, composition and physical properties of the resonators. Furthermore, resonators of this aspect of the invention may be biased by doping and/or metalization processing which affect their work function and/or by integration of single electron transistors to the resonators.

The sensors, detectors and analyzers of the present invention are broadly applicable to a variety of applications. Exemplary applications of the methods, devices and device components of the present invention include, environmental sensing, high-throughput screening, competitive binding assay methods, proteomics, mass spectrometry, quality control, sensing in microfluidic and nanofluidic applications such as lab on a chip sensors, and sequencing DNA and proteins.

In one embodiment, devices of the present invention provide detectors, mass analyzers and charge analyzers for mass spectrometry systems including, but not limited to, ion traps, time-of-flight mass spectrometers, tandem mass spectrometers, and quadrupole mass spectrometers. In one useful embodiment, a sensor of the present invention comprises a detector in a time-of-flight mass analyzer. In an embodiment of this aspect of the present invention, the detector/analyzer is provided at the end of a TOF flight tube and position to receive ions separated on the based of mass-to-charge ratio exiting the flight tube. Importantly, the analyzers of the present invention provide a means of independently measuring molecular mass and electric charge, in contrast to conventional mass spectrometry systems which typically only provide measurements of mass-to-charge ratio. The fast temporal resolution and large active areas of the present sensors and analyzers make them particularly well suited for mass spectrometry applications.

In another aspect, the sensors and analyzers of the present invention provide device components in liquid phase flow-through probe systems. For example, the high sensitivity and fast temporal response provided by the present sensors and analyzers make them ideally suited for probes in high throughput screening systems for identifying interactions involving biological molecules, such as protein—protein interactions, protein—oligonucleotide interactions, protein—therapeutic agent interactions and oligonucleotide—therapeutic agent interactions. The inverted membrane—resonator geometry of the present invention enables membranes to be easily functionalized or derivatized by incorporation of surface bound biomolecules, such as proteins and oligonucleotides. This enables sensors of the present invention to be used in competitive binding assay techniques. The inverted membrane—resonator geometry of the present invention also allows exposure of the receiving surface to solution phase conditions while maintain the resonators at a pressure low enough to achieve reproducible mode structure and selected resonance frequencies.

In another aspect, the present invention also includes sensors comprising a membrane having a single resonator mechanically coupled to the inner surface of the membrane.

In this embodiment, detection of or measurement of changes in the spatial distribution of emission from the single resonator mechanically coupled to the membrane provides a sensitive means of detecting molecules and measuring molecular mass with good resolution. In one embodiment, an array comprising a plurality of such single resonator sensors having a single resonator are provided to achieve larger net effective active areas.

Sensors and analyzers of the present invention are capable of detecting and/or analyzing a diverse range of molecules, including neutral molecules and molecules possessing electric charge, such as singly and multiply charged molecules. In contrast to conventional detectors such as MCP detectors, sensors and analyzers of some embodiments of the present invention exhibit a detection sensitivity that increases with molecular mass and, therefore, are useful for detecting an analyzing very large molecules, including, but not limited to biological molecules such as proteins, peptides, DNA molecules, RNA molecules, oligonucleotides, lipids, carbohydrates, polysaccharides, glycoproteins, and derivatives, analogs, variants and complexes these including labeled analogs of biomolecules. Sensors and analyzers of some embodiments have a very wide dynamic range in terms of the range of molecular masses that can be analyzed. Mass sensitivity provided by mass analyzers and sensors of some embodiments of the present invention is on the order of zeptograms, and in other embodiments on the order of 10ths of zeptograms. The charge sensitivity of sensors of the present invention is about $10^{-6}$ e/sqrt(Hz), where e is the electric charge. The response time of sensors of the present invention is 1/f as maximal value with f being the resonator frequency, f will be in the range of 1 MHz to 10 GHz. This results in response time as low as 0.1 nanoseconds.

In another aspect, the present invention provides a method of sensing one or more molecules comprising the steps of: (1) providing a sensor comprising a membrane, a plurality of electromechanical resonators and a detector, wherein the membrane has a receiving surface for receiving the molecule and an inner surface opposite to the receiving surface, wherein the resonators extend vertically along a plurality of different axes that intersect the inner surface of the membrane, the resonators comprising emissive elements that generate emission having a spatial distribution, the detector positioned to receive the emission from the resonators; (2) vibrating the membrane of the sensor, wherein vibration of the membrane causes each of the resonators to resonate; (3) contacting the receiving surface of the membrane with the molecule, thereby causing a change in the spatial distribution of the emission from the resonators; and (4) detecting the change in the spatial distribution of emission from the resonators, thereby sensing the molecule. Optionally, the method of this aspect of the present invention further comprises releasing said molecule from said receiving surface. Optionally, the method of this aspect of the present invention comprises a method of determining the mass of the molecule; wherein the method further comprises the step of measuring the change in the spatial distribution of emission from the resonators. Optionally, the method of this aspect of the present invention comprises a method of determining the electric charges of the molecules, wherein the method further comprises the step of measuring a change in intensity of emission from the resonators, thereby measuring the electric changes of the molecules.

BRIEF DESCRIPTION OF THE DRAWINGS

FIG. 2 provides an expanded view of a sensor of the present invention showing a single pillar resonator mechanically coupled to a region of the membrane.

FIGS. 3A, 3B and 3C provide schematic diagrams illustrating the function of mass sensors of an embodiment of the present invention. FIG. 3A shows a schematic of a pillar resonator emitting electrons and/or photons onto a photoluminescent screen or other equivalent detector prior to vibration of the membrane. FIG. 3B shows a schematic of the pillar resonator emitting electrons or photons upon vibration of the membrane illustrating how oscillation of the resonator results in a larger spot size on the detector. FIG. 3C shows a schematic of the pillar resonator emitting electrons or photons upon contact of a molecule undergoing detection and the receiving surface of the membrane. FIGS. 3D and 3E provide schematic diagrams illustrating operation of a sensor configuration incorporating a grid electrode and providing good temporal resolution.

FIG. 9 shows a schematic illustrating five mechanical modes determined for pillar resonators having a square cross sectional shape.

FIGS. 10A-10F provide modeling results corresponding to a pillar resonator having a square cross sectional profile.

FIGS. 11A-11F provide modeling results corresponding to a cylindrical pillar resonator having a circular cross sectional profile.

FIGS. 12A and 12B provides a bar graph showing calculated resonance frequencies: (a) and allowed x-direction amplitude (b) variations with the sidewall profile when the pillars are excited at their resonance frequencies. Sets 1-4 referenced on the Y axes of FIGS. 12A and 12B correspond to the pillar geometries of sets 1-4 set forth in Table 3.

FIGS. 18A-C shows the allowed amplitude and phase changes for frequency scans over pillar fundamental frequencies (see corresponding Tables 1-3 for conditions) determined in the modeling study.

FIGS. 19A, 19B and 19C provide schematic diagrams illustrating three detector configurations useful for mass analysis applications.

FIG. 25: Measured drain current $I_D$ VS. the source frequency f. The dependence of emission current, at room temperature, on applied ac and dc electric field. The resonance frequencies are 310 MHz and 372 MHz. (a) Emission current against applied ac power (from +14 to +18 dBm without a dc bias voltage). (b) Emission current against applied dc voltage (from $_i$300 mV to +300 mV), at a fixed ac drive frequency. Inset shows current-voltage characteristics of the nanopillar with on- and off-resonance frequencies (310 MHz, 372 MHz, and 400 MHz).

FIG. 26: (a) Fowler-Nordheim characteristics of the nanopillar at room temperature with on- and off-resonance frequencies and no RF applied. (b) Data fitting Fowler-Nordheim. Solid line is a fit from Eq. (1) (see text for details).

DETAILED DESCRIPTION OF THE INVENTION

Figure 1A:
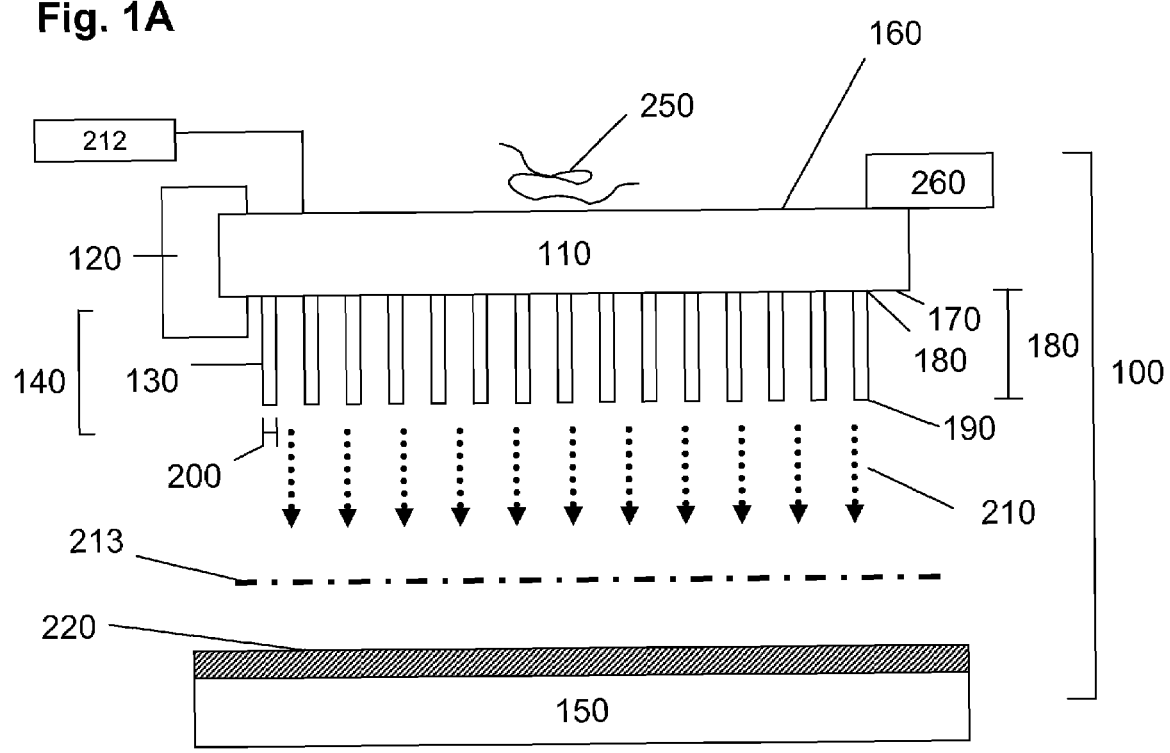
FIG. 1A provides a schematic diagram illustrating a side view of sensor of the present invention having a symmetrical array of pillar resonators having substantially the same physical dimensions.

Referring to the drawings, like numerals indicate like elements and the same number appearing in more than one drawing refers to the same element. In addition, hereinafter, the following definitions apply:

"Molecule" refers to a collection of chemically bound atoms with a characteristic composition. As used herein, a molecule refers to neutral molecules or electrically charged molecules (i.e., ions). Molecules may refer to singly charged molecules and multiply charged molecules. The term molecule includes biomolecules, which are molecules that are produced by an organism or are important to a living organism, including, but not limited to, proteins, peptides, lipids, DNA molecules, RNA molecules, oligonucleotides, carbohydrates, polysaccharides; glycoproteins, lipoproteins, sugars and derivatives, variants and complexes of these. The term molecule also includes candidate molecules, which comprise any molecule that it is useful, beneficial or desirable to probe its capability to interact with a molecule such as a target molecule. Candidate molecules include therapeutic candidate molecules which are molecules that may have some effect on a biological process or series of biological processes when administered. Therapeutic candidate molecules include, but are not limited to, drugs, pharmaceuticals, potential drug candidates and metabolites of drugs, biological therapeutics, potential biological therapeutic candidates and metabolites of biological therapeutics, organic, inorganic and/or hybrid organic-inorganic molecules that interact with one or more biomolecules, molecules that inhibit, decrease or increase the bioactivity of a biomolecule, inhibitors, ligands and derivatives, variants and complexes of these, including labeled analogs of these.

"Resonator" refers to an element or device component that undergoes oscillation, including substantially periodic oscillation. Resonators of the present invention may undergo vibrational motion, rotational motion (including free rotation), counter rotational motion, or any combination of these. Resonators useful in the present invention include, but are not limited to, pillar resonators, vibrational resonators, counter rotating and rotating resonators, torsional resonators and compound resonators.

"Resonance frequency" refers to the frequency at which a resonator resonates and includes fundamental (or natural) resonance frequency. Resonators of the present invention may be characterized by one or more frequency response curves (amplitude vs. frequency) which indicates a distribution of frequencies for a given mechanical mode of the resonator.

"Substantially periodic motion" and "substantially periodic oscillation" refers to motion in which the position(s) of the system or elements of the system are expressible in terms of periodic functions. Substantially periodic motion and substantially periodic oscillation is intended to include some deviation from purely periodic behavior, such as deviation from pure periodic behavior less than about 5%, and less than about 1% for some embodiments of the invention.

"Membrane" refers to a device component, such as a thin structural element. Membranes of the present invention are capable of mechanical vibration, including in some embodiments substantially periodic mechanical vibration. In one useful embodiment, a membrane is a structural element capable of establishing and maintaining acoustic waves, such as surface acoustic waves. Membranes of the present invention function to separate an environment having molecules to be sensed from a plurality of microelectromechanical resonators, nanoelectromechanical resonators mechanically and/or electrically coupled to the membrane. Membranes useful in the present invention may comprise a wide range of materials including semiconductors, dielectric materials, ceramics, polymeric materials, glasses and metals.

"The spatial distribution of emission from resonators" refers to the angular distribution of propagation or transmission axes of emission originating from one or more resonators. In the present invention spatial distribution of emission can be monitored and/or measured by any means known in the art. In one embodiment, for example, the spatial distribution of emission from one or more resonators is monitored and/or measured by measuring the area of a hypothetical plane positioned a selected distance from the inner surface of the membrane that interacts with emission during a selected time interval (commonly referred to as the spot size), for example a time interval corresponding to one or more complete oscillation cycles of one or more resonators.

In the following description, numerous specific details of the devices, device components and methods of the present invention are set forth in order to provide a thorough explanation of the precise nature of the invention. It will be apparent, however, to those of skill in the art that the invention can be practiced without these specific details.

This invention provides methods, devices and device components for detecting, sensing and analyzing molecules. The present invention provides detectors capable of providing measurements with good time resolution, and provides sensors capable of providing simultaneous high resolution measurements of molecular mass and electric charge.

In one embodiment, the detector/analyzer comprises a thin membrane with NEMS (nanoelectromechanical) or MEMS (microelectromechanical) pillar resonators distributed on its inner surface in an array fashion. The membrane is capable of being set into motion, such as periodic vibrational motion, by a means of vibrating the membrane. Vibration of the membrane in turn causes the resonators to resonate. Useful means of vibrating the membrane include a mechanical holder capable of vibrating the membrane that is coupled to the membrane itself or a substrate layer supporting the membrane. Alternatively, for membranes comprising piezoelectric or doped piezoelectric materials a means of vibrating the membrane comprises a piezoelectric driving circuit that causes a piezoelectric membrane to oscillate. In a useful embodiment, vibration of the membrane results in surface acoustic wave generation and propagation, for example on an inner surface of the membrane mechanically coupled to the NEMs and/or MEMs resonators.

Electrical and mechanical biasing provided to the pillars through the membrane is used to initiate emission from the pillars, such as field emission or photoemission. Electrons and/or photons are emitted with a spatial distribution that depends on the vibrational state of the pillars. The emitted electrons and/or photons are detected using an appropriate detector, such as fluorescent/phosphorescent film, photomultiplier tube, micro-channel plate, or other equivalent methods. The molecules to be detected come into contact with the membrane side opposite the pillars, referred herein as the receiving surface. In one embodiment, the mechanical mode of the pillars proximate to and/or nearest to the point of contact is altered and the spatial distribution of electron and/or photon emission is changed, providing detection. Several forms of realization are possible including different NEMS structures in semiconductor materials by combining these with electron and/or light emitting sources.

FIG. 1A provides a schematic diagram illustrating a side view of sensor of the present invention having a symmetrical array of pillar resonators with substantially the same physical dimensions. Sensor 100 comprises membrane 110, means 120 of vibrating the membrane 110, a plurality of pillar resonators 130 provided in an array 140, and detector 150. Membrane 110 has a receiving surface 160 for receiving or contacting a molecule to be detected or analyzed and an inner surface 170 positioned opposite the receiving surface 160. Receiving surface 160 may be coated with a material that enhances its accommodation probability with respect to molecules interacting with it or may be functionalized or derivatized to provide for selective accommodation characteristics. Optionally, receiving surface 160 is coupled to means of releasing molecules 260 which is capable of releasing molecules from receiving surface 160 after detection and/or analysis.

Pillar resonators 130 have vertical lengths 180 which extend from inner surface 170 along axes that intersect inner surface 170 and are mechanically coupled to inner surface 170. This geometry of the pillar resonators 130 and membrane 110 is an example of what is referred to herein as an inverted membrane-resonator geometry. Pillar resonators are also characterized by their cross sectional dimensions 200. In the embodiment illustrated in FIG. 1A, first ends 180 of pillar resonators 130 are in physical contact with inner surface 170 and second ends 190 of pillar resonators are positioned distal to inner surface 170.

Means 120 of vibrating the membrane 110 is electrically and/or mechanically coupled to membrane 110 in a manner such that it is capable of setting and maintaining membrane 110 into motion, such as substantially periodic vibrational motion. In one embodiment, means 120 of vibrating the membrane 110 is capable of generating a surface acoustic wave on inner surface 170 of membrane 110. Vibration of membrane 110 causes pillar resonators to resonate, preferably for some applications at selected resonance frequencies. The vertical lengths 180, composition, cross sectional dimensions 200 and physical properties (e.g. Young's modulus) of pillar resonators 130 determine their mechanical resonance frequencies and mechanical modes for a given vibrational frequency of membrane 110. In one embodiment, pillar resonators 130 vibrate laterally with respect to their vertical lengths upon vibration of membrane 110.

Pillar resonators 130 comprise emissive elements capable of generating emission (schematically represented by arrows 210), such as free electrons and/or photons. Emission is initiated by biasing the pillar resonator through the membrane 110, for example by integration of power supply 212 capable of holding membrane 110 at a selected electric potential. Optionally, electrical biasing of resonators 130 is provided by incorporation of grid electrode 213 positioned between inner surface 170 and detector 150 capable of establishing and maintaining a selected grid electrode voltage useful for biasing resonators of the array. In one embodiment, emission 210 is continuously generated from second ends 190 of pillar resonators 130 during detection and/or analysis. The spatial distribution of emission 210 over a given time interval depends strongly on the mechanical mode structure and frequency of oscillating pillar resonators 130. Detector 150 is provided in a position to receive and detect emission 210. In the embodiment shown in FIG. 1A, detector 150 comprises a detection surface 220 positioned a selected distance from inner surface 170 such that it receives emission 210 from pillar resonators 130. In this embodiment, detector 150 is capable of detecting changes in the area of detection surface 220 that interacts with emission 210 during a selected time interval.

Interaction between a molecule (schematically illustrated as 250) to be detected and/or sensed and receiving surface 160 results in a change, such as a decrease, in the resonance frequency of at least one pillar resonator 130 in array 140. In some embodiments, the resonance frequencies of one or more pillar resonators positioned proximate to points opposite the contact points receiving surface 160 that interact with molecule 250 are decreased by the interaction. The change in resonance frequencies of one or more one pillar resonator 130 in array 140 results in an overall change in the spatial distribution of emission 210. Detection of this change in spatial distribution provides detection of molecule 250 and measurement of the extent of change in spatial distribution, for example the percentage decrease in spatial distribution, provides a measurement of the molecular mass of molecule 250. After detection or sensing, molecule 250 is optionally released from receiving surface 250 by means of releasing the molecule 260.

Figure 1B:
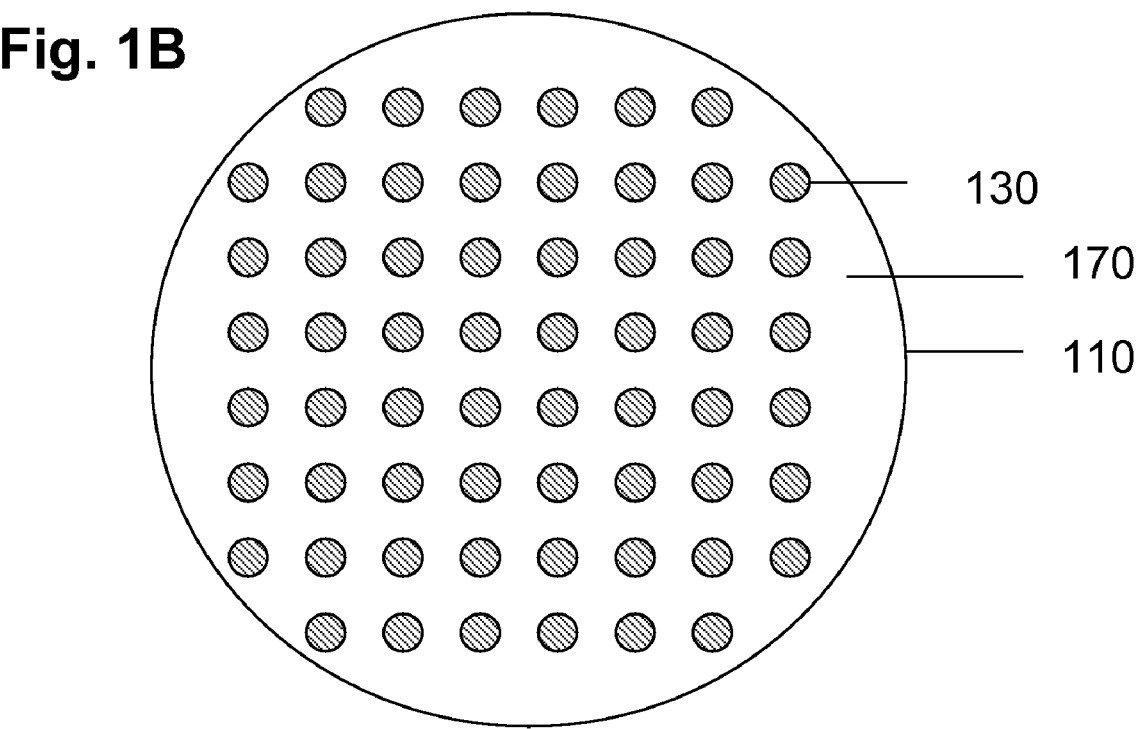
FIG. 1B shows a bottom view of a membrane and pillar resonator array wherein pillar resonators are distributed symmetrically on the inner surface of the membrane and wherein each pillar resonator is separated from adjacent pillar resonators by substantially the same distance (i.e within 10%).
Figure 1C:
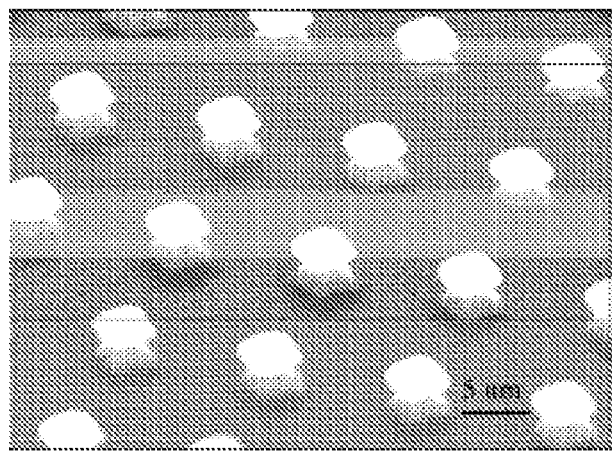
FIGS. 1C and 1D provides a scanning electron beam micrograph of a symmetrical pillar resonator array comprising pillar resonators separated from adjacent pillar resonators by the substantially the same distance.
Figure 1D:
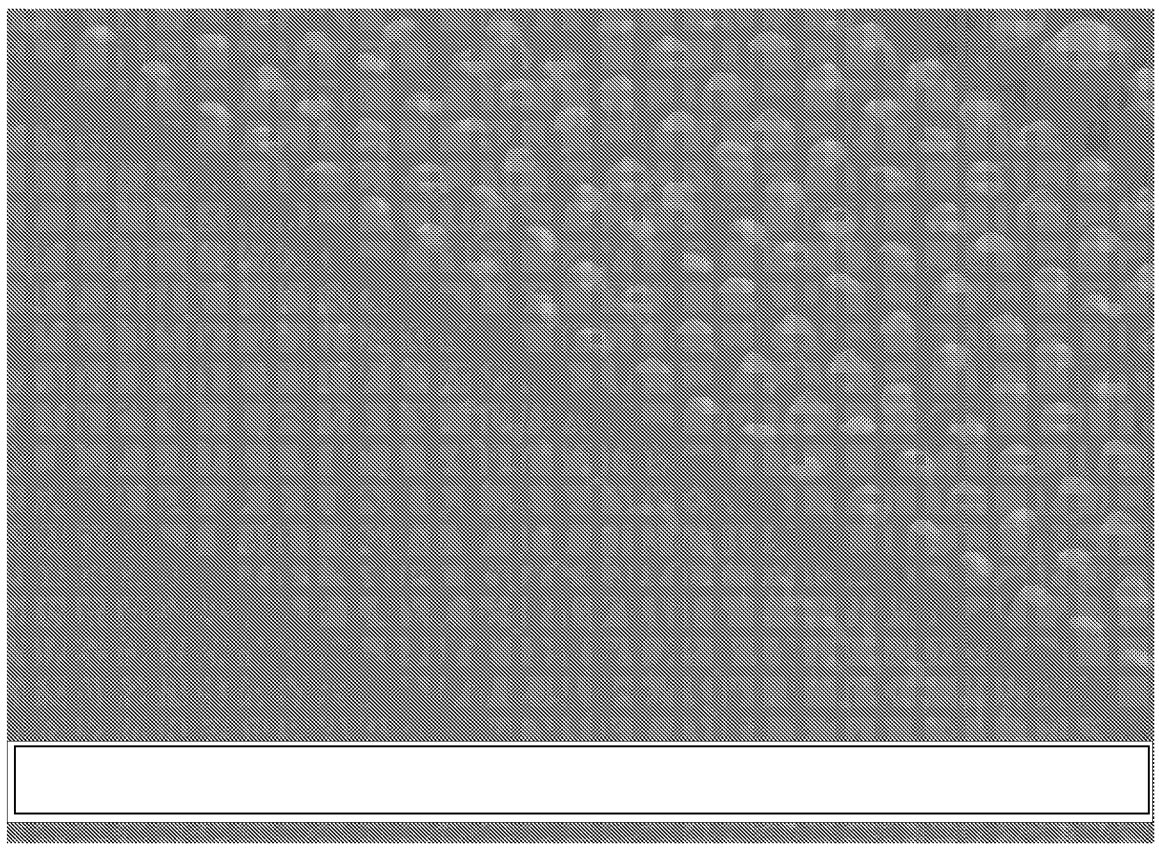

FIG. 1B shows a bottom view of a membrane and pillar resonator array wherein pillar resonators 130 are distributed symmetrically on the inner surface 170 of the membrane 110 and wherein each pillar resonator is separated from adjacent pillar resonators by substantially the same distance (e.g., within 10%). An advantage of this array configuration is that it provides detectors wherein the detection sensitivity and/or mass resolution does not depend at which point on the receiving surface of the membrane that a molecule under analysis/detection contacts. FIG. 1C provides a scanning electron micrograph of a symmetrical pillar resonator array comprising pillar resonators separated from adjacent pillar resonators by the substantially the same distance. The mechanical modes of the pillar resonators shown in FIG. 1C are on the order of about 100 MHz. FIG. 1D provides a scanning electron micrograph showing a plurality of symmetrical pillar resonator array each comprising pillar resonators of different physical dimensions.

Figure 1E:
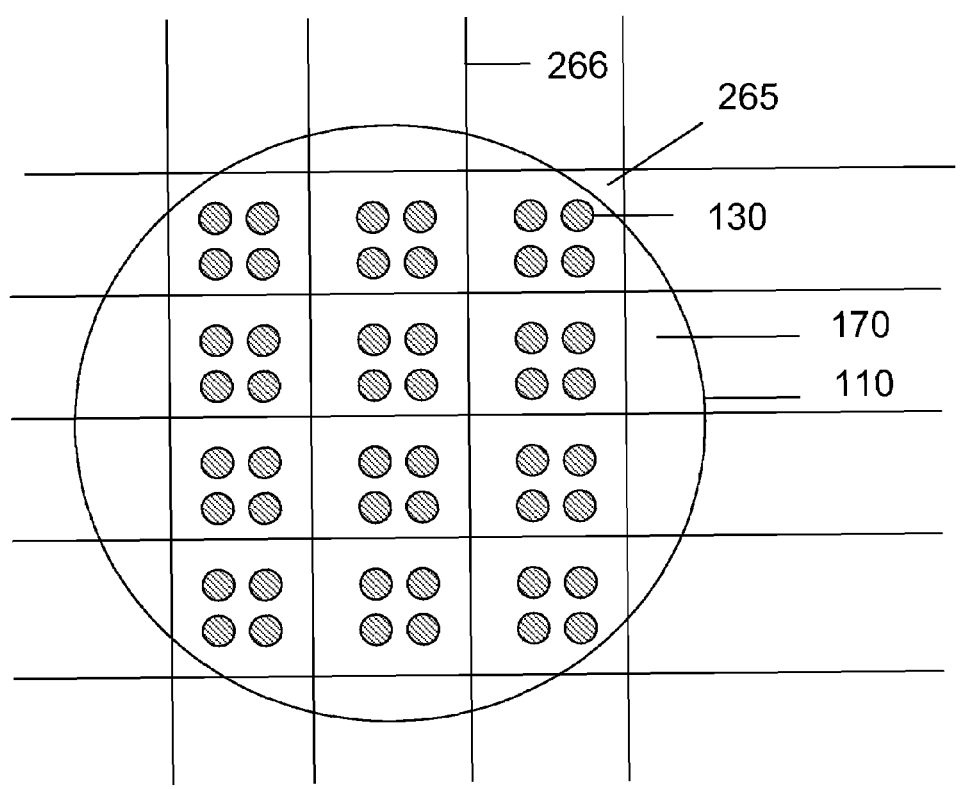
FIG. 1E provides a bottom view of a membrane and pillar resonator array having an alternative distribution wherein pillar resonators are distributed on the inner surface of the membrane 110 such that four pillar resonators are addressed to each grid element of a grid mapped onto the inner surface.

FIG. 1E provides a bottom view of a membrane and pillar resonator array having an alternative distribution wherein pillar resonators 130 are distributed on the inner surface 170 of the membrane 110 such that four pillar resonators are addressed to each grid element 265 of a grid 266 mapped onto the inner surface. In a useful embodiment of this aspect of the invention, each pillar resonator of the group of four address to a grid element have different physical dimensions and resonance frequencies such that they are responsive to molecules having different ranges of molecular mass. Therefore, this pillar configuration provides versatile detectors and analyzers responsive to molecules having a wide range of molecular masses.

FIG. 2 provides an expanded view of a sensor of the present invention showing a single pillar resonator mechanically coupled to a region of the membrane. The illustrated pillar resonator 300 comprises a semiconductor base 310 in contact with a field emission or photoemission tip 320. As shown in FIG. 2, semiconductor base 310 is in physical contact with inner surface 170 of membrane 110 and field emission or photoemission tip 320 is positioned distal to inner surface 170 of membrane 110. In this embodiment, membrane 110 comprises a doped piezoelectric material, semiconductor base has a graded (or doped) transition and field emission or photoemission tip has a geometry and level of doping adjusted for maximal emission. Pillar resonator 300 extends downwards toward the detector (see FIG. 1) and mass is loaded (i.e. molecules are received) to the receiving surface 160.

FIGS. 3A, 3B and 3C provide schematic diagrams illustrating the function of mass sensors of an embodiment of the present invention. FIG. 3A shows a schematic of a pillar resonator emitting electrons and/or photons onto a photoluminescent screen, MCP detector or other equivalent detector prior to vibration of the membrane. As illustrated in FIG. 3A the spatial distribution of emission detected by the detector is characterized by a relative small spot size. FIG. 3B shows a schematic of the pillar resonator emitting electrons or photons upon vibration of the membrane illustrating how oscillation of the resonator results in a larger spot size on the detector. In FIGS. 3B and 3C, surface acoustic waves generated by vibration of the membrane are represented by dotted lines and various positions of the oscillating pillar resonator are shown in dotted lines.

As illustrated in FIG. 3B, the spatial distribution of emission detected by the detector increases upon vibration of the membrane which in turn causes the resonators to resonate. This increase in spatial distribution is indicated by a significant increase in the spot size detected by the detector relative to the spot size shown in FIG. 3A. FIG. 3C shows a schematic of the pillar resonator emitting electrons or photons upon contact of a molecule undergoing detection and the receiving surface of the membrane. As shown by a comparison of FIGS. 3C and 3B, interaction between the molecule undergoing detection/analysis and the receiving surface attenuates the resonance amplitude of the pillar resonator, thereby decreasing the spatial distribution of emission detected by the detector. This decrease in spatial distribution is indicated by a decrease in the spot size detected by the detector relative to the spot size illustrated in FIG. 3B (i.e. the spot size prior to contact of the molecule and the receiving surface). Identification of this change in the spatial distribution of emission for the resonators provides a means of detecting the molecule and measurement of the extent of the decrease in spatial distribution provides a measurement of the mass of the molecule. The present invention also includes embodiments wherein pillar resonators are RTD integrated structures.

In a useful embodiment, a thin membrane is provided with a plurality of NEMS pillar resonators, wherein resonators are distributed on the membrane in an array fashion. The membrane material is set into motion by mechanical vibration generated by an actuator capable of vibrating the membrane or a holder element supporting the membrane. The present invention also includes use of a membrane comprising a piezoelectric material, and thus capable of generating surface acoustic waves upon application of an oscillating electric potential. The device allows operation at room temperature as it has been demonstrated for mechanical resonances alone and in combination with field emission. Lowering the temperature, however, reduces thermally induced vibrations, thus, enhancing the accuracy in mass detection.

In an embodiment, mechanical excitation of the resonators is provided by surface acoustic waves generated by transducers on the perimeter of the pillar resonator array. Use of the inverted membrane—resonator geometry illustrated in FIGS. 1, 2 and 3A-C allows for chemical or physical preparation of the membrane to enhance the adsorption and desorption processes of the molecules. Furthermore this enables the device to be used for molecule detection under low-pressure, for example for MALDI-TOF, or for liquid phase operation.

In one embodiment, biasing the pillar resonators through the membrane and/or via incorporation of a grid electrode initiates emission from the pillars. Electrons and/or photons are emitted with a spatial distribution depending strongly on the vibrational state of the pillar, as schematically illustrated in FIGS. 3A-3C. The emitted electrons and/or photons are detected using a fluorescent film, photomultiplier tubes, or other equivalent methods. Hence, it is preferential, but not required, that the membrane allows charge transport (the membrane can also contain a conducting layer). The detector membrane is then mounted in such a way that the pillars are not interacting directly with molecules contacting the membrane as shown in FIGS. 1, 2 and 3A-3C, hence the inversion of the pillars. However, contact between a molecule and the membrane results in a change in the mechanical mode and/or resonance frequency of the pillar and, thus change in the spatial distribution of electron and/or photon emission. On the detector side, the NEMS emitter array can be attached to a standard Multi Channel Plate (MCP) analyzer or a Thin Film Display (TFC) for direct visualization of the signal.

FIGS. 3D and 3E provide schematic diagrams illustrating operation of a sensor configuration incorporating a grid electrode and providing measurement with good temporal resolution. As shown in FIGS. 3D and 3E, a grid electrode 353 is provided between the inner surface of the membrane and the detector. The grid electrode is partially transmissive with respect to emission from the resonators, and comprises a plurality of transmissive regions 354 and nontransmissive regions 355. For the sake of clarity, FIGS. 3D and 3E provide an expanded view showing one transmissive region of the grid electrode 353. FIG. 3D shows the sensor operation when the resonators of the sensor are in an unperturbed state (i.e. prior to interaction between a molecule and the receiving surface) and FIG. 3E shows the sensor operation when the resonators of the sensor are in a perturbed state (i.e. upon interaction between a molecule and the receiving surface). As shown in FIG. 3D, a significant amount of the emission from the resonators in an unperturbed state is prevented from reaching the detector due to the presence of nontransmissive regions 355 of grid electrode 353. Detection of the emission transmitted by the grid electrode results in generation of a first signal ($I_{unperturbed}$). As shown in FIG. 3E, interaction of a molecule with the receiving surface changes the resonance frequency of the resonator in a manner resulting in a significant increase in the transmission of emission by grid electrode 353. Detection of the emission from resonators in a perturbed state that is transmitted by the grid electrode results in generation of a second signal ($I_{perturbed}$) that is measurably larger than the first signal ($I_{unperturbed}$). Detection of this increase in the signal generated by the detector provides a sensitive means of temporally resolving a contacting and/or binding event in real time.

Figure 4A:
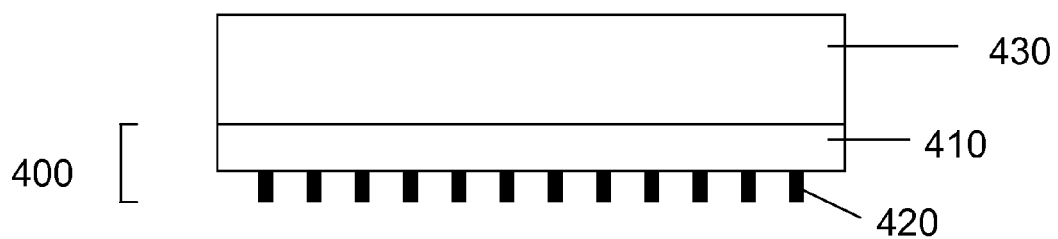
FIG. 4A provides a side view of a useful sensor design of the present invention wherein a processed substrate comprising an array of resonators coupled to a membrane is provided in contact with a supporting substrate to allow effective integration of the sensor into a selected device configuration for a given application.

FIG. 4A provides a side view of a useful sensor design of the present invention wherein a processed substrate comprising an array of resonators coupled to a membrane is provided in physical contact with a supporting substrate to allow effective integration of the sensor into a selected device configuration for a given application. As shown in FIG. 4A, processed substrate 400 comprising an array of resonators 420 coupled to a membrane 410. The processed substrate 400 is provided in physical contact with supporting substrate 430. In one embodiment, the single pillars are integrated into an array and the whole device clamped or wafer bonded onto a frame, which allows access of the molecules to be detected through the back side. Mechanical excitation is achieved by either directly using surface acoustic wave generators on the substrate with the pillars or by vibrating the mechanical frame of the supporting structure. It is important to note that the pillars can be electrically DC biased or operated in AC mode, which is preferential in combination with MCPs.

A benefit of the present sensor configuration is that it is capable of operation at very low detector dark current levels, thereby accessing high detection sensitivities and allowing for integration in a TOF mass analyzer. For example, by tuning the electric field the dark current can be as low as $10^{-14}$ A for an array comprising about $1 \times 10^{10}$ emitters. This corresponds to about 625 electrons emitted in about 10 milliseconds, which is sufficiently long enough for a TOF to scan the mass range. The detector dark current can be further reduced by using a turn-on characteristic which are very sharp. Another approach for minimizing detector dark current is to use resonant field emission through localized states or single electron turnstiles.

Figure 4B:
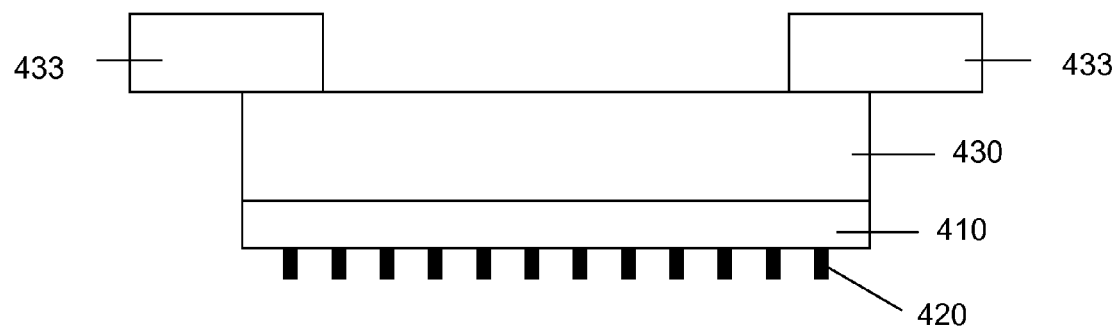
FIGS. 4B and 4C provide schematic drawings of a sensor of the present invention having a means of selectively adjusting the elasticity of the membrane.
Figure 4C:
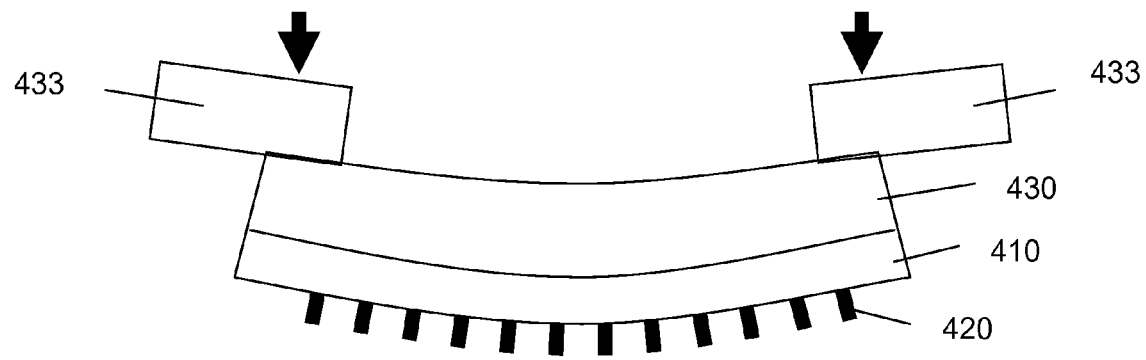

In another aspect, sensors of the present invention comprise a membrane having a selectively adjustable elasticity. Embodiments of this aspect of the present invention incorporate a means of selectively adjusting the elasticity of the membrane to tune the mechanical biasing of resonators mechanically coupled to the inner surface of the membrane. An advantage of this mechanical biasing scheme is that it is capable of continuous selective adjustment of the mechanical biasing of resonators. FIGS. 4B and 4C provide schematic drawings of a sensor of the present invention having a means of selectively adjusting the elasticity of the membrane. The sensor shown in FIG. 4B further comprises two anchoring elements 433, which are capable of holding the membrane 420 and supporting substrate 430 in a selected position providing a selected first membrane elasticity. The position and/or orientation of the anchoring elements 433 is selectively adjustable in this embodiment of the present invention to provide a means of selectively adjusting the elasticity of the membrane. Changing the position and/or orientation of the anchor points may be realized using an adjustable frame, a piezoelectric actuator or some other type of actuating system (schematically illustrated by the arrows in FIG. 4C). FIG. 4C shows a schematic diagram of the sensor wherein the position and orientation of the anchoring elements 433 has been changed in a manner giving rise to a bend in the membrane, thereby provide a second membrane elasticity that is different from the first membrane elasticity. The arrows in FIG. 4C schematically show an actuator capable of providing the change in position and orientation of the anchor elements. Adjustable elasticity of sensors of the present invention is also useful for overcoming material strain related problems in sensor membranes.

In one embodiment, mass selectivity is achieved by calibrating the degree of attenuation of the mechanical motion resulting from interaction of a molecule and the membrane. Under some experimental conditions, the change in the spatial distribution of emission is directly proportional to the molecular mass. For attaining a larger band-width, pillars with different lengths can be addressed on the same grid element of the inner surface of the membrane. For example, employing a grid area of 5×5 microns$^2$ and pillar resonator diameter of around 100-250 nm, addressing of four pillars per grid element is achievable. Optimally, the resulting spot sizes match the detector resolution. In one embodiment, the electron emission intensity is tuned with respect to the lengths of the pillars by grading (doping) the starting material. For some sensor designs, the taller and narrower the pillar resonator, the better in terms of field emission and spot size, but the lower the resonance frequency.

Mass resolution of the present NEMS detectors and analyzers is determined, in part, by the mechanical system of pillar and membrane. Further enhancement of mass resolution is achieved by shrinking the cross sectional dimensions of the pillars and enhancing field emission. In one embodiment, this is achieved either using carbon nanotubes (CNTs), metal nanotubes, and semiconductor nanotubes. The attainable pillar diameters using these materials are of the order of 1-10 nm. Field emission or photoemission is also enhanced by adjusting the pillar tip's geometry and by modifying the pillar's and pillar tip's doping (different grading in the pillar).

Typical frequencies of the lowest mechanical mode are on the order of 0.5-1.5 GHz. This underlines the speed of operation of such an integrated NEMS for mass sensing.

In one embodiment, the final step of mass detection is to release the molecules in case of strong adhesion to the membrane after detection. This is performed by either heat pulses generated by electrical current pulses or optical pulses (similar to MALDI) which supply the energy necessary for detaching the molecules. Finally, packaging of the NEMS field emitter array can be combined with the detector stage, thus avoiding the formation of water layers caused by ambient humidity.

Figure 5:
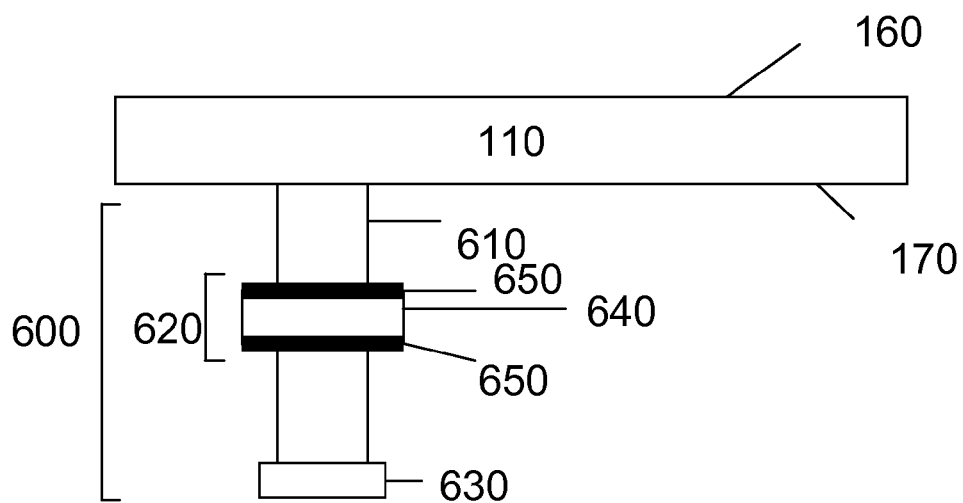
FIG. 5 provides an expanded side view of a pillar resonator having an integrated single electron transistor.

In order to achieve multifunctional sensors capable of providing simultaneous measurements of a mass and charge sensitivity the pillar resonators are equipped with an integrated charge island, also referred to as a single electron tunneling transistor or quantum dot. FIG. 5 provides an expanded side view of a pillar resonator having an integrated single electron tunneling transistor. As shown in FIG. 5, pillar resonator 600 comprises semiconductor base 610, integrated single electron transistor 620 and field emission or photoemission tip 630. Integrated single electron transistor comprises a Coulomb island 640 positioned between two tunneling barriers 650. The single electron transistor is located in the pillar and functions as a valve for the electrons on their way to the tip of the pillar where field emission occurs. The advantage of this sensor design is that the localized charge in the transistor is sensitive to any charge variation ($\delta Q$) in its environment. Therefore, an impinging molecule with mass m alters the mechanical motion of the pillar-membrane system, while the charge of the molecule $z=\delta Q$ will interact capacitively with the transistor, thus modulating the field emission intensity.

Figure 6:
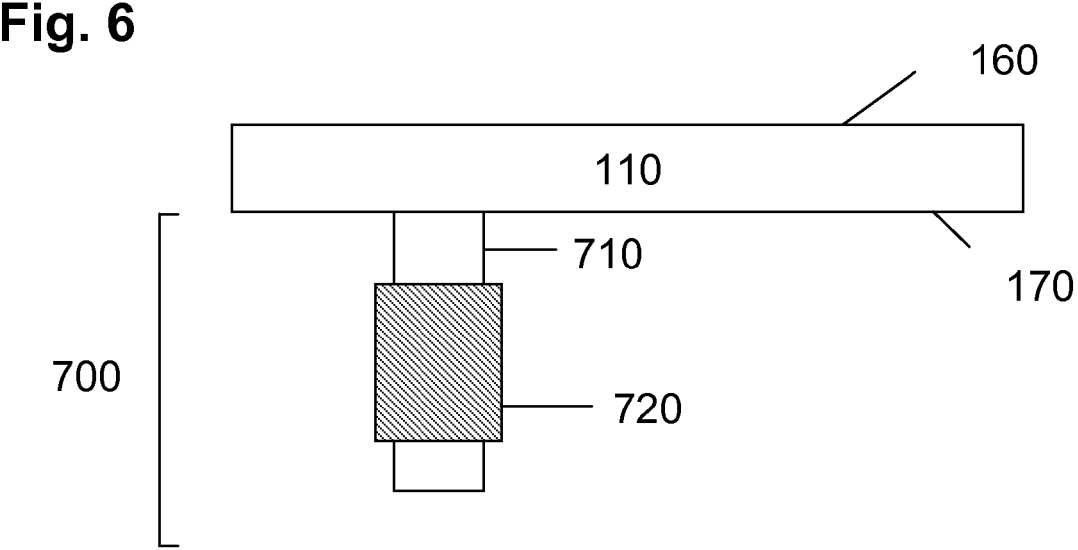
FIG. 6 shows an expanded side view of a pillar resonator having an integrated light emitting device of any kind.

In another embodiment, light emitting devices are integrated into the nano-pillar resonator to provide photoemission. FIG. 6 shows an expanded side view of a pillar resonator having an integrated light emitting device. As shown in FIG. 6, pillar resonator 700 comprises a nanowire or microwire 710 which is derived from a substrate containing a semiconductor heterostructure 720 which is optically active. Exemplary materials for optically active semiconductor heterostructures 720 useful in the present devices include, but are not limited to, Ga, As, and Al. This approach enables the fabrication of an array of optically emissive semiconductor pillar resonators. Preferentially for some applications, layer sequences comprising vertical cavity surface emitting lasers (VCSELs) or surface emitting LEDs are used for heterostructures 720. Laser structures have the advantage of offering a well defined frequency spectrum which can be exploited for enhancing the information density, i.e., for more accurate mass sensing. It is important to note that the membrane employed in these sensor designs does not necessarily have to be made of piezoelectric materials, since the mechanical frame of the membrane is also usable to provide mechanical vibration. In some embodiments, however, a piezoelectric membrane offers better resolution and stronger mechanical agitation. Furthermore, the required base contact for the light emitting structure of the pillar resonators can be integrated by overgrowth or evaporation of a thin optically transparent metal layer over the readily processed pillars on wafer scale.

In another embodiment, the design elements illustrated in FIGS. 5 and 6 are integrated in one pillar design thereby fabricating pillar resonators comprising quantum dot lasers. In a useful embodiment, this design is achieved by reducing the pillar diameter to below 100 nm, which creates a sufficient confinement potential for the electrons to form the required zero-dimensional states. This brings together the unprecedented charge sensitivity of quantum dots with the high degree of tunability of lasing devices and the mass sensitivity of the NEMS structure. Again, it is important to note that the inverted membrane-pillar geometry of the present invention allows for chemical preparation of the receiving surface, whereas on the pillar resonators are placed on the inner surface of the membrane where they are completely shielded from physical contact with the molecules undergoing detection and analysis.

Figure 7:
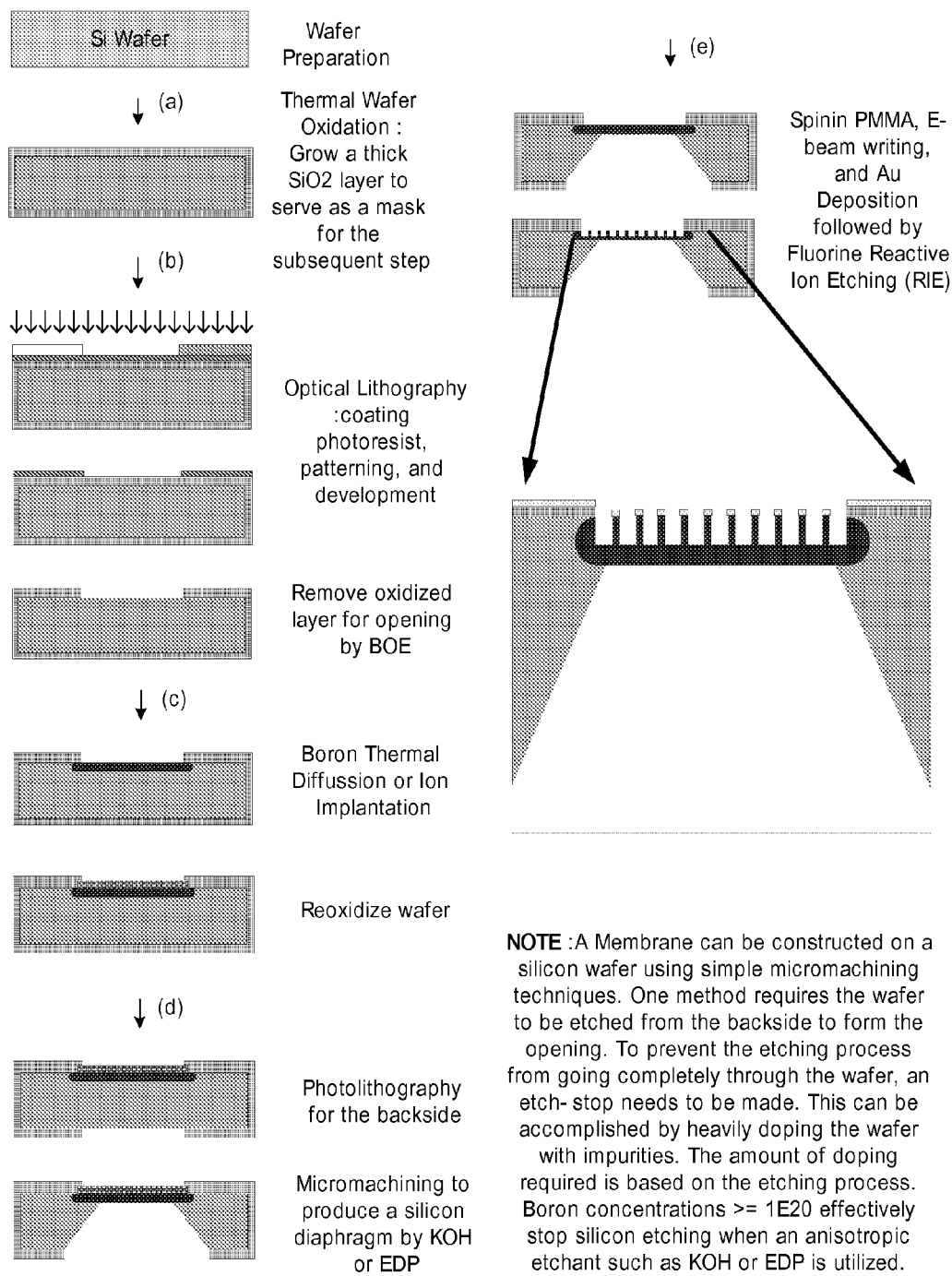
FIG. 7 provides a schematic diagram showing processing steps in an exemplary method of preparing a membrane and a pillar resonator array useful in the present methods and devices.

FIG. 7 provides a schematic diagram showing processing steps in an exemplary method of preparing a membrane and a pillar resonator array useful in the present methods and devices. As shown in panel (a) of FIG. 7, a silicon wafer is provided and thermally oxidized to grow a $SiO_2$ outer layer to provide mask elements in subsequent processing steps. As shown in panel (b) of FIG. 7, the Si wafer having a $SiO_2$ outer layer is subsequently coated with photoresist, patterned and developed using conventional optical photolithography techniques. Next, the region of the oxidized layer that are not masked with photoresist are removed, for example via etching techniques. As shown in panel (c) of FIG. 7, the exposed region (unmasked) of the silicon wafer is doped, for example with boron, using thermal diffusion and/or ion implantation methods, and the wafer is reoxidized. As shown in panel (d) of FIG. 7, optical photolithography is used to pattern the backside of the Si wafer and the patterned surface on the backside is micromachined to produce a silicon membrane by wet and/or dry etching methods. As shown in panel (e) of FIG. 7, a PMMA layer is spin coated on the exposed upper surface of the processed Si wafer. Pillar definition and fabrication is subsequently achieved by electron beam writing lithography and gold deposition, followed by fluorine reactive ion etching. As illustrated in the sequence of processing steps shown in FIG. 7, membrane and pillar resonator arrays may be constructed using conventional wafer materials and micromachining techniques. In the method illustrated in FIG. 7, the wafer is partially, but not completely, etched from the backside to form the opening, therefore, an etchstop may be required. One means of accomplishing this is by heavily doping the wafer with impurities. The amount of doping required will depend on the etching process employed to form the opening. For example, boron concentrations greater than or equal to $1\times10^{20}$ (number B atoms per $cm^3$) effectively stops silicon etching when an anisotropic etchant such as KOH and EDP is used.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. Methods and devices useful for the present methods can include a large number of optional device elements and components including, ion optics such as ions lens, optics for manipulating electromagnetic radiation such as lens, reflectors and windows, microfluidic and nanofluidic elements such as channels and chambers, flow through reactors, vacuum chambers, temperature sensors and controllers, valves, pumps, ion sources including MALDI and ESI ion sources, charge reduction elements, separation systems including chromatographic systems (i.e gas phase and liquid phase chromatography systems) and capillary electrophoresis systems, mass analyzers, and mobility analyzers.

STATEMENTS REGARDING INCORPORATION BY REFERENCE AND VARIATIONS

The follow in references relate generally to mass spectrometry, nanoelectromechanical devices or optically active materials which and are incorporated by reference in their entireties herein: (1) R. Aebersold and M. Mann, (2003) Nature 422:198; (2) F. W. Beil, A Wixforth, R. H. Blick. (2002) Proceedings of IEEE Sensors1:1285 (3) A. Buldum and J. P. Lu, (2003) Physical Review Letters 91:236801; (4) K. L. Ekinci, X. M. H. Huang, and M. L. Roukes, (2004) Applied Physics Letters 84:4469; (5) H. S. Kim, R. H. Blick, D. M. Kim, C. B. Eom, (2004) Applied Physics Letters 85:2370; (6) J. Kirschbaum. E. M. Hohberger, and R. H. Blick, W. Wegscheider, M. Bichler, (2002) Applied Physics Letters 81:280; (7) A. Kraus, A. Erbe, and R. H. Blick, (2000) Nanotechnology 11(3); (8) L. Pescini, A. Tilke, R. H. Blick, H. Lorenz, J. P. Kotthaus, W. Eberhardt, D. Kern, (2001) Advanced Materials 13:1780; (9) E. M. E. Toimil Molares, E. M. Hohberger, R. H. Blick, R. Neumann, Ch. Trautmann, (2003) Applied Physics Letters 82:2139; (10) D. V. Scheible, A. Erbe, and R. H. Blick, (2002) New journal of Physics 4:86; (11) D. V. Scheible and R. H. Blick (2004) Applied Physics Letters 84:4632; (12) X. Zheng et al. (2004) Physical Review Letters 92:106803L; and (13) D. V. Scheible, Ch. Weiss, J. P. Kotthaus, and R. H. Blick, Physical Review Letters 93, 186801 (2004); (14) "Dyanmic control and modal analysis of coupled nano-mechanical resonators," D. V. Scheible, A. Erbe and R. H. Blick, Applied Physics Letters, Vol. 82, No.19, pgs 3333-3335 (2003); (15) "Mechanical gating of coupled nanoelectromechanical resonators operating at radio frequency", L. Pescini, H. Lorenz and R. H. Blick, Applied Physics Letters, Vol. 82, No. 3, pgs 352-3354 (2003) and (16) "Mechanical mixing in nonlinear nanomechanical resonators", Applied Physics Letters, Vol. 77, No. 19, pgs 3102-3104 (2000).

All references throughout this application, for example patent documents including issued or granted patents or equivalents; patent application publications; unpublished patent applications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Any appendix or appendices hereto are incorporated by reference as part of the specification and/or drawings.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. Separate embodiments of the invention are also intended to be encompassed wherein the terms "comprising" or "comprise(s)" or "comprised" are optionally replaced with the terms, analogous in grammar, e.g.; "consisting/consist(s)" or "consisting essentially of/consist(s) essentially of" to thereby describe further embodiments that are not necessarily coextensive.

The invention has been described with reference to various specific and preferred embodiments and techniques. However, it should be understood that many variations and modifications may be made while remaining within the spirit and scope of the invention. It will be apparent to one of ordinary skill in the art that compositions, methods, devices, device elements, materials, procedures and techniques other than those specifically described herein can be applied to the practice of the invention as broadly disclosed herein without resort to undue experimentation. All art-known functional equivalents of compositions, methods, devices, device elements, materials, procedures and techniques described herein are intended to be encompassed by this invention. Whenever a range is disclosed, all subranges and individual values are intended to be encompassed as if separately set forth. This invention is not to be limited by the embodiments disclosed, including any shown in the drawings or exemplified in the specification, which are given by way of example or illustration and not of limitation. The scope of the invention shall be limited only by the claims.

EXAMPLE 1

Computational Study of Membrane and Pillar Resonator Mechanical Mode Structure, Resonance Frequency and Response to Mass Loading The ability of sensors of the present invention to provide sensitive detection and mass analysis of molecules having large molecular masses was verified by computational studies. Specifically, the mechanical modes and resonance frequencies of exemplary pillar resonators and membranes were calculated and evaluated with respect to the utility of different sensor geometries and physical dimensions for sensing and detection applications. Predicted changes in resonance frequency caused by interaction between analytes in the receiving surface for exemplary membrane-pillar resonator configurations were calculated and membrane vibrational frequencies necessary to drive selected pillar resonator mechanical modes at selected resonance frequencies were determined. Furthermore, pillar resonator and membrane dimensions and shapes providing sensors exhibiting enhanced detection sensitivity and mass resolution were identified.

Resonators of the present invention may be characterized by frequency response curves for selected mechanical modes. Resonators characterized by spectrally pure frequency response curves are particularly useful in sensors of the present invention. Spectrally pure frequency response curves for a given mechanical mode are typically characterized by a single maximum and a relatively narrow distribution of frequencies. Such narrow frequency distributions allow for even slight changes in the resonance frequencies of resonators caused by interaction of a molecule with a receiving surface to be readily detected and quantitatively characterized. In the computational study, frequency response curves were calculated for a variety of pillar resonators in order to identify which geometries and physical dimensions provide optimal components in sensors of the present invention.

Numerical modeling of membranes and pillar resonators was accomplished using Solid Works/Cosmos Works and Femlab software packages. Table 1 provides geometries and physical dimensions of the pillar resonators evaluated. Table 2 provides the material properties used in the simulations and Table 3 provides cross sectional physical dimension parameters used in the frequency response analyses.

TABLE 1

Geometries and Dimensions of Pillar Resonators Evaluated

| Geometric Models | Top-part diameter or sidelength (nm) | Top-part height (nm) | Bottom-part diameter or sidelength (nm) | Bottom-part height (nm) |
|---|---|---|---|---|
| Dimension range | 50-100 | 20-60 | 50-100 | 100-300 |

TABLE 2

Material Properties Used in Computational Studies

| Material | Density $\rho$ (kg/m$^3$) | Young modulus E (GPa) | Poisson's ratio $\nu$ |
|---|---|---|---|
| Gold (Au) | 19320 | 78 | 0.35 |
| Silicon (Si) | 2330 | 150 | 0.20 |

TABLE 3

Parameters used in the frequency response analyses on circular cross-section pillars.

| Set | 1 | 2 | 3 | 4 | 5 |
|---|---|---|---|---|---|
| Geometry | Straight sidewall circular cylinder | Curved sidewall circular cylinder | Curved sidewall circular cylinder | Curved sidewall circular cylinder | Curved sidewall circular cylinder |
| Dimensions | Au: 50 nm tall, 50 nm dia Si: 200 nm tall, 50 nm dia | Au: 50 nm tall, 50 nm dia Si: 200 nm tall, 50 nm dia with 1/3 reduction halfway | Au: 50 nm tall, 50 nm dia Si: 200 nm tall, dia. reduced from top 50 nm to bottom 40 nm | Au: 50 nm tall, 50 nm dia Si: 200 nm tall, dia. increased from top 50 nm to bottom 60 nm (reduction in the middle) | Au: 50 nm tall, 50 nm dia Si: 200 nm tall, dia. linearly increased from top 50 nm to bottom 60 nm |
| Fundamental natural frequency (MHz) | 380 | 301 | 135 | 349 | 564 |
| Frequency sweep range (MHz) | 365-395 | 280-310 | 120-150 | 330-360 | 545-575 |
| Damping ratio $\xi$ | $10^{-3}$ | $10^{-3}$ | $10^{-3}$ | $10^{-3}$ | $10^{-3}$ |
| Mass damping parameter $\alpha$ | 2.352e6 | 1.849e6 | 8.378e6 | 2.163e6 | 4.145e6 |
| Stiffness damping parameter $\beta$ | 4.233e-13 | 5.395e-13 | 1.179e-12 | 4.613e-13 | 2.411e-13 |
| Force (N/m$^3$) | 4.63e12 | 7.73e12 | 4.20e12 | 2.00e13 | 2.05e13 |

Figure 8:
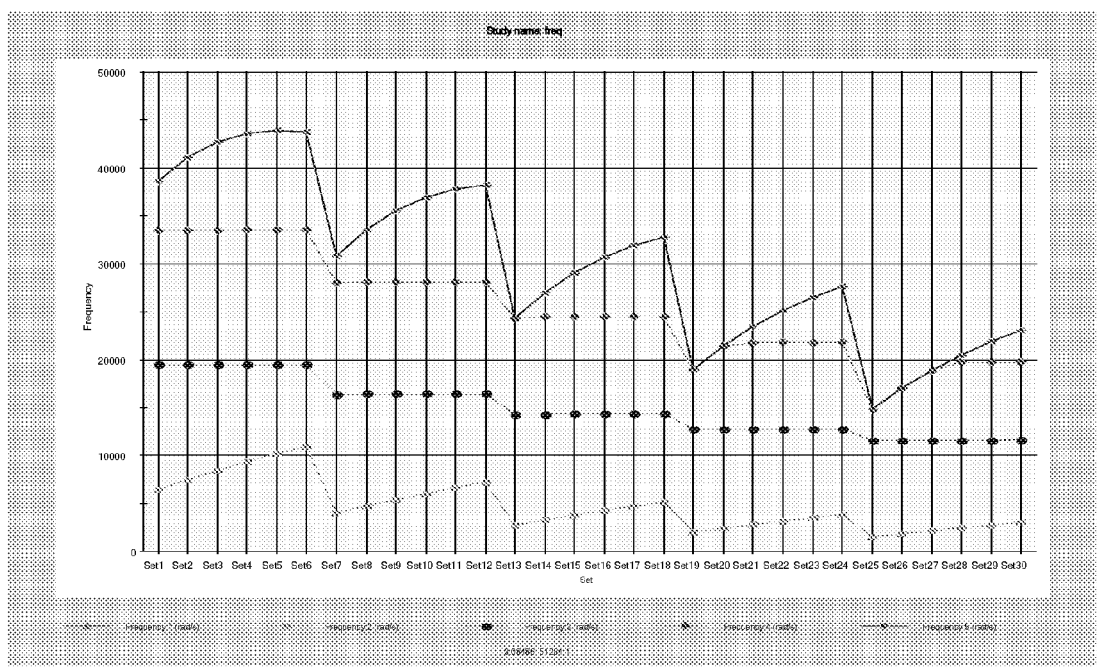
FIG. 8 provides an example of calculated fundamental resonance frequencies of $1^{st}$ to $5^{th}$ orders, corresponding to a pillar having a square cross sectional profile.

FIG. 8 provides an example of calculated fundamental resonance frequencies of $1^{st}$ to $5^{th}$ orders, corresponding to a pillar having a square cross sectional profile. The modeled square pillar resonator comprises a silicon base and a gold field emitting tip. In the simulations the gold field emitting tip has a fixed length equal to 50 nm, the length of the silicon base varies from 100-300 nm and the pillar cross-sectional side length varies from 50×50 nm-100×100 nm. Three hundred sets of square and circular cross-section with vertical sidewalls were analyzed.

FIG. 9 shows a schematic illustrating five mechanical modes determined for pillar resonators having a square cross sectional shape. The mode shapes of fundamental (or natural) resonance modes shown in FIG. 9 correspond to a silicon pillar having a length equal to 200 nm, cross sectional dimensions of 50 nm×50 nm-cross section and connected to a gold field emitting tip having a length of 50 nm.

FIGS. 10A-10F provide modeling results corresponding to a pillar resonator having a square cross sectional profile. FIG. 10A shows a schematic diagram of the pillar geometry used in the calculation showing a silicon base connected to a gold field emitting tip, both having a square cross sectional profile. FIG. 10B shows fundamental resonance frequencies corresponding to $1^{st}$ to $5^{th}$ mechanical modes for a silicon pillar having a length equal to 200 nm, connected to a gold field emitting tip having a length of 50 nm and having a varying cross sectional dimension. Fundamental resonance frequencies calculated for side lengths ranging from 50 nanometers to 100 nanometers are provided in FIG. 10B. FIG. 10C shows fundamental resonance frequencies calculated for pillar resonators having a silicon base having a length varying from 100 nanometers to 300 nanometers and side lengths varying from 50 nanometers to 100 nanometers. FIG. 10D shows fundamental resonance frequencies calculated for pillar resonators having a silicon base with a length varying from 100 nanometers to 300 nanometers and side lengths varying from 50 nanometers to 100 nanometers. FIG. 10E shows fundamental resonance frequencies calculated for pillar resonators having a silicon base having a length equal to 200 nanometers and side lengths varying from 50 nanometers to 100 nanometers, and having a gold tip with a thickness varying from 20 nanometers to 60 nanometers. FIG. 10F shows fundamental resonance frequencies calculated for pillar resonators having a silicon base having a length equal to 200 nanometers and side lengths varying from 50 nanometers to 100 nanometers, and having a gold tip with a thickness varying from 20 nanometers to 60 nanometers.

FIGS. 11A-11F provide modeling results corresponding to a cylindrical pillar resonator having a circular cross sectional profile. FIG. 11A shows a schematic diagram of the pillar geometer used in the calculation showing a cylindrical silicon base connected to a cylindrical gold field emitting tip, both having a circular cross sectional profile. FIG. 1AB shows fundamental resonance frequencies corresponding to $1^{st}$ to $5^{th}$ mechanical modes for to a silicon pillar having a length equal to 200 nm, connected to a gold field emitting tip having a length of 50 nm and having a varying cross sectional dimensions. Fundamental resonance frequencies calculated for diameters ranging from 50 nanometers to 100 nanometers are provided in FIG. 11B. FIG. 11C shows fundamental resonance frequencies calculated for pillar resonators having a silicon base having a length varying from 100 nanometers to 300 nanometers and a diameter varying from 50 nanometers to 100 nanometers. FIG. 11D shows fundamental resonance frequencies calculated for pillar resonators having a silicon base having a length varying from 100 nanometers to 300 nanometers and a diameter varying from 50 nanometers to 100 nanometers. FIG. 11E shows fundamental resonance frequencies calculated for pillar resonators having a silicon base having a length equal to 200 nanometers and diameter varying from 50 nanometers to 100 nanometers, and having a gold tip with a thickness varying from 20 nanometers to 60 nanometers. FIG. 11F shows fundamental resonance frequencies calculated for pillar resonators having a silicon base having a length equal to 200 nanometers and a diameter varying from 50 nanometers to 100 nanometers, and having a gold tip with a thickness varying from 20 nanometers to 60 nanometers.

FIGS. 12A and 12B provides a bar graph showing calculated resonance frequencies: (a) and allowed x-direction amplitude (b) variations with the sidewall profile when the pillars are excited at their resonance frequencies. Sets 1-4 referenced on the Y axes of FIGS. 12A and 12B correspond to the pillar geometries of sets 1-4 set forth in Table 3.

Figure 13:
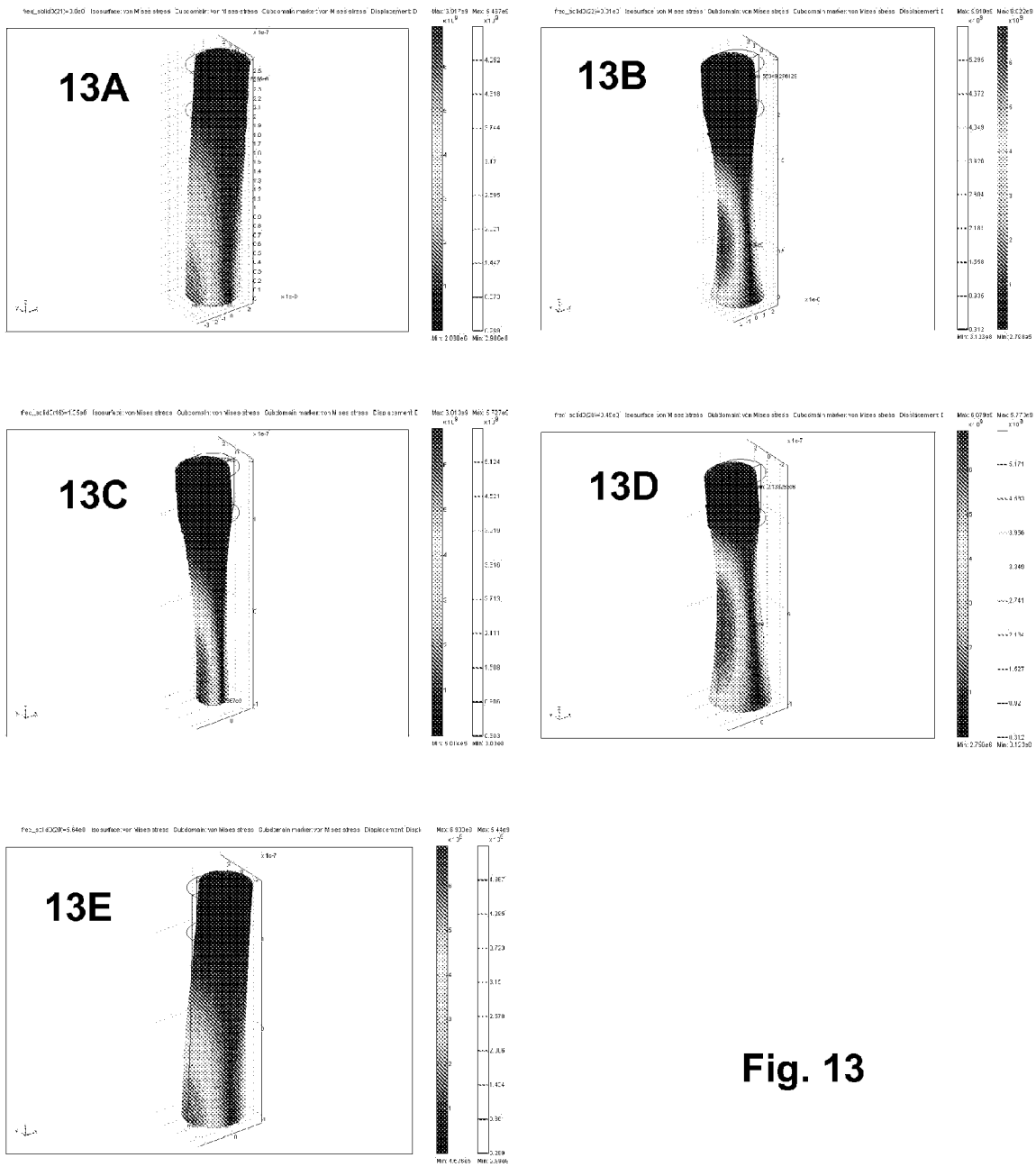
FIG. 13 provides calculated stress profiles at resonance frequencies in each set: Set 1 (*a*), Set 2 (*b*), set 3 (*c*), Set 4 (*d*) and Set 4 (*e*). The maximum von Miese stress locations are also labeled.

FIG. 13 provides calculated stress profiles at resonance frequencies in the pillar geometries set forth in sets 1-5 of table 3: Set 1 (a), Set 2 (b), set 3 (c), Set 4 (d) and Set 4 (e). The maximum von Miese stress locations are also labeled.

Figure 18A:
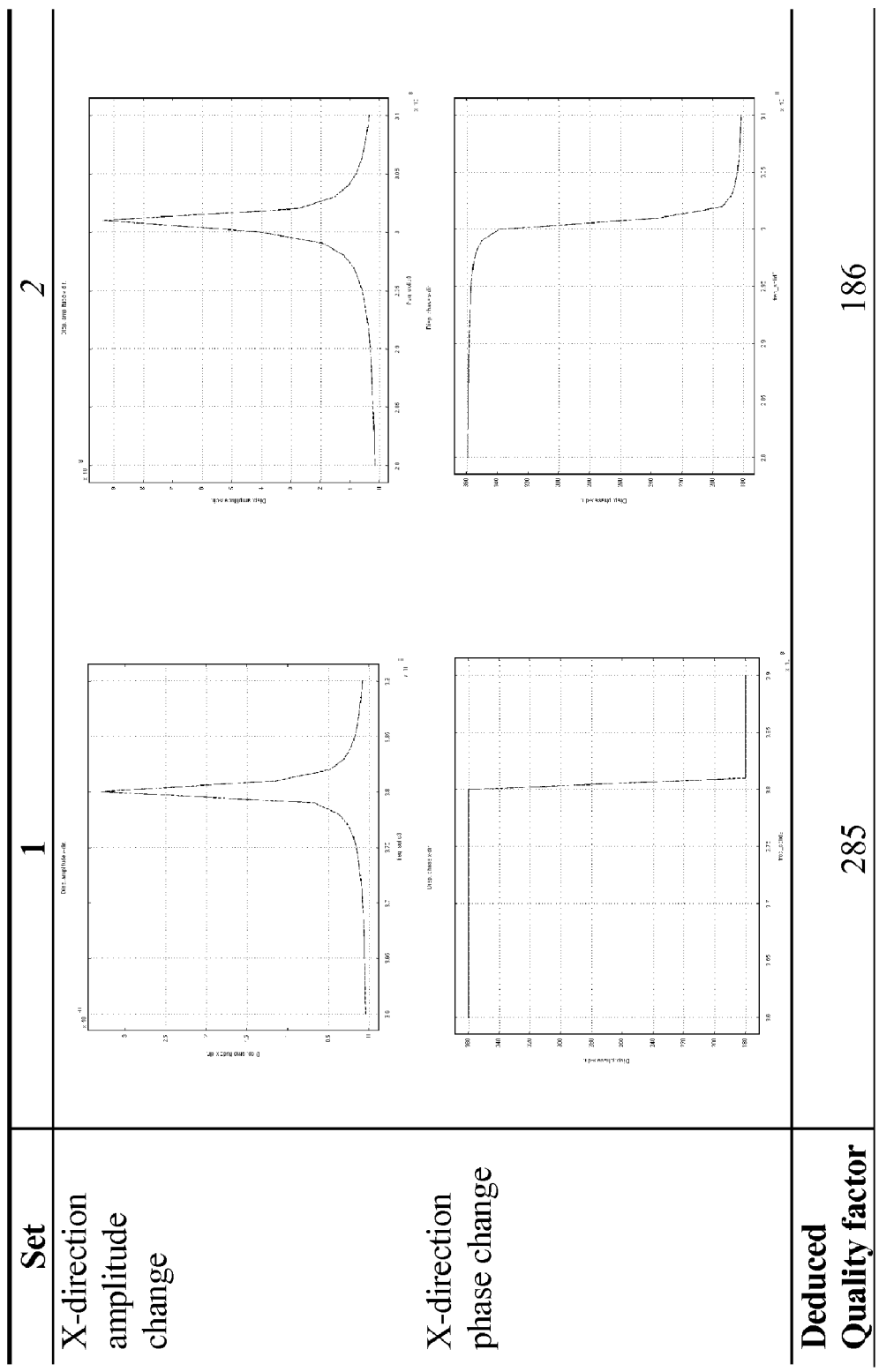
Figure 18B:
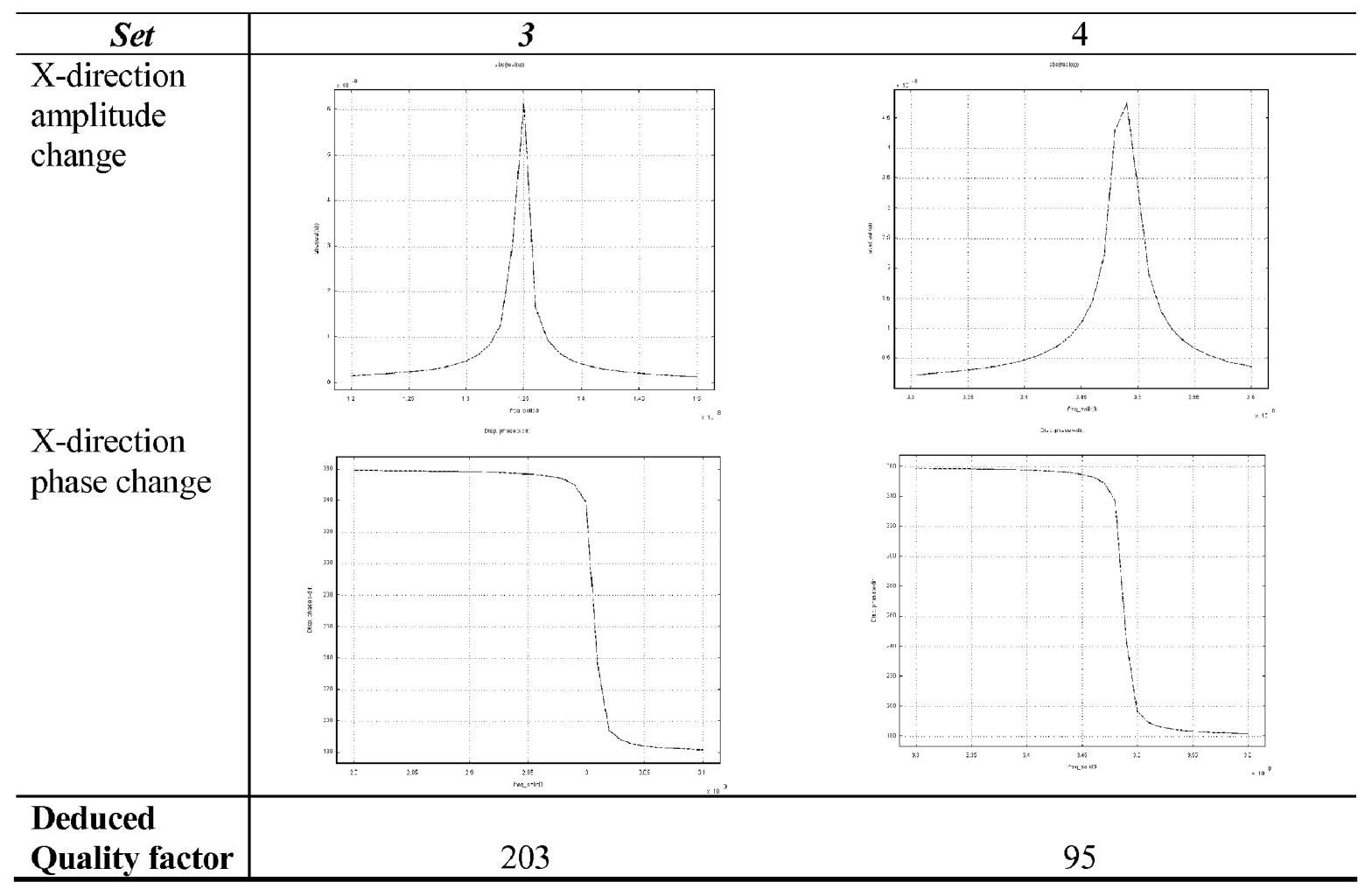
Figure 18C:
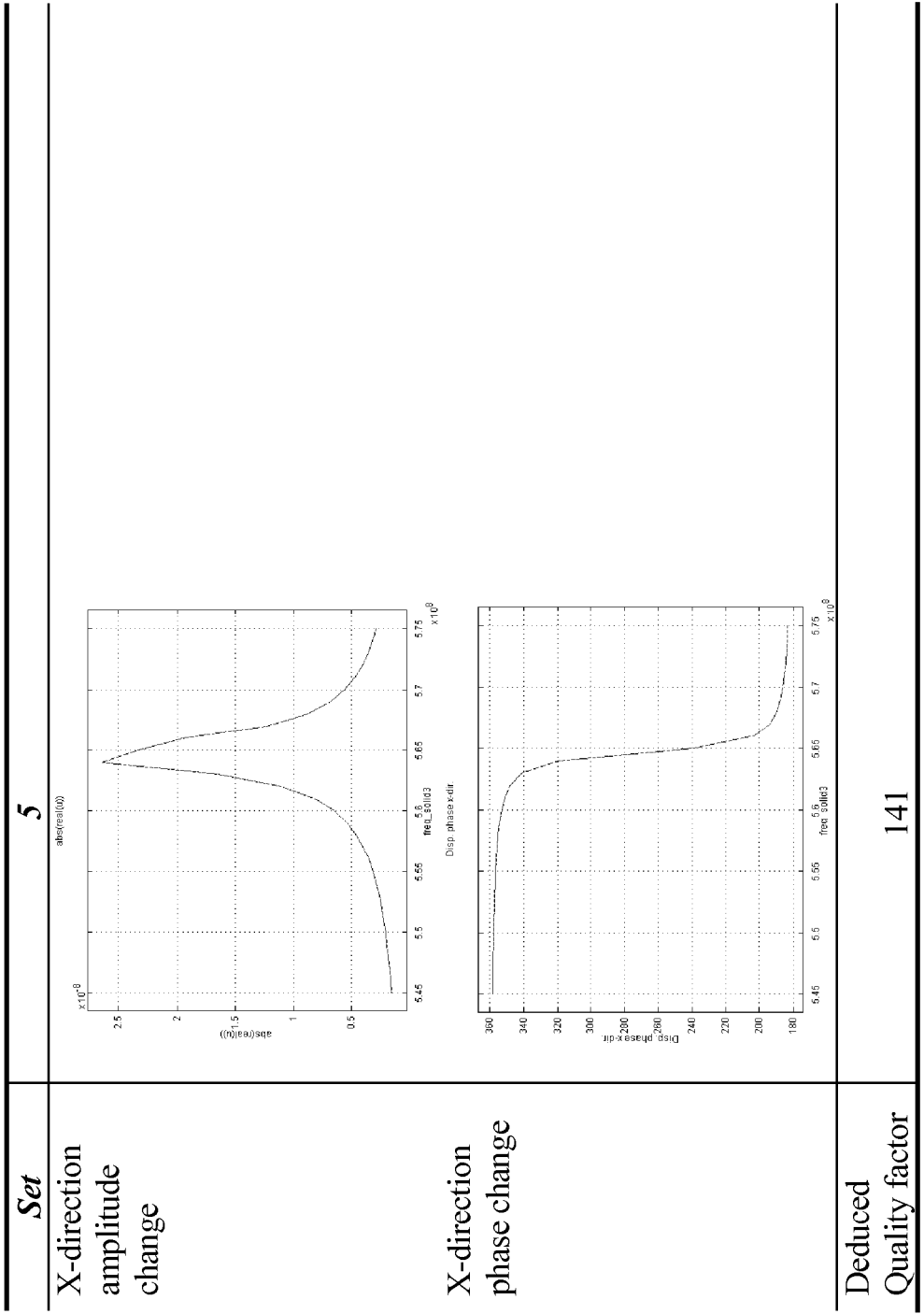

FIGS. 18A-C shows the allowed amplitude and phase changes for frequency scan over pillar fundamental frequencies (see corresponding Tables 1-3 for conditions) determined in the modeling study. Sets 1-5 referenced in FIGS. 18A-C correspond to the pillar geometries of sets 1-5 set forth in Table 3. The frequency response curves shown in FIGS. 18A-C are characterized by a single maximum and a narrow frequency distribution. This high degree of spectral purity indicates that the modeled resonator geometries provide good detection sensitivity. Also provided in FIGS. 18A-C are the deduced Quality factors corresponding to each mechanical mode evaluated.

Figure 14:
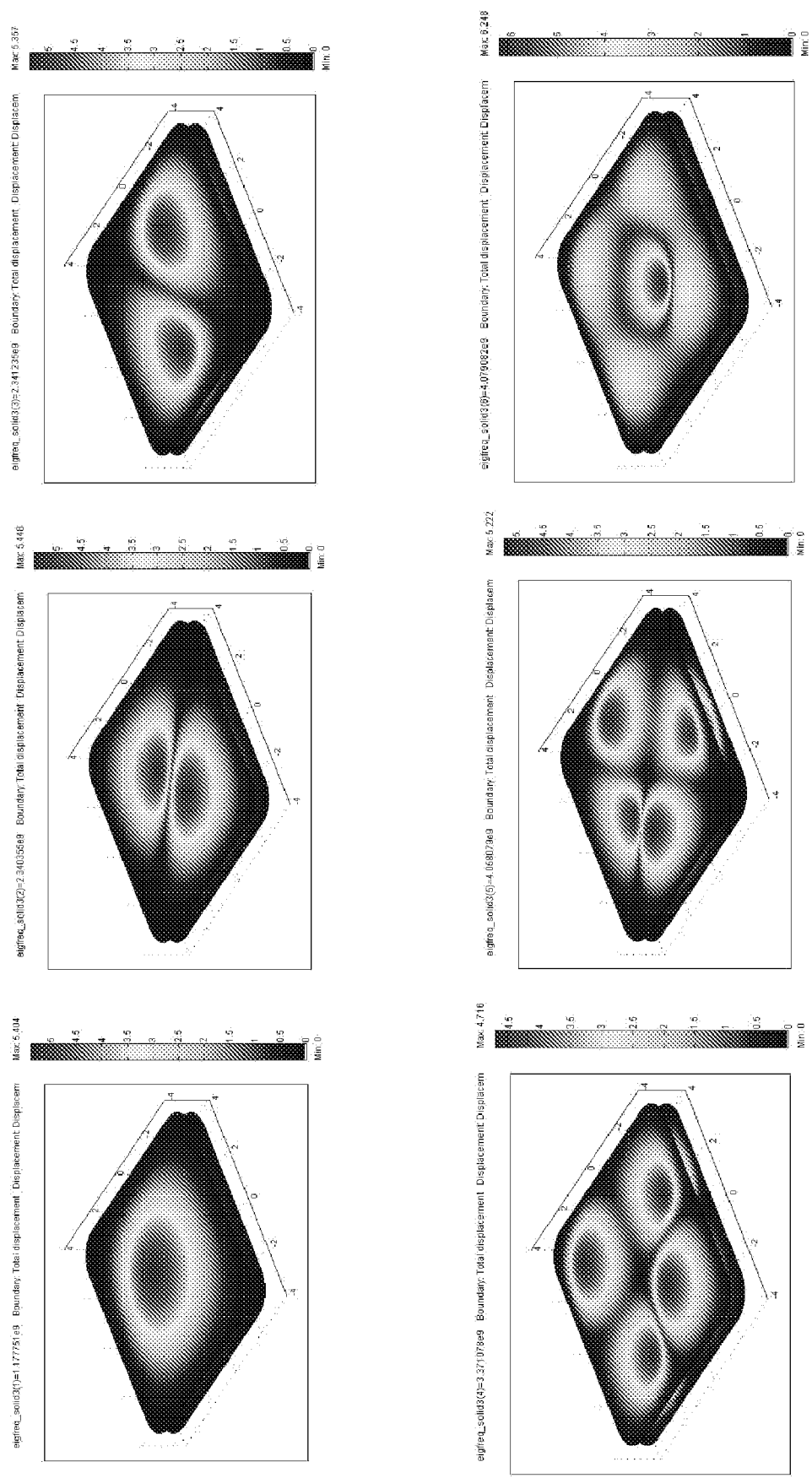
FIG. 14 provides modeling results showing simulated vibrational motion corresponding to various eigenmodes for the membrane only.
Figure 15:
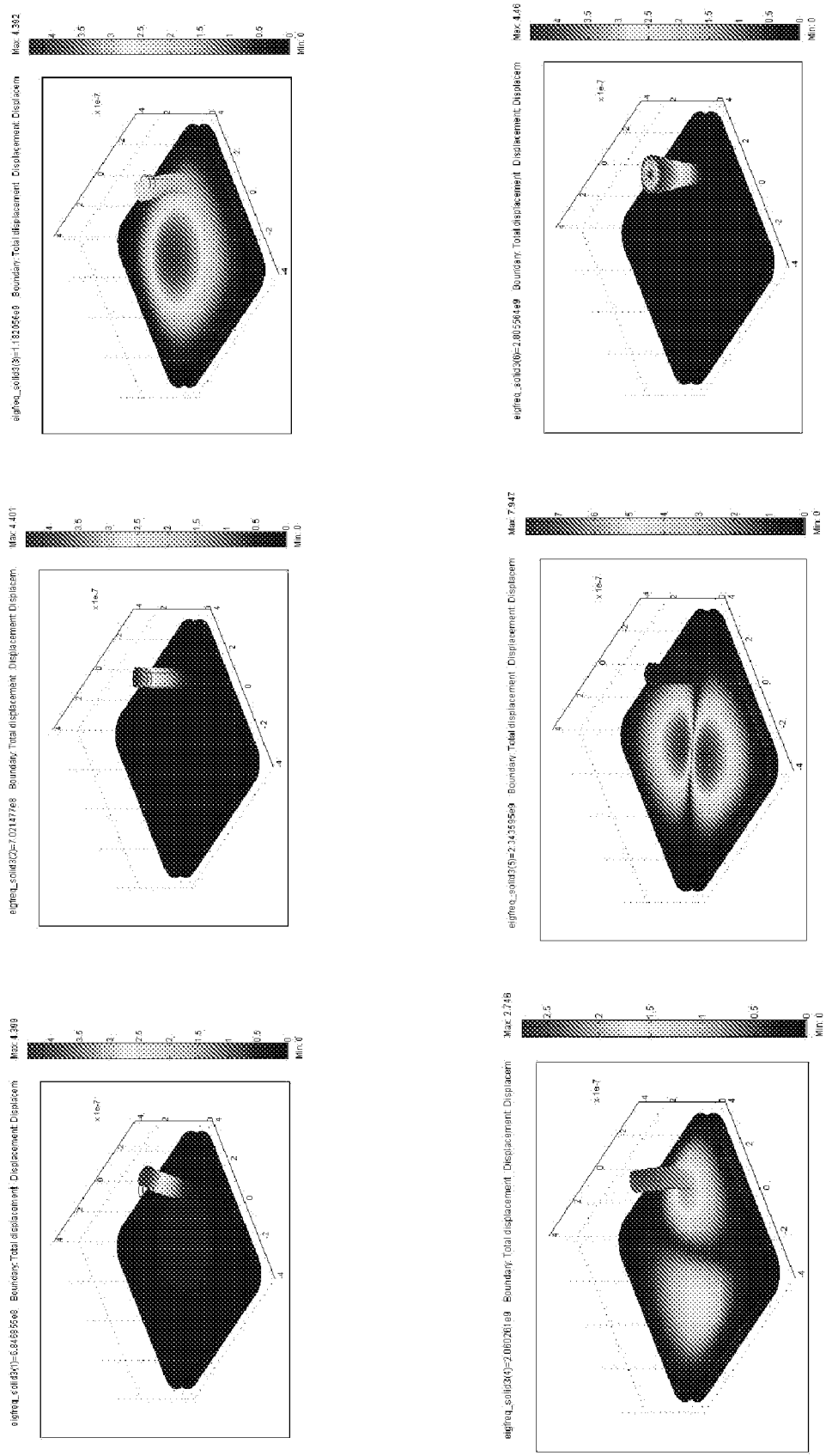
FIG. 15 provides modeling results showing simulated vibrational motion corresponding to various eigenmodes for the membrane and a cylindrical pillar resonator mechanically coupled to the membrane.

FIG. 14 provides modeling results showing simulated vibrational motion corresponding to various eigenmodes for the membrane only. FIG. 15 provides a modeling results showing simulated vibrational motion corresponding to various eigenmodes for the membrane and a cylindrical pillar resonator mechanically coupled to the membrane.

Figure 16:
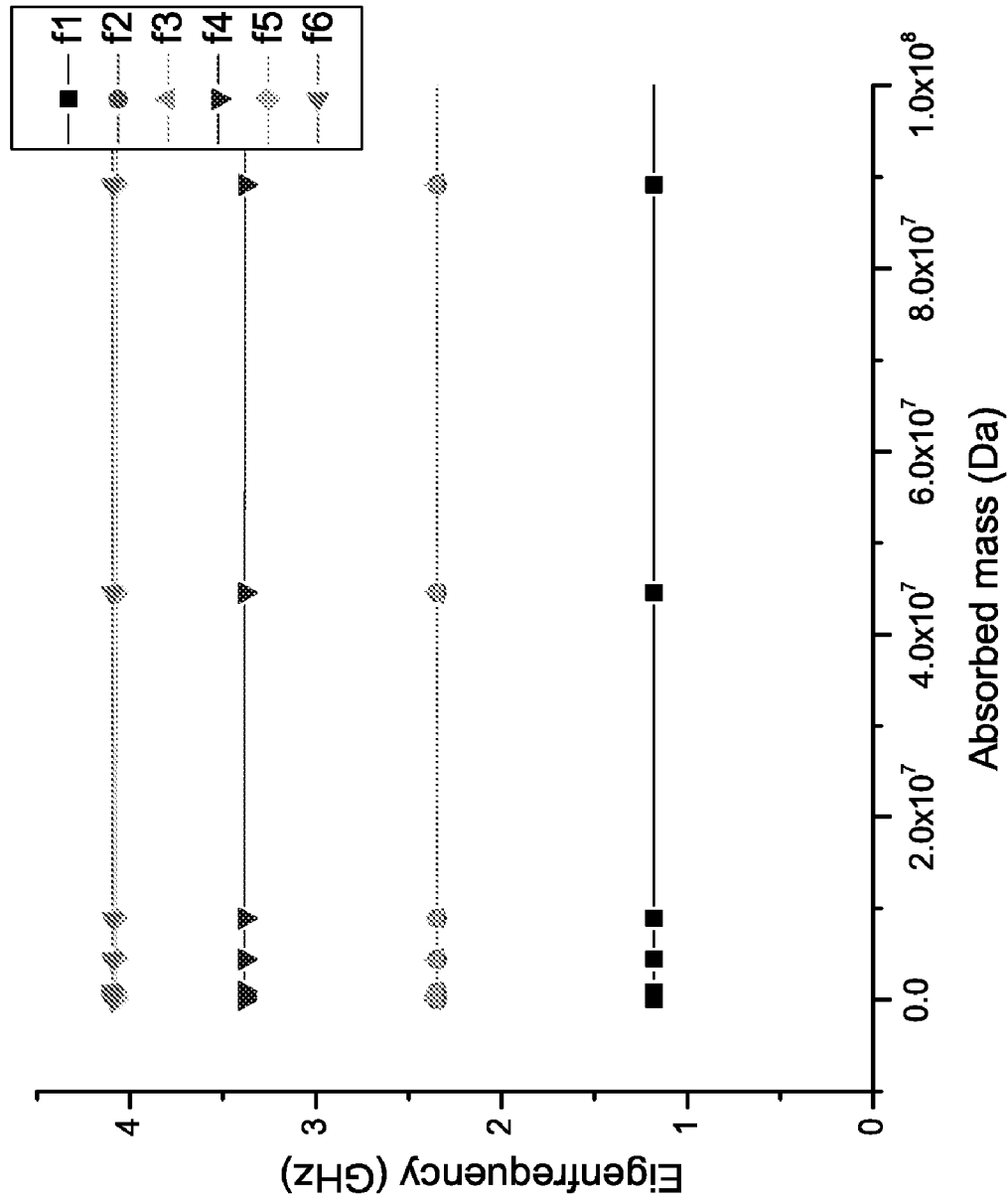
FIG. 16 provides a plot of the calculated frequency response verses mass to the membrane.
Figure 17:
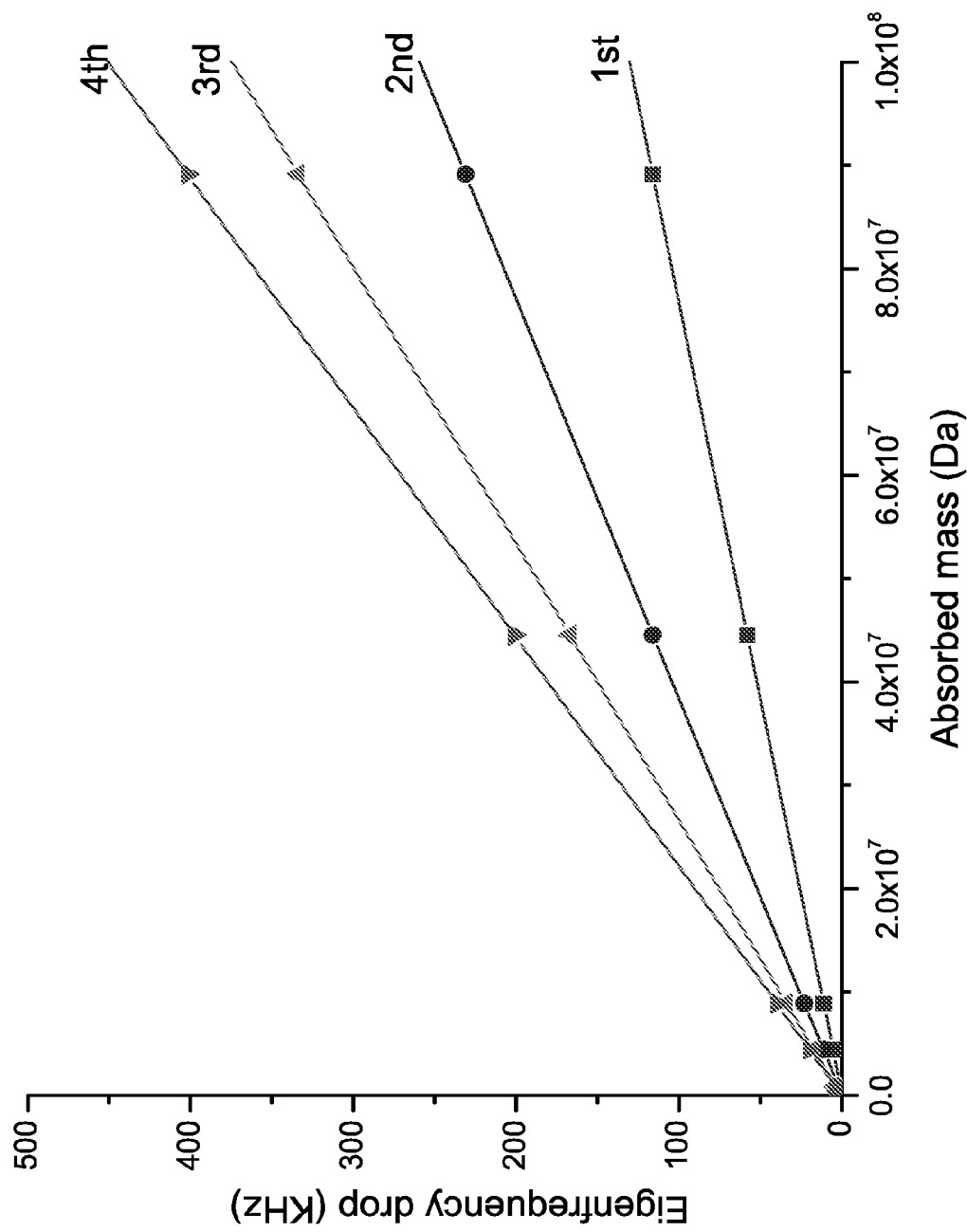
FIG. 17 provides a plot of the calculated change in frequency verses mass added to the membrane.

FIG. 16 provides a plot of claculated frequency response verses mass to the membrane and FIG. 17 provides a plot of the calculated change in frequency verses mass added to the membrane. Best performance is achieved when the pillar displacement is largest. This in turn is achieved with pillars having a pronounced waist line. Tuning of the mechanical quality factor can be performed.

EXAMPLE 2

Sensors for Mass Spectrometry Analysis

The present invention provides sensors and analyzers for mass spectrometry that are compatible with a variety of ionization sources, including but not limited, electrospray ionization, MALDI and nebulization ion sources, and compatible with a variety of mass analysis schemes including, but not limited to, TOF, quadrupole, magnetic sector and ion trap mass analyzers. The present sensors and detectors provide a detection sensitivity that increases with increasing mass, in contrast to conventional MCP detectors, and provide measurements with good temporal resolution. Accordingly, devices of the present invention are ideally suited for detection applications in TOF mass analysis systems.

To provide a detector for a TOF mass analyzer, a sensor of the present invention is positioned at the outlet of the TOF flight tube such that ions exiting the flight tube collide with the receiving surface of the sensor. This configuration allows analyte ions exiting the flight tube to be detected as a function of time, thereby providing information relating to the flight times of analytes ions passing through the flight tube. With knowledge of flight times, mass-to-charge ratio of the analyte ions can be easily extracted.

In a useful embodiment providing measurements of analyte flight times with good temporal resolution, each resonator mechanically and/or electrically coupled to the sensor membrane is electrically biased, mechanically biased or both electrically and mechanically biased such that they only generate emission upon interaction of a molecule with a region of the receiving surface proximate to the resonator. Upon impact of a molecule with the receiving surface, a time dependent emission signal is generated characterized by a rapid increase in intensity corresponding to the perturbed state that is followed by a relaxation of the signal back to a nonemissive unperturbed state occurring on a slower time scale. In this Off-On readout mode, generation of emission from one or more resonators signifies a detection event for determining analyte ion flight times.

Electrical biasing in this embodiment may be achieved using any means known in the art including biasing through the membrane (i.e. via application of an electric potential to the membrane) and/or biasing provided by a grid electrode positioned between the inner surface of the membrane and the detector. Electrical biasing may also be provided by selection of the composition of the resonators, such as the extent of doping and/or metallization of the resonator. Mechanical biasing in this embodiment may be achieved by selection of the composition and physical dimensions of the resonators and the membrane. In one sensor scheme, the mechanical biasing provided may be selectively adjusted by incorporation of a means of adjusting the elasticity of the membrane.

In one embodiment, the field emitting resonators are electrically biased to values in the range of about 50-500 mV, and preferably for some applications the range of about 50 mV to about 10V, depending on resonator material, geometry, and mechanical mode selected. Preferentially for the off/on mode operation the mechanical resonator can be mechanically excited into the non-linear regime in which a small perturbation is sufficient to release the cumulated energy. The classical mechanical analog is a leaf spring—biased close to the transition point the mechanical mode is altered. The mechanical energy then supports the emission of electrons or electromagnetic radiation.

An alternative approach to the Off/On operation mode, involves providing a grid electrode (or mesh gating electrode) between the inner surface of the membrane and the detector. In this embodiment, the nano-pillars are electrically and/or mechanically biased so that they continuously emit electrons and/or electromagnetic radiation, which are at least partially absorbed by the mesh gating electrode when the pillars are in an unperturbed state. When a molecule interacts with the receiving surface and alters a pillar's resonance frequency, however, an increase in emitted electrons or electromagnetic radiation are transmitted through openings in the grid electrode due to changes in the spatial distribution of emission that accompany changes in resonance frequency. Detection of the increase in the intensity or power of emitted electrons or electromagnetic radiation transmitted by the mesh gating electrode results in a positive detection event.

FIGS. 19A, 19B and 19C provide schematic diagrams illustrating a detector configuration also providing sensitive detection with good temporal resolution. Three operating modes useful for this detector configuration are shown in FIGS. 19A-19C: (1) event detection via emitted photons, (2) event imaging and (3) event detection via current measurement. In each of the configurations illustrated a MCP detector is interfaced to receive emission from the resonators, and optionally a grid electrode is provided between the inner membrane surface and the MCP detector. The open areas and closed areas of the MCP detector are aligned relative to the position of resonators on the inner surface such that a change in the spatial distribution of emission from at least one resonator causes an increase in the current output of the MCP detector. As illustrated in FIGS. 19A-19C, a significant portion of the emission from resonators in an unperturbed state is directed onto closed areas of the MCP detector, which comprise conductive surfaces that do not initiate an electron cascade and amplification. However, this detection configuration provides that a change in resonance frequency of a resonator due to interaction of a molecule with the receiving surface results in a significant increase in the amount of emission from the perturbed resonator(s) that is directed onto the open areas of the MCP detector. Such a change in resonance frequency, therefore, results in a measurable change in current output from the MCP detector via initiating electron cascade and amplification. Monitoring this change in current as a function of time or position provides detection methods useful for a range of mass spectrometry applications, including TOF mass analysis.

FIG. 19A shows event detection operation mode via detection of emitted photons as a function of time. As shown in FIG. 19A, interaction between a molecule or packet of molecules and the receiving surface causes at least one field emitting resonator positioned proximate to the impact site to undergo a change in resonance frequency, thereby increasing the amount of emission that interacts with the open areas of the MCP detector. The MCP detector generates a cascade of secondary electrons resulting in a large gain in the signal. The resulting electrons from the MCP detector impact a phosphor screen that generates a stream of photons that are directed onto the active area of a phototube and detected. FIG. 19A also provides an exemplary temporal profile of current from the phototube as a function of time that is characterized by a rapid increase in current followed by signal decay occurring on a slower time scale. Analysis of the temporal profile provides information related to flight time and mass-to-charge ratio. For example, measurement of the timing of the rapid onset of current relative to when analyte ions enter the flight tube provides a measurement of flight time. Relaxation of the time dependent signal renders the sensor in an active condition ready for detection of the next molecules or packets of molecules exiting the flight tube.

FIG. 19B shows event imaging operation mode via characterization of the spatial distribution of emitted photons as a function of time. As shown in FIG. 19B a lens is provided to collect photons emitted by the phosphor screen and direct them onto the active area of a charge coupled device. The output of this detection scheme is an image of the impact location, which can be used in magnetic sector mass analyzers to determine mass-to-charge ratio. This detection scheme also provides temporal information useful for calculating flight times and mass-to-charge ratios. Subsequent molecules or packets of molecules are detected as they exit the flight tube, quadrupole or magnetic sector and interact with the receiving surface of the membrane.

FIG. 19C shows event detection operation via detection of current as a function of time. In this embodiment, a phosphor screen is not provided. Rather, current from the anode of the MCP detector is provided as input to a current amplifier. FIG. 19C also provides an exemplary temporal profile of voltage from the amplifier as a function of time that is characterized by a rapid increase in voltage followed by signal decay occurring on a slower time scale. Analysis of the temporal profile provides information related to flight time and mass-to-charge ratio.

Time of flight mass spectrometry requires determination of when an event occurs in order to obtain a measurement of the mass-to-charge ratio. Multipoles and ion traps need to determine if an event occurs in order to obtain a measurement of the mass-to-charge ratio. Magnetic sector mass spectrometers need to determine where an event occurred in order to obtain a measurement of the mass-to-charge ratio. Thus, either version of the event detector (photon or electron) may be used for time of flight, multipole, and ion trap spectrometers, while the magnetic sector instruments will require the imaging detector.

EXAMPLE 3

Evaluation of Field Emission from Nanopillar Arrays

To evaluate the usefulness of nanoelectromechanical structures and devices of the present invention for sensing applications, field emission from membrane-supported nanopillar arrays was detected and analyzed using a variety of detection and imaging configurations.

Figure 20B:
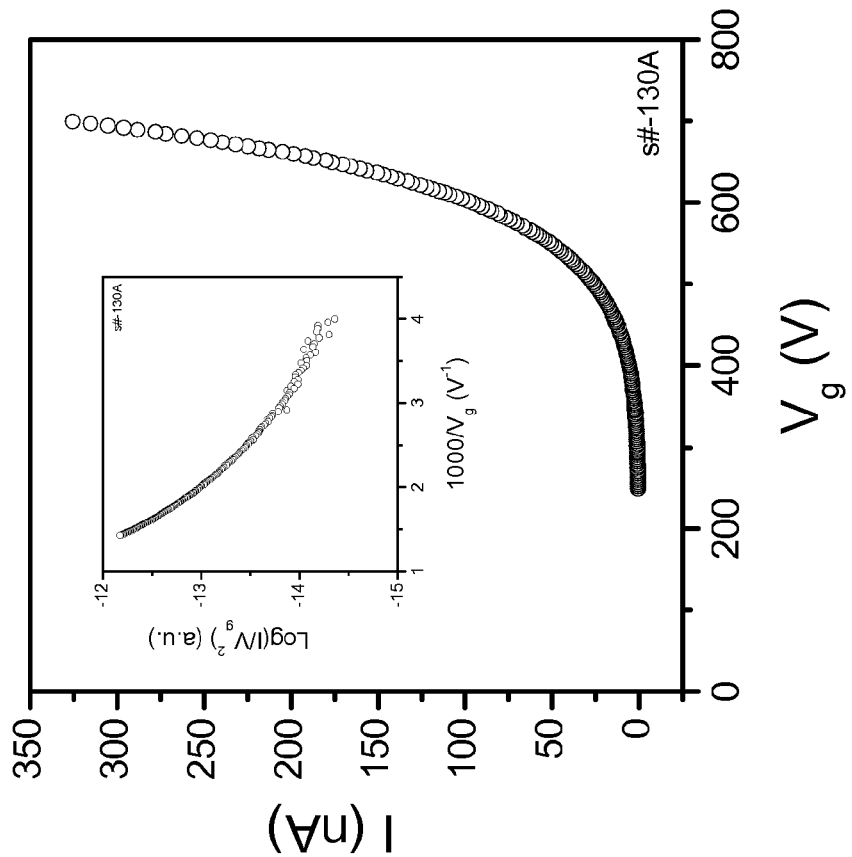
FIGS. 20A and 20B provide plots of current (nA) verse voltage (V) for an array of boron doped silicon nanopillars supported by a membrane.
Figure 20A:
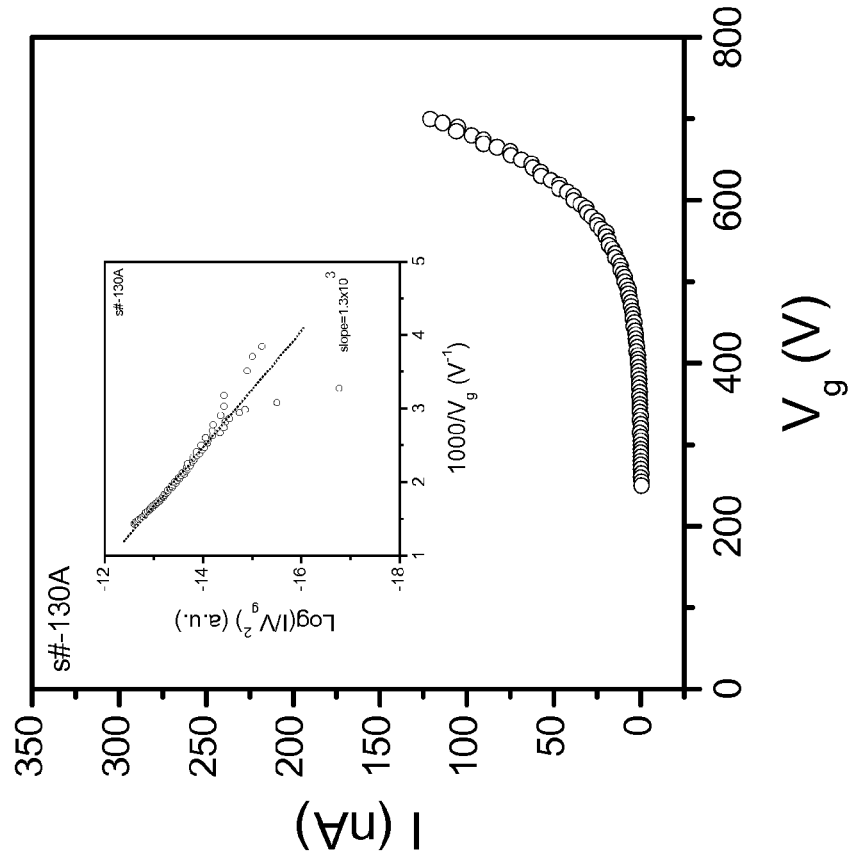

FIGS. 20A and 20B provide plots of current (nA) verse voltage (V) for an array of boron doped silicon nanopillars supported by a membrane. The nanopillars have gold field emitting tips that extend lengths about 40 nanometers and are positioned distal to the supporting membrane. Diameters and lengths of elements of the array are about 100 nanometer and 500 nanometers, respectively. Electrical biasing is achieved using a grid electrode having a selectively adjustable voltage positioned proximate to the nanopillar array. The voltage plotted in FIGS. 20A and 20B corresponds to the potential difference between the grid electrode and the membrane supporting the nanopillar array. Current plotted in FIGS. 20A and 20B is measured at the grid electrode. The data shown in FIGS. 20A and 20B correspond to electrical biasing conditions only, and the pillar resonators were not mechanically excited in these experiments.

As shown in FIGS. 20A and 20B, the current at the grid electrode increases very rapidly with increasing voltage. The insets in FIGS. 20A and 20B provide Fowler-Nordheim plot representations of the data. The linearity of the inset plot in FIG. 20A indicates that stable field emission is achieved for the range of voltages examined. Slight deviations from linearity are noticeable in the inset plot in FIG. 20B indicating the occurrence of space charge accumulation processes.

Figure 21B:
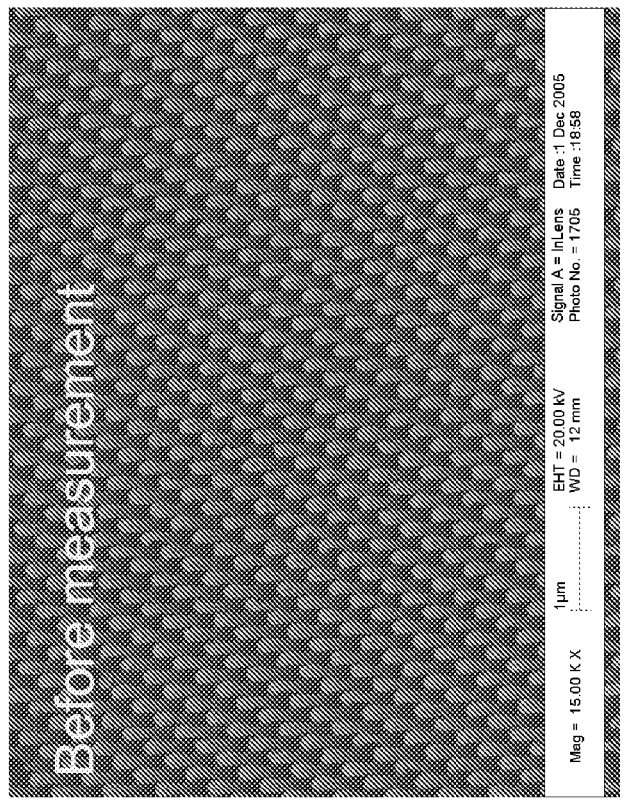
FIGS. 21A and 21B provide scanning electron micrographs of the nanopillar array before (21A) and after (21B) applying a very high voltage to the system.
Figure 21A:
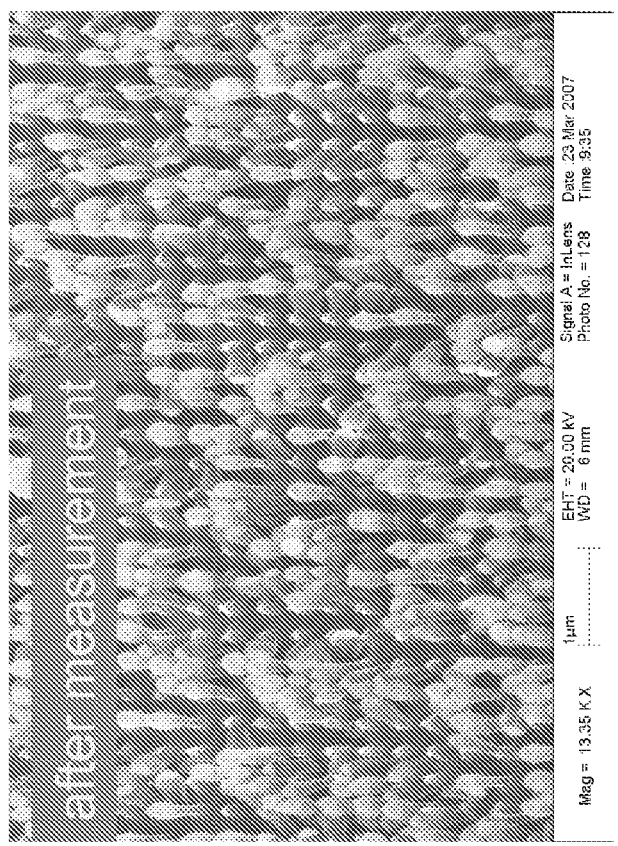

FIGS. 21A and 21B provide scanning electron micrographs of the nanopillar array before (21A) and after (21B) applying a very high voltage to the system. FIG. 21A shows a well order symmetric array comprising a plurality of nanopillars with field emitting metallic tips. In contrast, FIG. 21B shows a disorder array comprising at least some nanopillars which have collapsed onto each other. It is likely that exposure of the array to the very high voltage caused chemical modification of some of the pillars, as indicated by the changes in shapes of pillars in the array. In addition, it is possible that interactions between adjacent nanopillars at very high voltage led to collapse of at least some of these nanostructures.

Figure 22B:
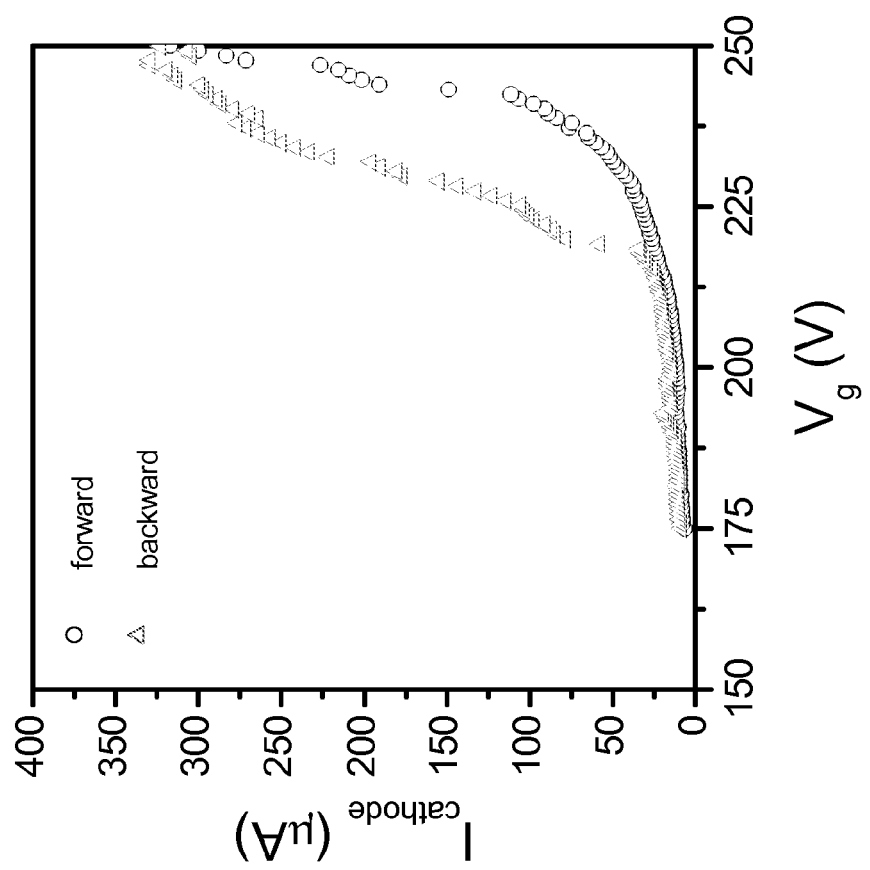
FIGS. 22A and 22B provide plots of anode current from the MCP as a function of bias voltage. The open circles in these figures correspond to experiments in which the voltage was incrementally increased and the open triangles correspond to experiments in which the voltage was incrementally decreased.
Figure 22A:
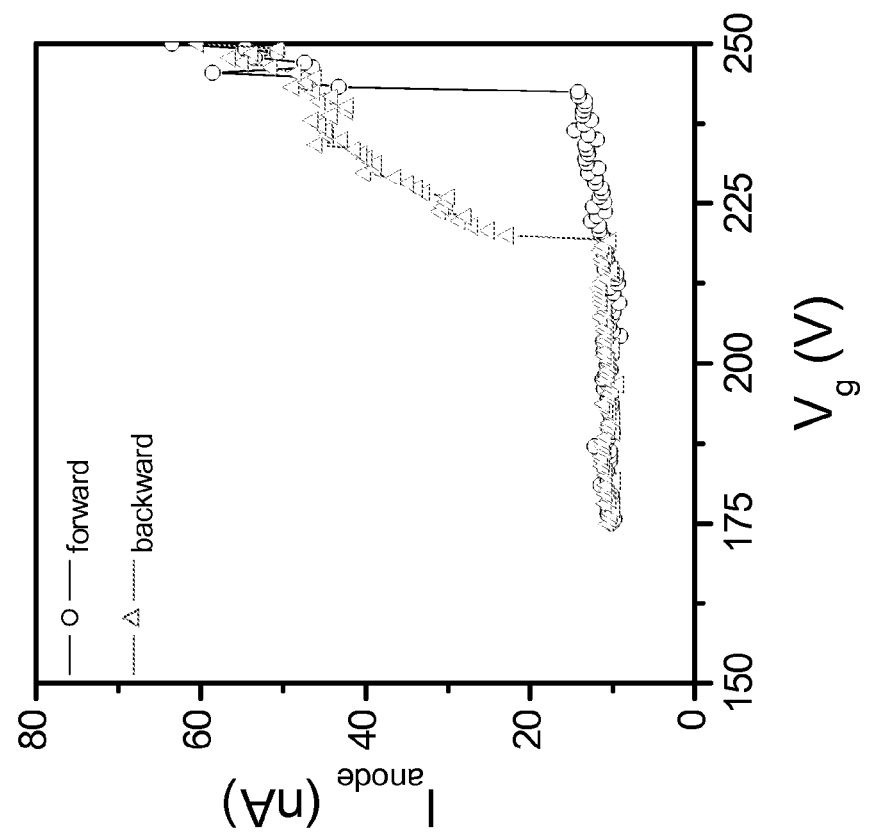

Field emission from nanopillar arrays was also evaluated using a detector configuration involving a MCP detector. In these experiments, the MCP detector was positioned to receive field emission from the nanopillar array. Specifically, the MCP detector was positioned such that at least a portion of the emission from the nanopillar array passed through the grid electrode and onto the active area of the MCP detector. FIGS. 22A and 22B provide plots of anode current from the MCP as a function of bias voltage. The anode current from the MCP detector indicates electrons are emitted from the nanopillar array. As described above, electrical biasing in these experiments is achieved by adjustment of the grid electrode voltage and the data shown in FIGS. 22A and 22B correspond to electrical biasing conditions only (i.e., the pillar resonators were not mechanically excited).

As shown in FIGS. 22A and 22B, a very steep increase in anode current is observed upon increasing the bias voltage applied to the nanopillars. The steep turn on threshold behavior indicates that good sensitivities are likely accessible using this detector configuration and that dark current is not likely to significantly impact the functioning of the sensor. The open circles in these figures correspond to experiments in which the voltage was incrementally increased and the open triangles correspond to experiments in which the voltage was incrementally decreased. As is evident from FIGS. 22A and 22B, a hysteresis phenomenon is observed in the comparison of anode currents measured on increasing the bias voltage as compared to anode currents measured on decreasing the bias voltage. This is likely due to charge accumulation processes in the nanopillars of the array.

Figure 23:
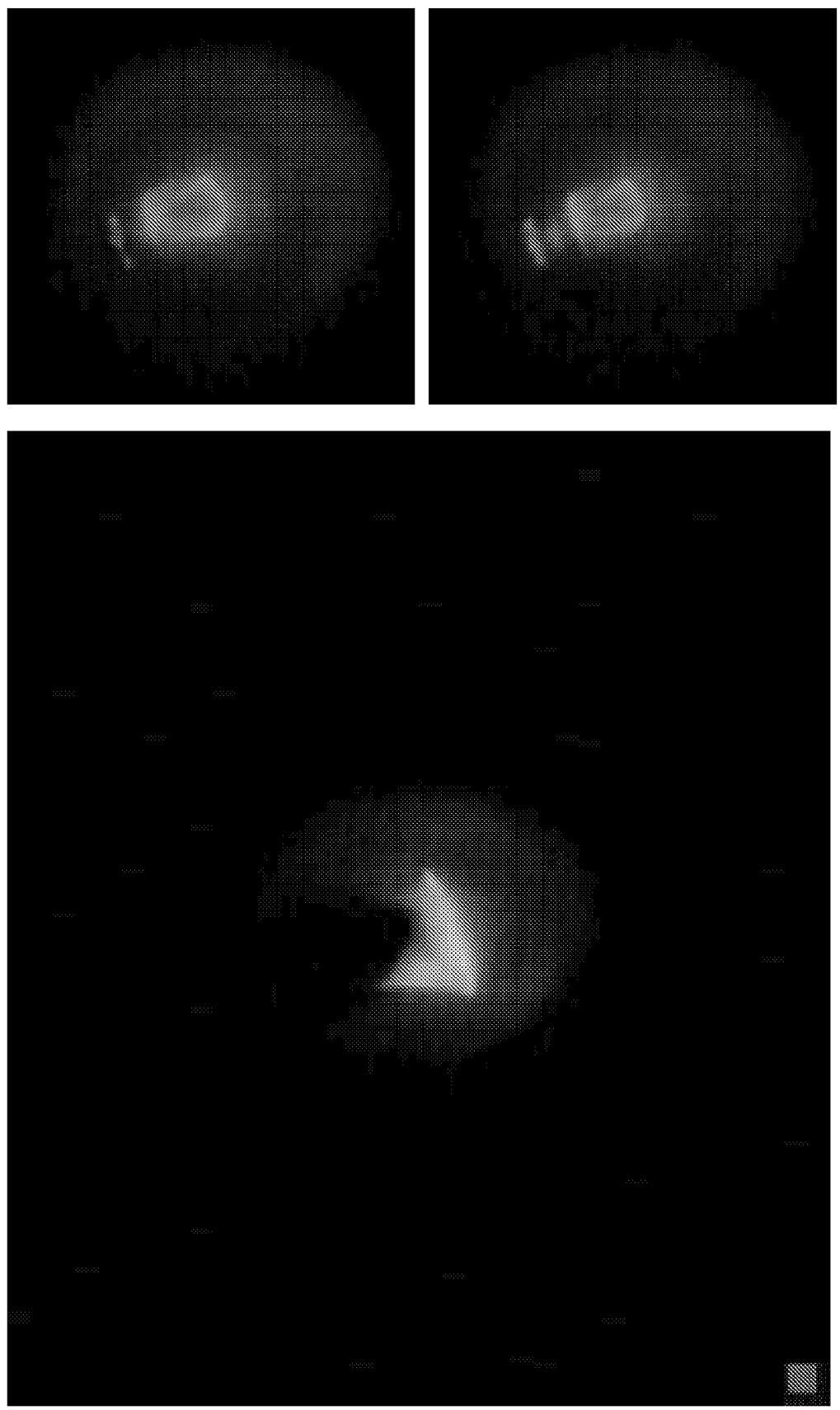
FIG. 23 shows fluorescent images generated upon tuning the bias voltage applied to the nanopillar array from 0V to +300V and back to 0V.

Field emission from nanopillar arrays was also evaluated using an imaging configuration involving a combination of a MCP detector and fluorescent screen. In these measurements the fluorescent screen was coupled to the MCP detector such that amplified current from the MCP detector excited fluorophors in the fluorescent screen so as to provide imaging of field emission from the nanopillar array. FIG. 23 shows fluorescent images generated upon tuning the bias voltage applied to the nanopillar array from 0V to +300V and back to 0V. The image shape shown in FIG. 23 is observed to correspond to the nanopillar/membrane geometry of the sensor.

EXAMPLE 4

Field Emission from a Single Nanomechanical Pillar

We measured field emission from a silicon nanopillar mechanically oscillating between two electrodes. The pillar has a height of about 200 nm and a diameter of 50 nm, allowing resonant mechanical excitations at radio frequencies. The tunneling barriers for field emission are mechanically modulated via displacement of the gold island on top of the pillar. We present a rich frequency-dependent response of the emission current in the frequency range of 300–400 Hz at room temperature. Modified Fowler-Nordheim field emission is observed and attributed to the mechanical oscillations of the nanopillar.

Field emission is one of the essential techniques for building flat panel displays. Typically an array of sharpened electrodes is placed in close vicinity to a fluorescent screen and gated by a mesh electrode. Control of the emission current is commonly only achieved by biasing the electrodes and the gating grid. However, others have studied field emission from single nanotubes which were mechanically excited in one of their eigenmodes. We consider it desirable to integrate a mechanical modulation scheme: the specific advantages being non-volatile operation, integration of sensor components, and a better control of the emitted current. Recently we have demonstrated field emission in a lateral nano-electromechanical single electron transistors (NEMSET). In such a lateral NEMSET, field emission is assisted by mechanical motion and is in turn greatly modified in comparison to normal Fowler-Nordheim theory if the emission occurs from an isolated island placed on a nanomechanical resonator. This has the great advantage that field emission is regulated by changing the island dimensions. In addition the emission current can be mechanically clocked up to 1 GHz.

In this Example we demonstrate field emission from a vertical single nanopillar enhanced by its mechanical oscillations. The prime advantages of using silicon pillars are their nanoscale diameter, structural integrity, tunable conductivity, and chemical stability. An even more specific advantage of the pillar structure is that it can be integrated over a large scale as conventional field emitter arrays. While contacts for the nanopillar investigated here are situated to the left and right, a field emitter version for display applications of this NEMSET would use pillars made from highly doped semiconducting base material.

Figure 24:
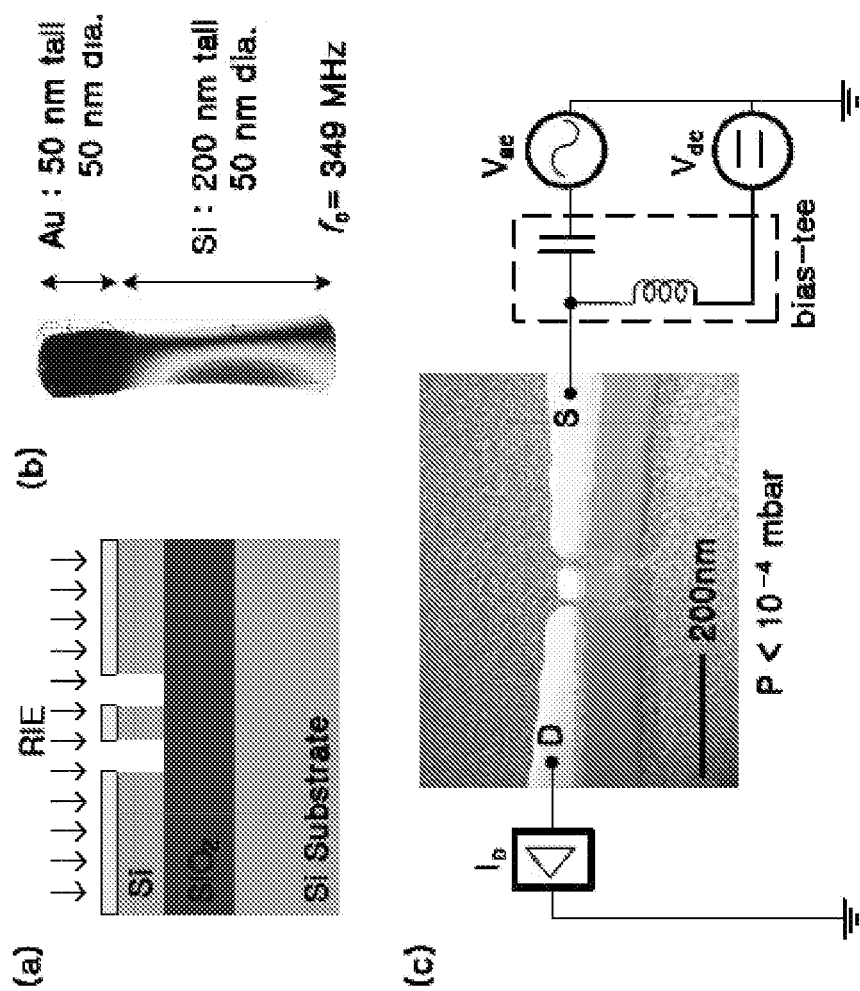
FIG. 24: (a) Two processing steps: nano electron-beam lithography and dry etching in a fluorine reactive ion etcher. (b) Finite element modeling of the nanopillar structure reveals the eigenfrequency and the stress profile. (c) SEM micrograph and the measurement circuitry: At source S, we apply both an ac signal $V_{ac}$ and a dc bias $V_{dc}$. The net current $I_D$ at drain D is measured with a current amplifier.

The device studied is introduced in FIG. 24: (a) shows a sketch of the fabrication; using electron beam lithography and gold evaporation, a pair of electrodes and an isolated island were defined; in a second step, anisotropic dry etching was applied in a fluorine reactive ion etcher (RIE) so that the pillar is carved out of the silicon-on-insulator base material. The mechanically flexible pillar has a length of some 200 nm and a diameter of some 50 nm. In (b), a finite element simulation shows the stress profile of the pillar in its first eigenmode. The eigenmodes can be engineered by the sidewall profile and the dimension of the pillar. Since both the electrodes and the pillar are covered with a 50 nm thick gold layer, electron transport occurs in the gold layer instead of the underlying silicon. The left and right electrodes serve as source and drain contacts with the pillar shuttling electrons between them. These contacts are not only for providing electrons but also for ac excitation.

For mechanical excitation of the pillar, we employ the resonant Coulomb force (RCF) method: an ac excitation voltage $V_{ac}$ applied at the source contact induces mechanical motion. The resonant mechanical oscillations strongly modulate the electric field between the pillar and the contacts, providing the local field strength necessary for field emission [see FIG. 24(c)]. In addition to the ac voltage, a dc voltage $V_{dc}$ is applied via a bias-tee so that the threshold of field emission can be precisely controlled. As long as the dc bias is small compared to the ac amplitude, RCF is dominant for the current flow between pillar and electrodes. The pillar exchanges electrons across the tunneling barriers by reducing the distance between the pillar and the respective electrode when it is deflected by an ac excitation.

We have probed the basic current-frequency response in a probe station at a pressure of less than $10^{-4}$ mbar at room temperature. The drain (D) current $I_D$ was recorded vs. the ac excitation frequency f at an incident ac power P and a dc bias voltage. We measured the power attenuation factor in the circuit to be $\sim 1 \times 10^{-3}$ and the impedance to be $\sim 500 \Omega$ using a network analyzer (Agilent E8357A). FIG. 25(a) shows the recorded dc current obtained with a pure ac excitation. Two eigenmodes are observed with different amplitudes, one at 310 MHz and the other at 372 MHz. Based upon the simulation shown in FIG. 24(b), we attribute these to a slightly asymmetric shape of the nanopillar. The small oscillatory features in FIG. 25(a) may relate to small variations in the ac power applied. The current at the two eigenfrequencies can be greatly enhanced by applying a dc bias voltage as shown in FIG. 25(b). The inset of FIG. 25(b) shows the nonlinear I-V behavior which again shows maximum current at the eigenfrequencies. Voltage sweeps were conducted and the current was monitored at fixed excitation frequencies. In the voltage sweeps, the bias $V_{dc}$ was ramped from −1 V to +1 V at a rate of 2 mV/step at each of the on- and off-resonance frequencies. Each sweep was reproduced over 15 times to ensure stability of the device's I-V characteristics. The nonlinear I-V behavior and the nature of the isolated pillar strongly suggests the observed current signal results from field emission of electrons. Field emission occurs when the applied electric field at the pillar lowers the potential barrier to the point where electron tunneling is enabled. The electrons are emitted from the isolated island on top of the pillar towards one of the electrodes. The mechanical modulation allows for subsequent charging of the pillar. As the tunneling rate depends exponentially on the distance between gate and pillar, field emission is strongly altered through the mechanical motion of the pillar. This is further confirmed by comparing the data to the well-known Fowler-Nordheim theory. Much of the analysis of the experimental data is based on the Fowler-Nordheim field emission mechanism by taking into account the presence of an ac voltage and the effect of the mechanically modulated electric field. The most important effect is the mechanical modulation of the electric field between pillar and electrode. The standard field emission analysis often involves a plot of $\ln(I/V^2)$ vs. $1/V$. The emission current is determined by the Fowler-Nordheim equation: $I = \alpha V^2 \exp(-\beta/V)$, where $\alpha$ and $\beta$ are geometrical factors representing device details, which can be expressed as the ratio of field enhancement to the distance between pillar and electrode.

FIG. 26(a) shows Fowler-Nordheim plots for the cases of a pure dc bias and a dc bias with an ac excitation for on- and off-resonance frequencies. In the experimental regime of no RF and off-resonance, field emission is extremely weak. The off-resonance curves resemble the no RF case with a slightly higher current due to the ac voltage. However, there is an obvious current change between on- and off-resonance. Under resonant excitation the pillar is vibrating and hence induces mechanically enhanced field emission from both ac and dc biases. Since both ac and dc electric fields induce field emission the dc current measured is a sum of both. For higher dc voltages, the field emission current is dominated by the dc field rather than the ac field. The straight lines indicate that the emission mechanism is likely to be from Fowler-Nordheim Fermi tunneling in the high dc bias regime independent of the ac signal. The conventional Fowler-Nordheim curve disappears as the ac field is increased. To model the data of the graphs shown in FIG. 26, we calculated the time-averaged tunneling current with the following equation $$I = \langle \bar{I}(V_{dc}, V_{ac}(t)) \rangle \cong \int_0^{1/f} \alpha f (V_{dc} + V_{ac})^2 \exp\left[-\frac{\beta}{(V_{dc} + V_{ac})}\right] dt, \qquad (1)$$

where $\alpha$ and $\beta$ are modulated by mechanical oscillations of the pillar and $V_{ac} = |V_{ac}|\cos(2\pi ft)$. These modified Fowler-Nordheim curves can be approximated by the following expression $$\ln(I/V_{dc}^2) \cong \begin{cases} 2\ln(V_{ac}/V_{dc}) - \beta/V_{ac}: & V_{ac} \gg V_{dc} \\ -\beta/V_{dc}: & V_{ac} \ll V_{dc}. \end{cases} \qquad (2)$$

The fits based on Eq. (1) are compared to the measured data in In $(I/V_{dc}^2)$ vs. $1/V_{dc}$ plots. We have found good agreement between theory and the experimental data. FIG. 26(b) shows one of the on-resonance curves shown in FIG. 26(a), nicely fitted by a Fowler-Nordheim approach. Based on this model, we estimate the deflection distance ranges from 0 to 15 nm depending upon the ac power applied. The deflection distance d is proportional to the square root of incident ac power ($\sqrt{P}$). Since the initial electrode-island distance is 20 nm, we assume that the pillar does not make contact with the electrodes during this deflection. The electron transport is completely through field emission.

In summary the observed behavior demonstrates field emission in this particular geometry. This mechanically enhanced field emission will allow integration in devices such as field emitter arrays for flat panel display applications and sensor components.

We claim:

1. A sensor for sensing one or more molecules, said sensor comprising:
   a membrane having a receiving surface for receiving said molecules and an inner surface opposite to said receiving surface;
   means for vibrating the membrane;
   a plurality of electromechanical resonators extending vertically along a plurality of axes that intersect the inner surface of said membrane, wherein vibration of said membrane causes the resonators to resonate, said resonators comprising emissive elements that generate emission having a spatial distribution, wherein the spatial distribution of said emission from said resonators changes when the receiving surface receives said molecules; and
   a detector for receiving said emission from said resonators, wherein said detector detects said change in the spatial distribution of said emission from said resonators, thereby sensing said molecules.

2. The sensor of claim 1 wherein vibration of said membrane causes each resonator to resonate at a resonance frequency, and wherein the resonance frequency of at least one resonator changes when the receiving surface receives said molecules.

3. The sensor of claim 1 wherein vibration of said membrane causes said resonators to resonate at substantially the same resonance frequency.

4. The sensor of claim 1 wherein vibration of said membrane causes at least a portion of said resonators to resonate at different resonance frequencies.

5. The sensor of claim 1 wherein said resonators oscillate via vibrational mechanical modes, rotational mechanical modes, counter-rotational mechanical modes or flexural mechanical modes.

6. The sensor of claim 1 wherein said resonators comprise nano-electromechanical resonators, micro-electromechanical resonators or both nano-electromechanical resonators, micro-electromechanical resonators.

7. The sensor of claim 1 wherein said resonators comprise pillars having vertical lengths extending along said axes that intersect the inner surface of said membrane and wherein said pillars vibrate laterally with respect to their vertical lengths.

8. The sensor of claim 7 wherein vibration of said membrane causes said pillars to vibrate with fundamental lateral vibrational modes having resonant frequencies selected over the range of about 1 MHz to about 10 GHz.

9. The sensor of claim 7 wherein said pillars have substantially the same physical dimensions.

10. The sensor of claim 7 wherein at least a portion of said pillars have different physical dimensions.

11. The sensor of claim 7 wherein said vertical lengths of said pillars are selected over the range of about 100 nanometers to about 3 microns.

12. The sensor of claim 7 wherein said pillars have average cross sectional dimensions selected over the range of about 10 nanometers to about 500 nanometers.

13. The sensor of claim 7 wherein said pillars have a cross sectional shape selected from the group consisting of a circle, square, rectangle, triangle, polygon, and ellipse.

14. The sensor of claim 7 wherein at least a portion of said pillars have a cross sectional dimensions that are substantially constant as a function of their vertical lengths or wherein at least a portion of said pillars have cross sectional dimensions which vary with said vertical length so as to form a waist in the pillar.

15. The sensor of claim 7 wherein each of said pillars comprise a material having a Young's modulus selected from the range of about 500 MPa to about 500 GPa.

16. The sensor of claim 1 wherein said resonators are provided in an array having a symmetrical or an asymmetrical spatial distribution of said resonators.

17. The sensor of claim 1 wherein said resonators are separated from each other by an average distance selected over the range of about 100 nanometers to about 1000 nanometers.

18. The sensor of claim 1 wherein each of said resonators comprise a semiconductor material.

19. The sensor of claim 1 wherein said resonators comprise field emissive elements that emit electrons.

20. The sensor of claim 19 wherein each of said field emissive elements comprises a semiconductor base connected to a metallic field emitting tip.

21. The sensor of claim 20 where said field emissive elements are pillars that extend vertical lengths along said axes that intersect the inner surface of said membrane, wherein said semiconductor base is doped with dopant, and wherein the spatial distribution of dopant is graded along the vertical length of the pillar.

22. The sensor of claim 1 wherein said resonators comprise photoemissive elements that emit electromagnetic radiation.

23. The sensor of claim 22 wherein said photoemissive elements are optical active semiconductor heterostructures comprising a surface emitting laser or a surface emitting light emitting diode.

24. The sensor of claim 1 wherein said membrane comprises a material capable of generating and supporting a periodic surface acoustic wave.

25. The sensor of claim 1 wherein said membrane comprises a piezoelectric material, and wherein said means for vibrating the membrane is a driving circuit capable of making the piezoelectric material vibrate.

26. The sensor of claim 1 wherein said means for vibrating the membrane comprises a dynamic membrane holder operably connected to the membrane such that it is capable of vibrating the membrane.

27. The sensor of claim 1 wherein said means for vibrating said membrane is capable of vibrating said membrane at a resonance frequency selected over the range of about 1 MHz to about 10 GHZ.

28. The sensor of claim 1 wherein said receiving surface of said membrane has an active area selected over the range of about 1 milimeters$^2$ to about 20 centimeters$^2$.

29. The sensor of claim 1 wherein said membrane has a thickness selected over the range of about 100 nanometers to about 1000 nanometers.

30. The sensor of claim 1 wherein said resonators are provided in physical contact with the inner surface of said membrane.

31. The sensor of claim 1 wherein said receiving surface of said membrane is functionalized to provide a high accommodation coefficient for receiving said molecules.

32. The sensor of claim 1 wherein said membrane is electrically biased so as to generate field emission, photoemission or both from said resonators.

33. The sensor of claim 1 wherein said detector is selected from the group consisting of:
   a multichannel plate;
   a charge coupled device;
   a photodiode array;
   an array of photomultiplier tubes;
   a photoluminescent screen; and
   a thin film display.

34. The sensor of claim 1 wherein said detector comprises a photoluminescent screen and photodetector, wherein said photoluminescent screen receives said emission from said resonators and generates electromagnetic radiation which is detected by said photodetector.

35. The sensor of claim 1 further comprising an electrically biased grid electrode positioned between said inner surface of said membrane and said detector.

36. The sensor of claim 35 wherein said grid electrode is partially transmissive of said emission.

37. The sensor of claim 1 further comprising means of releasing said molecule from said receiving surface.

38. The sensor of claim 37 wherein the means of releasing said molecule from said receiving surface generates a pulse of thermal energy, pulse of electromagnetic radiation, pulse of electric current or a shock wave on the receiving surface of said membrane that is capable of releasing said molecule from said receiving surface.

39. The sensor of claim 1 wherein said molecules possess electric charges, wherein at least some of said resonators further comprise a single electron transistor; wherein said detector measures a change in the intensity of emission generated by said resonators when the receiving surface receives said molecules, and wherein said change in the intensity of emission generated by said resonators indicates the electric charge of the molecule.

40. The sensor of claim 1 wherein said molecules possess electric charges, wherein said resonators further comprise high electron mobility transistors;
wherein said detector measures a change in the intensity of emission generated by said resonators when the receiving surface receives said molecule, and wherein said change in change in the intensity of emission generated by said resonators indicates the electric charge of the molecule.

41. A method of sensing one or more molecules, said method comprising the steps of;
providing a sensor comprising a membrane, a plurality of electromechanical resonators and a detector, wherein the membrane has a receiving surface for receiving said molecules and an inner surface opposite to said receiving surface, wherein the resonators extend vertically along a plurality of different axes that intersect the inner surface of said membrane, said resonators comprising emissive elements that generate emission having a spatial distribution, said detector positioned to receive said emission from said resonators;
vibrating said membrane of said sensor, wherein vibration of said membrane causes each of said resonators to resonate;
contacting said receiving surface of said membrane with said molecule, thereby causing a change in the spatial distribution of said emission from said resonators; and
detecting said change in the spatial distribution of emission from said resonators, thereby sensing the molecule.

42. The method of claim 41 wherein vibration of said membrane causes said resonators to resonate at resonance frequencies, and wherein said step of contacting said receiving surface of said membrane with said molecule changes the resonance frequency of at least one of said resonators.

43. The sensor of claim 42 wherein the resonance frequency of at least one resonator in the array changes by about 1% to about 10% when said molecule contacts the receiving surface.

44. The method of claim 41 wherein said electromechanical resonators are nano-electromechanical resonators, micro-electromechanical resonators or both.

45. The method of claim 41 comprising a method of determining the mass of the molecule, said method further comprising the step of measuring said change in the spatial distribution of emission from said resonators, thereby measuring the mass of the molecule.

46. The method of claim 41 wherein said molecules possess electric charges and wherein contact between said molecule and said receiving surface changes the intensity of emission from said resonators, said method comprising a method of determining the electric charges of the molecules, said method further comprising the step of measuring a change in intensity of emission from said resonators, thereby measuring said electric changes of the molecules.

47. The method of claim 41 wherein said step of detecting said change in the spatial distribution of emission from said resonators comprises the steps of:
providing a detector comprising a detection surface positioned to receive at least a portion of said emission, wherein said detector measures the area of said detection surface that interacts with emission from said resonators; and
detecting a change in the area of the detection surface that interacts with the emission from the resonators.

48. The method of claim 47 further comprising the steps of:
measuring a first area of the detection surface that interacts with the emission from the resonators prior to said step of contact said receiving surface with said molecules;
measuring a second area of the detection surface that interacts with the emission from the resonators after said step of contact said receiving surface with said molecules; and
comparing said first and second areas of said detection surface that interacts with the emission.

49. The method of claim 47 wherein the area of the detection surface that
interacts with emission from the resonators decreases when the receiving surface is contacted with the molecule.

50. The method of claim 47 wherein the area of the detection surface that
interacts with said emission changes by about 1% to about 10% when the receiving surface receives said molecule.

51. The method of claim 41 further comprising the step of releasing said molecule from said receiving surface.

52. A sensor for detecting one or more molecules, said sensor comprising:
a membrane having a receiving surface for receiving said molecules and having an inner surface opposite to said receiving surface;
means for vibrating the membrane;
a plurality of electromechanical resonators extending vertically along a plurality of axes that intersect the inner surface of said membrane, wherein vibration of said membrane causes the resonators to resonate, said resonators comprising emissive elements capable of generating emission, wherein at least one of said resonators generates emission when the receiving surface receives said molecules; and
a detector for receiving said emission from said resonators, wherein said detector detects said emission from said resonators, thereby detecting said molecules.

53. The sensor of claim 52 wherein said resonators are electrically biased so as to only generate emission upon contact between said receiving surface and said molecules.

54. The sensor of claim 53 wherein said resonators are electrically biased by applying a voltage to said membrane.

55. The sensor of claim 53 further comprising a grid electrode, wherein said resonators are electrically biased by providing an electrically biased grid electrode between said inner surface of said membrane and said emission detector.

56. The sensor of claim 52 wherein said resonators are mechanically biased so as to only generate emission upon contact between said receiving surface and said molecules.

57. The sensor of claim 52 wherein said resonators are nano-electromechanical resonators, micro-electromechanical resonators or both.

58. The sensor of claim 52 comprising a detector for a mass spectrometer selected from the group consisting of:
- a time-of-flight mass spectrometer;
- a FTIR mass spectrometer;
- a quadrupole mass spectrometer;
- an ion trap;
- a tandem mass spectrometer; and
- a magnetic sector mass spectrometer.

59. A liquid phase probe for sensing molecules in a solution, said probe comprising:

a membrane having a receiving surface for receiving said molecules in said solution and an inner surface opposite to said receiving surface;

means for vibrating the membrane;

a plurality of electromechanical resonators extending vertically along a plurality of axes that intersect the inner surface of said membrane, wherein vibration of said membrane causes the resonators to resonate, said resonators comprising emissive elements that generate emission having a spatial distribution, wherein the spatial distribution of said emission from said resonators changes when the receiving surface receives said molecules; and a detector for receiving said emission from said resonators, wherein said detector measures said change in the spatial distribution of said emission from said resonators, thereby sensing said molecules in solution.

* * * * *